(12) United States Patent
Chen et al.

(10) Patent No.: US 9,725,477 B2
(45) Date of Patent: *Aug. 8, 2017

(54) PLATINUM COMPOUNDS OF MALONIC ACID DERIVATIVE HAVING LEAVING GROUP CONTAINING AMINO OR ALKYLAMINO

(71) Applicant: BEIJING FSWELCOME TECHNOLOGY DEVELOPMENT CO., LTD, Beijing (CN)

(72) Inventors: Xiaoping Chen, Beijing (CN); Yashi Yan, Beijing (CN); Xiaoping Meng, Beijing (CN); Feng Zhao, Beijing (CN); Zejun Gao, Beijing (CN); Shouming Wen, Beijing (CN)

(73) Assignee: BEIJING FSWELCOME TECHNOLOGY DEVELOPMENT CO., LTD (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/762,145

(22) PCT Filed: Nov. 15, 2013

(86) PCT No.: PCT/CN2013/001390
§ 371 (c)(1),
(2) Date: Jul. 20, 2015

(87) PCT Pub. No.: WO2014/075391
PCT Pub. Date: May 22, 2014

(65) Prior Publication Data
US 2015/0368281 A1    Dec. 24, 2015

(30) Foreign Application Priority Data
Nov. 17, 2012    (CN) .......................... 2012 1 0466262

(51) Int. Cl.
*A61K 31/282* (2006.01)
*A61K 31/555* (2006.01)
*C07F 15/00* (2006.01)
*A61K 45/06* (2006.01)

(52) U.S. Cl.
CPC ........ *C07F 15/0086* (2013.01); *A61K 31/282* (2013.01); *A61K 31/555* (2013.01); *A61K 45/06* (2013.01); *C07F 15/0093* (2013.01)

(58) Field of Classification Search
None
See application file for complete search history.

(56) References Cited

U.S. PATENT DOCUMENTS

| | | | |
|---|---|---|---|
| 4,322,362 A | 3/1982 | Kaplan et al. | |
| 6,262,094 B1 | 7/2001 | Hoefle et al. | |
| 6,288,237 B1 | 9/2001 | Hoefle et al. | |
| 6,359,140 B1 | 3/2002 | Hofle et al. | |
| 6,384,230 B1 | 5/2002 | Mulzer et al. | |
| 6,624,310 B1 | 9/2003 | Hoefle et al. | |
| 7,067,544 B2 | 6/2006 | Hoefle et al. | |
| 7,407,975 B2 | 8/2008 | Klar et al. | |
| 9,138,421 B2* | 9/2015 | Chen ................... | C07F 15/0093 |
| 9,175,024 B2* | 11/2015 | Chen ................... | C07F 15/0093 |
| 2010/0330197 A1* | 12/2010 | Higashiguchi ........... | A23L 1/30 |
| | | | 424/638 |
| 2014/0142079 A1 | 5/2014 | Chen et al. | |

FOREIGN PATENT DOCUMENTS

| | | |
|---|---|---|
| CN | 101475600 A | 7/2009 |
| CN | 102863474 A | 1/2013 |
| DE | 4138042 A1 | 5/1993 |
| WO | 9719086 A1 | 5/1997 |
| WO | 9730992 | 8/1997 |
| WO | 9822461 A1 | 5/1998 |
| WO | 9825929 A1 | 6/1998 |
| WO | 9838192 A1 | 9/1998 |
| WO | 9854966 A1 | 12/1998 |
| WO | 9901124 A1 | 1/1999 |
| WO | 9902224 | 1/1999 |
| WO | 9902514 A2 | 1/1999 |
| WO | 9903848 A1 | 1/1999 |
| WO | 9907692 A2 | 2/1999 |
| WO | 9924416 A1 | 5/1999 |
| WO | 9927890 A2 | 6/1999 |
| WO | 9928324 A1 | 6/1999 |
| WO | 9943653 | 9/1999 |
| WO | 9954318 | 10/1999 |

(Continued)

OTHER PUBLICATIONS

Sporn et al. "Chemoprevention and cancer." Carcinogenesis. 2000; 21(3): 525-530.*
Thoppil et al. "Terpenoids as Potential Chemopreventive and Therapeutic Agents in Liver Cancer." World J. Hepatol. Sep. 27, 2011.; 3(9): 228-249.*
Costello et al. Evidence for changes in RREB-1, ZIP3 and zinc in the early development of pancreatic adenocarcinoma. J. Gastrointest. Canc. 2012; 43: 570-578.*
Kostova I. "Platinum complexes as anticancer agents." Recent Patents on Anti-Cancer Drug Discovery, 2006; 1: 1-22.*
Zorbas-Seifried et al. "Reversion of structure-activity relationships of antitumor platinum complexes by acetoxime by not hydroxylamine ligands." Mol. Pharmcol. 2007; 71: 357-365.*

(Continued)

*Primary Examiner* — Anna Pagonakis
(74) *Attorney, Agent, or Firm* — Lerner, David, Littenberg, Krumholz & Mentlik, LLP

(57) ABSTRACT

Disclosed are a class of platinum compounds of malonic acid derivatives having a leaving group containing an amino or alkylamino, and pharmaceutically acceptable salt thereof, preparation method thereof and pharmaceutical composition containing the compounds. Also disclosed are uses of the compounds for treating cell proliferative diseases especially cancers. The platinum compounds of the present invention have high solubility in water, low toxicity and strong antitumor effect.

12 Claims, No Drawings

(56) References Cited

FOREIGN PATENT DOCUMENTS

| WO | 9954319 | 10/1999 |
|----|---------|---------|
| WO | 9954330 | 10/1999 |
| WO | 9965913 | 12/1999 |
| WO | 9967252 | 12/1999 |
| WO | 9967253 A2 | 12/1999 |
| WO | 0000485 | 1/2000 |
| WO | 2006091790 A1 | 8/2006 |

OTHER PUBLICATIONS

Osol A. [Editor]. "Chapter 27: Structure-activity relationship and drug design." Remington's Pharmaceutical Sciences (Sixteenth Edition). Mack Publishing. 1980. pp. 420-425.*
Martin et al. "Do structurally similar molecules have similar biological activity?" Journal of Medicinal Chemistry, 2002; 45: 4350-4358.*
Lippard SJ. "The Art of Chemistry." Nature. 2002. 416-587.*
Dorwald FZ. "Side reactions in organic synthesis: a guide to successful design." Wiley VCH Verlag GmbH & Co. KGaA. 2005. pp. 1-15.*
Caron, Giulia et al., The relevance of polar surface area (PSA) in rationalizing biological properties of several cis-diamminemalonatoplatinum (II) derivatives, ChemMedChem, Oct. 5, 2009 (Oct. 5, 2009), vol. 4, No. 10, pp. 1677 to 1685, especially compound 7 in figure 1 of p. 1678.
D Gibson et al., Anthraquinone intercalators as carrier molecules for second-generation platinum anticancer drugs, Eur J Med Chem, Oct. 1997, vol. 32, No. 10, pp. 823 to 831, especially complexes (8)-(12) in scheme 1 of p. 824, table III of p. 828.
International Search Report and Written Opinion for Application No. PCT/CN2013/001390 dated Feb. 27, 2014.
M.A. Jakuper et al., "Tumor-inhibiting platinum complexes-state of art and future perspectives", Rev. Physiol Biochem Pharmacal, 2003, 146, 1-53.
Kidani, Y., et al., Synthesis of Platinum (II) Complexes of 4-Substituted o-Phenylenediamine Derivatives and Determination of Their Antitumor Activity, Chem. Pharm. Bull., No. 11, 2577-2581, 1979.
Extended European Search Report for Application No. EP13855223.7 dated Aug. 31, 2016.

* cited by examiner

US 9,725,477 B2

PLATINUM COMPOUNDS OF MALONIC ACID DERIVATIVE HAVING LEAVING GROUP CONTAINING AMINO OR ALKYLAMINO

CROSS-REFERENCE TO RELATED APPLICATIONS

The present application is a national phase entry under 35 U.S.C. §371 of International Application No. PCT/CN2013/001390 filed Nov. 15, 2013, which claims priority from Chinese Application No. 201210466262.8 filed Nov. 17, 2012, all of which are hereby incorporated herein by reference.

FIELD OF THE INVENTION

The present invention relates to a platinum compound for anti-cell proliferative diseases, and in particular relates to a platinum compound of malonic acid derivatives having a leaving group containing an amino or alkylamino, a preparation method and use thereof.

BACKGROUND OF THE INVENTION

Cancers (malignant tumors) are one of the leading diseases threatening a human life today. The morbidity and mortality of the tumors have increased sharply in recent years, Tumor development trend revealed by the World Health Organization (WHO) indicates that the annual newly confirmed tumor patients in the world wide are more than 10,000,000 since 1996, the global total tumor patients had exceeded 40,000,000 by the end of 1999, and thus approximately 7,000,000 persons die of various tumors all over the world each year. In 2001, the morbidity and mortality of tumors in the world had increased by 22% as compared with that of 1990, tumors have been the second main cause of death just behind cardiovascular and cerebrovascular diseases, and the most common cancers are lung cancer, breast cancer, colorectal cancer, gastric cancer, liver cancer, cervical cancer, esophageal cancer, and bladder cancer. The authoritative survey data on the morbidity and mortality of various cancers in China in 2006 published on the tenth National Clinical Oncology Conference showed that the death toll of cancers was 3,000,000 in China in 2006, and there are approximately 2,120,000 newly confirmed cancer patients each year. In the mortality of malignant tumors, lung cancer ranks the first of the malignant tumors. Experts estimated that, by 2020, the death toll will exceed 4,000,000; by 2025, tumors will become the first major cause for the global death toll.

There are three means for clinically treating cancers, operation, radiotherapy and medical chemotherapy, antitumor drugs are the most commonly used therapy method, and the global market sale of antitumor drugs was 48 billion dollars in 2008. At present, clinical antitumor drugs are mainly classified into alkylating agent, antimetabolites, metal platinum, plant alkaloids and other natural drugs, cytotoxic antibiotics, etc. Platinum-based antitumor drugs were a sort of the most important antitumor drugs and were firstly developed in 1960s. The important differences from traditional cytotoxic antitumor drugs are an unique mechanism of action and an excellent antitumoral selectivity of platinum-based antitumor drug. Its main action target is DNA, which is cross-linked inter and intra DNA chains and forms platinum complex~DNA composite, to disturb DNA replication or combines with nucleoprotein and plasmosin, belonging to a cycle nonspecific agent. Cis-dichlorodiamminoplatinum i.e., Cisplatin, cis-1,1-cyclobutanedicarboxylatodiamminoplatinum, i.e., Carboplatin, cis-glycolato-diamminoplatinum i.e., Nedaplatin, oxalato-(trans-L-1, 2-cyclohexanediamine) platinum i.e., Oxaliplatin, cis-[(4R, 5R)-4,5-bis(aminomethyl)-2-isopropyl 1,3-dioxane](bidentate) platinum, i.e., Sunpla, and 1,2 diaminomethyl-cyclobutane-platinum lactate i.e., Lobaplatin etc. have been successfully developed in succession. Platinum-based antitumor drugs are characterized by a wide antitumor spectrum, a strong effect, etc. Moreover, the platinum-based antitumor drugs have a good synergistic effect with other antitumor drugs, which not only improves the inhabitation ratios of the existing tumors, but also expands the antitumor spectrum, thus consolidating the place of platinum-based antitumor drugs in clinical therapy. Hundreds of antitumor drugs were ranked by WHO in 1995, and cisplatin was ranked at the second place in comprehensive evaluations in terms of curative effects and markets. Statistical data indicates that, among all the chemotherapy schemes in China, 70%-80% are dominated by platinum or formulated with platinum-based drugs.

However, platinum-based antitumor drugs now have disadvantages of high toxicity such as myelosuppression, nephrotoxicity, nerve injury, etc., poor solubility, relatively narrow anticancer spectrum, and drug resistance, etc. Therefore, design and synthesis of new platinum-based antitumor drugs are now still one of the leading directions for the anticancer drugs research (M. A. Jakuper, M. Galanski, B. K. Keppler. Tumor-inhibiting platinum complexes-state of art and future perspectives, Rev. Physiol Biochem Pharmacol, 2003, 146, 1-53).

In recent two years, considerable studies have been conducted in order to reduce the toxic and side effects of platinum-based chemotherapy drugs, improve curative effects, reduce tumor recurrence and avoid to cause drug resistance, and improve the water solubility of the platinum compound. For example, the solubility of cisplatin is 2.65 mg/ml, the solubility of the followed Oxaliplatin is 7.9 mg/ml; the solubility of Carboplatin is 17.8 mg/ml; the solubility of Minoplatin is 27 mg/ml, and the toxic and side effects of Oxaliplatin and Carboplatin and the like are reduced as compared with those of cisplatin, the deficiency is that the solubility of the above so-called water-soluble platinum compound remains slightly soluble or sparingly soluble. Murray A. Plan et al prepared a sodium alcoholate salt for platinum compound, which effectively improved the solubility in vitro (U.S. Pat. No. 4,322,362A), but the compound must be just dissolved at pH of 10 or more and the toxicity problem was still not effectively solved. Giulia C et al also prepared a series of platinum compounds, however, the solubility of these compounds was still not remarkably improved (Chem Med Chem, 2009, 4(10), 1677-1685). WO2006091790A1 also disclosed a series of platinum compounds having specific structures, but similarly, the solubility problem and toxicity problem were still not successfully improved.

SUMMARY OF THE INVENTION

The present invention provides a platinum compound for treating proliferative diseases, in particular a platinum compound of malonic acid derivatives having a leaving group containing amino or alkylamino in the structure of the compound, a pharmaceutical acceptable salt, solvate, stereoisomer or prodrug thereof, and as compared with the existing antitumor platinum compounds, the solubility of the platinum compound of the invention has been greatly improved, and the toxic and side effects have been significantly reduced, thereby achieving a good technical effect. The structure of such compound is shown by formula A:

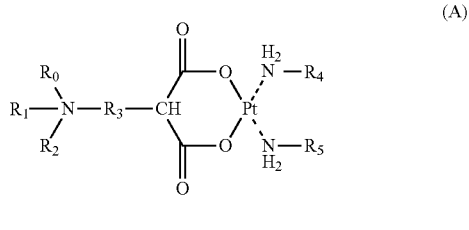

(A)

Wherein:

$R_0$ may be present or absent, when being present, $R_0$ is selected from alkyl, cycloalkyl, alkoxyalkyl, alkylaminoalkyl, heterocyclyl, alkenyl, alkynyl, which may be unsubstituted, or optionally substituted by halogen, hydroxyl, alkoxy, alkyl, alkoxyalkyl, cycloalkyl, heterocyclyl, aryl, provided that if $R_0$ contains an unsaturated bond(s), atoms of the unsaturated bond cannot be directly linked with nitrogen atom, and then the formula A is a quaternary ammonium base; and when $R_0$ is absent, the formula A is a tertiary amine base.

$R_1$ and $R_2$ may be same or different, and are selected from hydrogen, alkyl, cycloalkyl, alkoxyalkyl, alkylaminoalkyl, heterocyclyl, alkenyl, alkynyl, which may be unsubstituted, or optionally substituted by halogen, hydroxyl, alkoxy, alkyl, alkoxyalkyl, cycloalkyl, heterocyclyl, aryl, provided that if $R_1$ or $R_2$ contains an unsaturated bond(s), atoms of the unsaturated bond cannot be directly linked with nitrogen atom.

$R_1$, $R_2$ and the linked nitrogen atom therewith may further together form a closed, saturated or unsaturated heterocyclic ring which may be, for example, three-membered, four-membered, five-membered, six-membered, seven-membered or eight-membered ring; the ring may further be optionally fused with other rings, and may be optionally substituted by halogen, hydroxyl, alkoxy, alkyl, alkoxyalkyl, cycloalkyl, heterocyclyl, aryl, provided that an atom linked with said nitrogen atom must be a saturated carbon atom.

$R_3$ is $C_4$ linear alkyl or $C_4$ cycloalkyl, which may be optionally substituted by one or more of alkoxy, hydroxyl, alkyl, halogen, haloalkyl, alkoxyalkyl, heterocyclyl; wherein, said alkoxy includes, but not limited to, methoxyl, ethyoxyl, propoxy, isopropoxy, said alkyl includes, but not limited to, methyl, ethyl, isopropyl.

$R_4$ and $R_5$ may be same or different, and may be, but not limited to, hydrogen, hydroxyl, alkyl, cycloalkyl, alkoxy, alkoxyalkyl, heterocyclyl, alkenyl, alkynyl; the alkyl, alkenyl, alkynyl, cycloalkyl, alkoxyalkyl, alkylaminoalkyl, heterocyclyl may be unsubstituted or optionally substituted, preferably substituted by halogen, hydroxyl, alkoxy, linear or branched alkyl, alkoxyalkyl, cycloalkyl, heterocyclyl.

$R_4$, $R_5$ and the linked atom therewith may further together form a closed ring, which may be, for example, four-membered, five-membered, six-membered, seven-membered or eight-membered ring, the ring may further be optionally fused with other rings and may be optionally substituted.

Preferably, $R_0$ is absent or $R_0$ is selected from $C_{1-8}$ alkyl, cycloalkyl, alkoxyalkyl, alkylaminoalkyl, heterocyclyl; $R_1$ and $R_2$ are selected from hydrogen, $C_{1-8}$ alkyl, cycloalkyl, alkoxyalkyl, alkylaminoalkyl, heterocyclyl; $R_3$ may be, but not limited to, $C_4$ alkyl or $C_4$ cycloalkyl; $R_4$ and $R_5$ are selected from hydrogen, hydroxyl, $C_{1-8}$ alkyl, cycloalkyl, alkoxy, alkoxyalkyl, heterocyclyl.

More preferably, the present invention provides a compound of formula B and a pharmaceutically acceptable salt thereof:

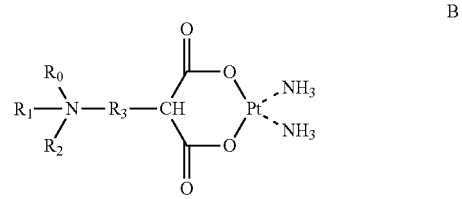

B wherein $R_0$, $R_1$, $R_2$, $R_3$ are as described above.

Most preferably, $R_0$ is absent, and $R_1$ and $R_2$ are hydrogen, methyl, ethyl propyl, or $R_1$, $R_2$ and N together form a heterocycle, for example, four-membered, five-membered, six-membered or seven-membered N-containing heterocycle which is saturated or contains a unsaturated bond(s), and $R_3$ is butyl or cyclobutyl.

The present invention further provides a platinum compound of formula C and a pharmaceutically acceptable salt, solvate, isomer or prodrug thereof, i.e., the compound which is obtained when $R_4$ and $R_5$ and the linked atom therewith together form a closed ring, the structural formula is as follows:

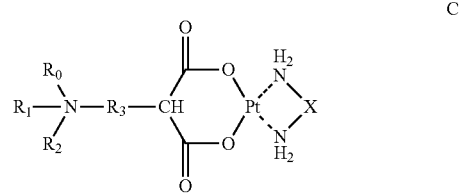

C

Wherein, the groups from which $R_1$, $R_2$, $R_3$ are selected are as described above,

is preferable, but not limited to:

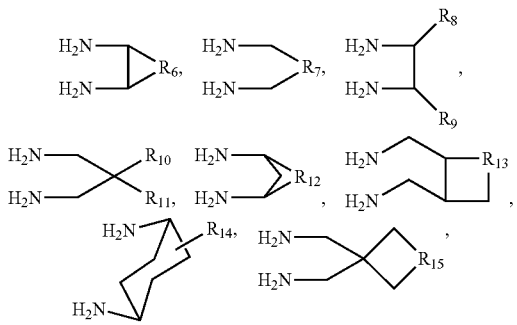

which may further be optionally linked with various suitable substituents.

In the platinum compound of formula C, $R_6$ may be, but not limited to, $(CH_2)_n$, wherein n=1 to 6, preferably 3 to 5, most preferably 4, in which some —$CH_2$— may be substituted by —O—, and one or more hydrogens of $(CH_2)_n$ may be substituted by halogen, alkyl, hydroxyl or alkoxy, heterocyclyl, and the like; the preferred compounds are (±) trans-1, 2-hexane, pentane, butane and propanediamine platinum (II);

$R_7$ may be, but not limited to, $(CH_2)_n$, wherein n=0 to 3, preferably n=0 to 2, in which some —$CH_2$— may be substituted by —O—, and one or more hydrogens of $(CH_2)$— may be substituted by halogen, alkyl, hydroxyl, hydroxyalkyl or alkoxy, and the like;

$R_8$ and $R_9$ may be, but not limited to, hydrogen, halogen, hydroxyl, hydroxyalkyl, alkyl, alkoxy, heterocyclyl, and the like; and $R_8$ and $R_9$ may be same or different, preferably hydroxymethyl (F);

$R_{10}$ and $R_{11}$ may be, but not limited to, hydrogen, halogen, hydroxyalkyl, alkyl, alkoxy, heterocyclyl, and the like; and $R_{10}$ and $R_{11}$ may be same or different, preferably hydroxymethyl; $R_{12}$ may be, but not limited to, $(CH_2)_n$, wherein n=2 to 4; in which some —$CH_2$— may be substituted by —O—, and one or more hydrogens of $(CH_2)$— may be substituted by halogen, alkyl, hydroxyl, or alkoxy, and the like;

$R_{13}$ may be —$CH_2$— or —O—, preferably —$CH_2$—;

$R_{14}$ may be hydrogen, halogen, alkyl, alkoxy, hydroxyalkyl or hydroxyl; and preferably, $R_{14}$ is hydrogen;

$R_{15}$ may be, but not limited to, —$CH_2$—O— or —O—, $(CH_2)_n$, wherein n=1 to 3, in which one or more hydrogens of $(CH_2)$— may be substituted by alkyl, alkoxy, hydroxyl, or hydroxyalkyl, and the like; and preferably, $R_{15}$ is —$CH_2$—O—$CH_2$—.

Preferably, base structures of the compound are as follows:

(D1)
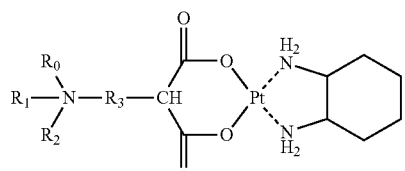

(D2)
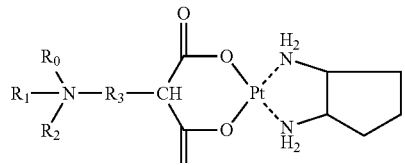

(D3)
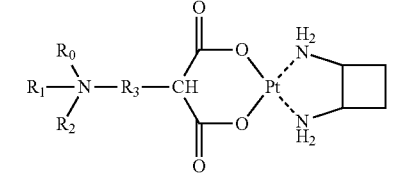

(D4)
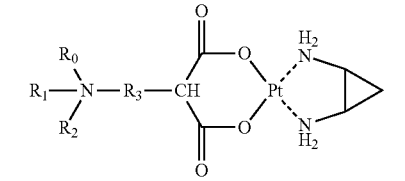

(E1)
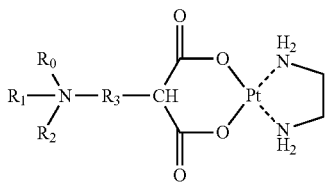

(E2)
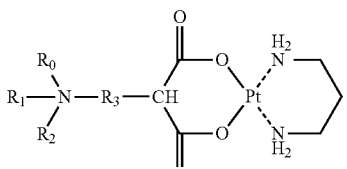

(E3)
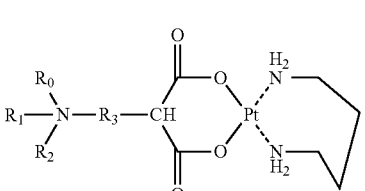

(F)
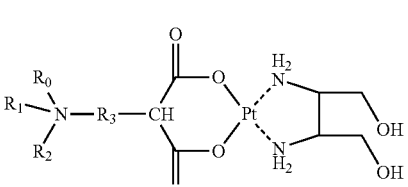

(G)
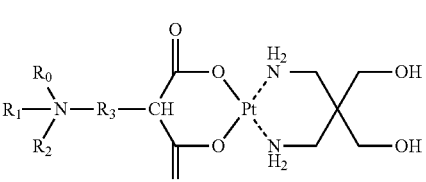

(H)
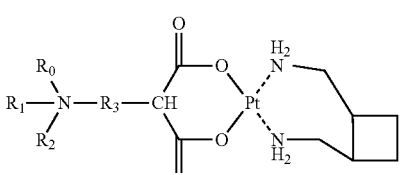

(I)
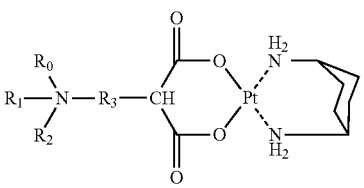

(J)
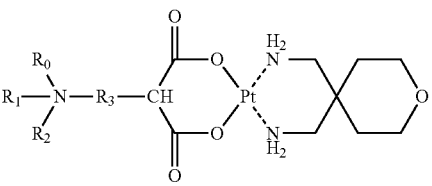

The most preferred compounds of the present invention include:
compound 1: 2-(4-diethylaminobutyl)-malonate•cis-diamine platinum (II) acetate;

compound 2: 2-(4-diethylaminobutyl)-malonate•cis-(1,2-ethylenediamine) platinum (II) tosilate;
compound 3: 2-(4-diethylaminobutyl)-malonate•cis-(1,2-trans-cyclohexanediamine) platinum (II) tosilate;
compound 4: 2-(4-(1-piperidyl)-butyl)-malonate•cis-diamine platinum (II) phosphate;
compound 5: 2-(4-(1-tetrahydropyrrolidinyl)-butyl)-malonate•cis-diamine platinum (II) phosphate;
compound 6: 2-(3-dimethylaminocyclobutyl)-malonate•cis-diamine platinum (II) mesylate;
compound 7: 2-(4-di-n-propylaminobutyl)-malonate•cis-diamine platinum (II) phosphate;
compound 8: 2-(3-methyl-4-diethylaminobutyl)-malonate•cis-diamine platinum (II) acetate;
compound 9: 2-(4-(1-piperidyl)-butyl)-malonate•cis-(1,2-trans-cyclohexanediamine) platinum (II) tosilate;
compound 10: 2-(4-(2-methyl-1-tetrahydropyrrolidinyl)-butyl)-malonate•cis-diamine platinum (II) phosphate;
compound 11: 2-(4-aminobutyl)-malonate•cis-(1,2-trans-cyclohexanediamine) platinum (II) phosphate;
compound 12: 2-(4-ethylaminobutyl)-malonate•cis-(1,2-trans-cyclohexanediamine) platinum (II) phosphate;
Compound 13: 2-(4-N-methyl-isopropylaminobutyl)-malonate•cis-diamine platinum (II) acetate;
compound 14: 2-(4-diethylaminobutyl)-malonate•cis-(1,2-trans-cyclopentanediamine) platinum (II) phosphate;
compound 15: 2-(4-diethylaminobutyl)-malonate•cis-(1,2-trans-cyclobutanediamine) platinum (II) succinate;
compound 16: 2-(4-diethylaminobutyl)-malonate•cis-(1,2-trans-cyclopropanediamine) platinum (II) phosphate;
compound 17: 2-(4-diethylaminobutyl)-malonate•cis-(1,2-ethylenediamine) platinum (II) tosilate;
compound 18: 2-(4-diethylaminobutyl)-malonate•cis-(1,3-propanediamine) platinum (II) phosphate;
compound 19: 2-(4-diethylaminobutyl)-malonate•cis-(1,4-butanediamine) platinum (II) phosphate;
compound 20: 2-(2-diethylaminobutyl)-malonate•cis-1,2-(1,2-dihydroxymethyl)-ethylenediamine platinum (II) phosphate;
compound 21: 2-(4-diethylaminobutyl)-malonate•cis-1,3-(2,2-hydroxymethyl)-propanediamine platinum (II) phosphate;
compound 22: 2-(4-diethylaminobutyl)-malonate•cis-1,4-(trans-2, 3-cyclobutyl)-butanediamine platinum (II) phosphate;
compound 23: 2-(4-diethylaminobutyl)-malonate•cis-(1,4-cyclohexyldiamine) platinum (II) phosphate;
compound 24: 2-(4-diethylaminobutyl)-malonate•cis-1,3-(2,2-(4-oxacyclohexyl))-propanediamine platinum (II) phosphate;
compound 25: 2-(4-diethylaminobutyl)-malonate•cis-dicyclopentylamine platinum (II) acetate;
compound 26: 2-(4-diethylaminobutyl)-malonate•cis-•ammonia•cyclopentylamine platinum (II) acetate;
compound 27: 2-(4-diethylaminobutyl)-malonate•cis-•(2-aminomethyl-cyclopentylamine) platinum (II) acetate;
compound 28: 2-(4-diethylaminobutyl)-malonate•cis-•ammonia•piperidine platinum (II) acetate;
compound 29: 2-(4-trimethylaminobutyl)-malonate•cis-(1, 2-trans-cyclohexanediamine) platinum (II) tosilate.

The following are the definitions of various terms for use in the description of the present invention. Unless otherwise specifically defined, the following terms are suitable for use in the entire specification and claims (independently or as a part of large groups).

The term "alkyl" refers to a linear or branched, saturated monovalent hydrocarbyl, specifically, alkyl refers to a linear, saturated, monovalent hydrocarbyl having 1-20 ($C_{1-20}$), 1-15 ($C_{1-15}$), 1-10 ($C_{1-10}$), 1-7 ($C_{1-7}$) or 1-4 ($C_{1-4}$) carbon atoms, or a branched, saturated monovalent hydrocarbyl having 3-20 ($C_{3-20}$), 3-15 ($C_{3-15}$), 3-10 ($C_{3-10}$), 3-7 ($C_{3-7}$) or 3-4 ($C_{3-4}$) carbon atoms. The examples of alkyl include, but not limited to, methyl, ethyl, n-propyl, isopropyl, n-butyl, isobutyl, sec-butyl, tert-butyl, pentyl (including all isomer forms), hexyl (including all isomer forms), heptyl (including all isomer forms), octyl (including all isomer forms), nonyl (including all isomer forms), decyl (including all isomer forms), hendecyl (including all isomer forms), dodecyl (including all isomer forms), tridecyl (including all isomer forms), tetradecyl (including all isomer forms), pentadecyl (including all isomer forms), hexadecyl (including all isomer forms), heptadecyl (including all isomer forms), octadecyl (including all isomer forms), nonadecyl (including all isomer forms) and eicosyl (including all isomer forms). For example, $C_{1-7}$ alkyl refers to a linear, saturated monovalent hydrocarbyl having 1-7 carbon atoms or a branched, saturated monovalent hydrocarbyl having 3-7 carbon atoms.

"Alkyl" may be optionally substituted by one, two, three or four of the following substituents: such as, halogen, trifluoromethyl, trifluoromethoxyl, hydroxyl, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, substituted tertiary amine (wherein, 2 nitrogen substituents are selected from alkyl, aryl or aralkyl); alkanoylamino, aroylamino, arylalkanoylamino, substituted alkanoylamino, substituted arylamino, substituted arylalkanoyl, thiohydroxyl, alkylsulfanyl, arylsulfanyl, aralkylsulfanyl, cycloalkylsulfanyl, heterocyclosulfanyl, alkylthiocarbonyl, arylthiocarbonyl, aralkylthiocarbonyl, alkylsulfonyl, arylsulfonyl, aralkylsulfonyl, sulfinylamino(e.g., $SO_2NH_2$), substituted sulfinylamino, nitro, cyano, carboxyl, carbamyl (e.g., $CONH_2$), substituted carbamyl (e.g., CONH alkyl, CONH aryl, CONH aralkyl or the substituents are selected from alkyl, aryl or aralkyl with two substituents on N); alkoxycarbonyl, aryl, substituted aryl, guanidyl and heterocyclyl (e.g., indolyl, imidazolyl, furyl, thienyl, thiazolyl, pyrrolidyl, pyridyl, pyrimidyl, etc.). The above substituents may be further substituted by halogen, alkyl, alkoxy, aryl or aralkyl.

The term "alkoxy" refers to a group generated by linking a linear, saturated mono valent hydrocarbyl having 1-20 ($C_{1-20}$), 1-15 ($C_{1-15}$), 1-10 ($C_{1-10}$), 1-7 ($C_{1-7}$) or 1-4 ($C_{1-4}$) carbon atoms or a branched, saturated monovalent hydrocarbyl having 3-20 ($C_{3-20}$), 3-15 ($C_{3-15}$), 3-10 ($C_{3-10}$), 3-7 ($C_{3-7}$) or 3-4 ($C_{3-4}$) carbon atoms with an oxygen atom. The examples of alkoxy include, but not limited to, methoxyl, ethoxyl, propoxy, isopropoxy, n-butoxy, isobutoxy, sec-butoxy, tert-butoxy, pentyloxy (including all isomer forms), hexyloxy (including all isomer forms), heptyloxy (including all isomer forms), octyloxy (including all isomer forms), nonyloxy (including all isomer forms), decyloxy (including all isomer forms), undecyloxy (including all isomer forms), dodecyloxy (including all isomer forms), tridecyloxy (including all isomer forms), tetradecyloxy (including all isomer forms), pentadecyloxy (including all isomer forms), hexadecyloxy (including all isomer forms), heptadecyloxy (including all isomer forms), octadecyloxy (including all isomer forms), nonadecyloxy (including all isomer forms) and eicosyloxy (including all isomer forms). The term "alkylamino" refers to a group in which one or two H in —$NH_2$ are substituted by a linear alkyl having 1-10 ($C_{1-10}$), 1-6 ($C_{1-6}$) or 1-4 ($C_{1-4}$) carbon atoms or a branched alkyl having 3-10 ($C_{3-10}$), 3-6 ($C_{3-6}$) or 3-4 ($C_{3-4}$) carbon atoms, respectively; when the two H are substituted at the same time, the substituents may be same or different. The examples of alkylamino include, but not limited to, methylamino, dimethylamino, ethylamino, diethylamino, propylamino, dipropylamino, isopropylamino, diisopropylamide, n-butylamino, iso-butylamino, tert-butylamino, di-n-butylamino, di-iso-butylamino, di-tert-butylamino, pentylamino, dipentylamine, hexylamino, dihexylamino, heptylamino, diheptylamino, octylamino, dioctylamino, nonylamino, dinonylamino, decylamino, didecylamino, N-methyl-N-ethylamino, N-methyl-N-propylamino, N-methyl-N-isopropylamino, N-methyl-N-butylamino, N-methyl-N-isobutylamino, N-methyl-N-tertbutylamino, N-methyl-N-pentylamino, N-methyl-N-hexylamino, N-methyl-N-heptylamino, N-methyl-N-octylamino, N-methyl-N-nonylamino, N-methyl-N-decylamino, N-ethyl-N-propylamino, N-ethyl-N-isopropylamino, N-ethyl-N-butylamino, N-ethyl-N-isobutylamino, N-ethyl-N-tertbutylamino, N-ethyl-N-pentylamino, N-ethyl-N-hexylamino, N-ethyl-N-heptylamino, N-ethyl-N-octylamino, N-ethyl-N-nonylamino, N-ethyl-N-decylamino, N-propyl-N-isopropylamino, N-propyl-N-butylamino, N-propyl-N-isobutylamino, N-propyl-N-tertbutylamino, N-propyl-N-pentylamino, N-propyl-N-hexylamino, N-propyl-N-heptylamino, N-propyl-N-octylamino, N-propyl-N-nonylamino, N-propyl-N-decylamino, N-isopropyl-N-butylamino, N-isopropyl-N-isobutylamino, N-isopropyl-N-tertbutylamino, N-isopropyl-N-pentylamino, N-isopropyl-N-hexylamino, N-isopropyl-N-heptylamino, N-isopropyl-N-octylamino, N-isopropyl-N-nonylamino, N-isopropyl-N-decylamino, N-butyl-N-isobutylamino, N-butyl-N-tertbutylamino, N-butyl-N-pentylamino, N-butyl-N-hexylamino, N-butyl-N-heptylamino, N-butyl-N-octylamino, N-butyl-N-nonylamino, N-butyl-N-decylamino, N-isobutyl-N-tertbutylamino, N-isobutyl-N-pentylamino, N-isobutyl-N-hexylamino, N-isobutyl-N-heptylamino, N-isobutyl-N-octylamino, N-isobutyl-N-nonylamino, N-isobutyl-N-decylamino, N-tertbutyl-N-pentylamino, N-tertbutyl-N-hexylamino, N-tertbutyl-N-heptylamino, N-tertbutyl-N-octylamino, N-tertbutyl-N-nonylamino, N-tertbutyl-N-decylamino, N-pentyl-N-hexylamino, N-pentyl-N-heptylamino, N-pentyl-N-octylamino, N-pentyl-N-nonylamino, N-pentyl-N-decylamino, N-hexyl-N-heptylamino, N-hexyl-N-octylamino, N-hexyl-N-nonylamino, N-hexyl-N-decylamino, N-heptyl-N-octylamino, N-heptyl-N-nonylamino, N-heptyl-N-decylamino, N-octyl-N-nonylamino, N-octyl-N-decylamino, N-nonyl-N-decylamino, and all isomer forms of the above amines, and the like.

The term "halogen" or "halo" refers to fluorine, chlorine, bromine, and iodine.

The term "aryl" refers to a monocyclic or dicyclic aromatic hydrocarbyl having 6-12 carbon atoms, such as phenyl, naphthyl, biphenyl and diphenyl, each of which may be substituted.

"Aryl" may be optionally substituted by the following substituents, such as alkyl, halogen, trifluoromethoxy, trifluoromethyl, hydroxyl, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiohydroxyl, alkylthio, cycloalkylthio, heterocyclothio, carbamido, nitro, cyano, carboxyl, carboxylalkyl, formamyl, alkoxycarbonyl, alkylthiocarbonyl, arylthiocarbonyl, alkylsulfonyl, sulfinylamino, aryloxy, etc. Said substituents may further be substituted by halogen, hydroxyl, alkyl, alkoxy, or aryl.

The term "aralkyl" refers to a group in which an aryl is directly linked with an alkyl, such as benzyl, phenethyl and phenylpropyl.

The term "alkenyl" refers to a linear or branched hydrocarbyl group having one, two, three or four double bonds, containing 2-20 carbon atoms, preferably 2-15 carbon atoms, most preferably 2-8 carbon atoms and includes, but not limited to, ethenyl, n-propenyl, isopropenyl, n-2-butylene, and n-3-hexyne, the term "alkenyl" also includes a group having "cis-configuration" and "trans-configuration" or "E" and "Z" configurations, and those skilled in the art may understand this.

"Alkenyl" may be optionally substituted by the following substituents, such as halogen, hydroxyl, alkoxy, alkanoyl, alkanoyloxy, amino, alkylamino, dialkylamino, alkanoylamino, thiohydroxyl, alkylthio, alkylthiocarbonyl, alkylsulfonyl, sulfinylamino, nitro, cyano, carboxyl, formamyl, substituted formamyl, guanidyl and heterocyclyl group, such as indolyl, imidazolyl, furyl, thienyl, thiazolyl, pyrrolidyl, pyridyl, pyrimidyl, etc.

The term "alkynyl" or "chain alkynyl" refers to a linear or branched hydrocarbyl group having 1-4 triple bonds, containing 2-20 carbon atoms, preferably 2-15 carbon atoms, most preferably 2-8 carbon atoms, and includes, but not limited to, ethynyl, n-propinyl, n-2-butyne, n-3-hexyne, etc.

"Alkenyl" may be optionally substituted by the following substituents: halogen, hydroxyl, alkoxy, alkanoyl, alkanoyloxy, amino, alkylamino, dialkylamino, alkanoylamino, thiohydroxyl, alkylthio, alkylthiocarbonyl, alkylsulfonyl, sulfinylamino, nitro, cyano, carboxyl, formamyl, substituted formamyl, guanidyl and heterocyclyl, such as imidazolyl, furyl, thienyl, thiazolyl, pyrrolidyl, pyridyl, pyrimidyl, etc.

The term "cycloalkyl" refers to an optionally substituted, saturated cyclic hydrocarbon ring system which preferably contains 1-3 rings and each of the rings (which may be further fused with unsaturated $C_3$-$C_7$ carbocycle) contains 3-7 carbon atoms. Exemplified groups include cyclopropyl, cyclobutyl, cyclopentyl, cyclohexyl, cycloheptyl, cyclooctyl, cyclodecyl, cyclododecyl and adamantyl. Exemplified substituents include one or more of alkyl groups as described above, or one or more of alkyl substituents as described above.

The terms "heterocycle", "heterocyclic" and "heterocyclyl" refer to an optionally substituted, completely saturated or incompletely saturated, aromatic or non-aromatic ring group, for example, said ring is a 4-7-membered monocycle, 7-11-membered dicycle or 10-15-membered tricycle system, which contains at least one heteroatom on the ring containing at least one carbon atom. Each ring of heterocyclic group containing a heteroatom may have 1, 2, 3 or 4 heteroatoms selected from nitrogen, oxygen and sulphur atom, wherein said nitrogen and sulphur heteroatom may also be optionally oxidized and nitrogen heteroatom may also be optionally quaternary ammoniated. Said heterocyclic group may be linked on any of heteroatoms or carbon atoms.

Exemplified monocyclic heterocyclic groups include pyrrolidyl, pyrryl, indolyl, pyrazolyl, oxacyclobutyl, pyrazolinyl, imidazolyl, imidazolinyl, imidazolidinyl, oxazolyl, oxazolidinyl, isooxazolinyl, isooxazolyl, thiazolyl, thiadiazolyl, thiazolidinyl, isothiazolyl, isothiazolidinyl, furyl, tetrahydrofuryl, thienyl, oxadiazolyl, piperidyl, piperazinyl, 2-oxo-piperazinyl, 2-oxo-piperidyl, 2-oxo-pyrrolidyl, 2-oxo-azepinyl, azepinyl, 4-piperidonyl, pyridyl, N-oxopyridyl, pyrazinyl, pyrimidyl, pyridazinyl, tetrahydrothiopyranyl, tetrahydropyranyl, morpholinyl, thiamorpholinyl, thiamorpholine sulfoxide, tetrahydrothiopyran sulfoxide, thiamorpholinyl sulfoxide, 1, 3-dioxolame and tetralin-1,1- dioxo thienyl, dioxane, isothiazolidinyl, thia cyclobutyl, thia cyclopropyl, triazinyl and triazolyl, etc.

Exemplified bicyclic heterocyclic groups include benzothiazolyl, benzoxazolyl, benzothiophenyl, quinuclidinyl, quinolyl, quinolyl-N-oxide, tetrahydroisoquinolyl, isoquinolyl, benzimidazolyl, benzopyranyl, indolizinyl, benzopyranyl, chromonyl, coumarinyl, 1,2-phthalazinyl, quinoxalinyl, indazolyl, pyrrolopyridyl, furanopyridyl (e.g., furano[2,3-c]pyridyl, furano[3,1-b]pyridyl or furano[2,3-b]pyridyl), dihydroisoindolyl, dihydroquinazolinyl (e.g., 3,4-dihydro-4-oxo-quinazolinyl), benzisothiazol, benzisoxazole, benzodiazinyl, benzofuryl, benzothiopyranyl, benzotriazolyl, benzopyrazolyl, dihydrobenzofuryl, dihydrobenzothienyl, dihydrobenzothiopyranyl, dihydrobenzothiopyranyl sulphone, dihydrobenzopyranyl, dihydroindolyl, iso-benzodihydropyranyl, iso-indolinyl, 1,5-phthalazinyl, 2,3-phthalazinyl, 3,4-methylenedioxybenzyl, purinyl, pyridinopyridyl, quinazolinyl, tetrahydroquinolyl, thienofuryl, thienopyridyl, thienothienyl, etc.

Smaller heterocycles, such as an epoxide and an aziridine, are also included.

The term "heteroatom" includes oxygen, sulphur and nitrogen.

The term "a pharmaceutically acceptable salt" includes a salt of an active compound prepared using relatively non-toxic acid or base on the basis of a specific substituent presented on the compounds as described in the present invention. When the compound of the present invention contains a relatively acidic functional group, an alkali addition salt may be obtained by contacting this compound in the neutral form with sufficient required base, directly or in an appropriate inert solvent. Examples of a salt derived from a pharmaceutical acceptable inorganic base include aluminum, ammonium, calcium, copper, trivalent iron, ferrous, lithium, magnesium, manganese, bivalent manganese, potassium, sodium, zinc, etc. A salt derived from a pharmaceutical acceptable organic base includes salts of primary, secondary and tertiary amine, they include substituented amine, cyclamine, natural amine, etc., such as arginine, glycine betaine, caffeine, choline, N, N'-dibenzyl ethylenediamine, diethylamine, 2-diethylaminoethanol, 2-dimethylaminoethanol, ethanolamine, ethylenediamine, N-ethylmorpholine, N-ethylpiperidine, glucosamine, glucamine, histidine, hydrabamine, isopropamide, lysine, methylglucamine, morpholine, piperazine, piperidine, polyamino resin, procaine, purine, theobromine, triethylamine, trimethylamine, tripropylamine, tromethamine, etc. When the compound of the prevent invention contains a relatively alkali functional group, an acid addition salt may be obtained by contacting this compound in the neutral form with sufficient required acid, directly or in an appropriate inert solvent. Examples of a pharmaceutical acceptable acid addition salt include the salts derived from an inorganic acid which is, for example, nitrate, carbonate, bicarbonate, phosphate, hydrophosphate, dihydric phosphate, sulphate, bisulfate, phosphite, hydrochloride, hydrobromide, hydriodate, etc.; a salt derived from a relative nontoxic organic acid which is, for example, acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, etc.; and also includes a salt of amino acid such as, arginine and a salt of an organic acid such as, glucuronic acid or galactonic acid. Nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactonic acid salt are preferred.

In some embodiments provided in the present invention, the leaving group of the compound of the present invention contains a basic group(s) that may form a salt with an acid and a salt of a platinum (II) complex may be prepared using a method well-known to those skilled in the art. For example, it may form mesylate, trifluoromethanesulfonic salt with lower alkyl sulfonic acid, such as methanesulfonic acid, trifluoromethanesulfonic acid, etc.; form tosilate, benzene sulfonate, camphosulfonate with aryl sulfonic acid, such as benzene sulfonic acid or p-toluenesulfonic acid, etc; form a corresponding salt with an organic carboxylic acid, such as acetic acid, fumaric acid, tartaric acid, oxalic acid, maleic acid, malic acid, succinic acid, lactic acid or citric acid, etc.; form glutamate or aspartate with amino acid, such as glutamic acid or aspartic acid; and also form a corresponding salt with an inorganic acid, such as nitric acid, carbonic acid, sulfuric acid or phosphoric acid, etc. The acid that may be used includes an organic acid, an inorganic acid, etc.

The compound of the present invention may be interconverted with its salt form by a conventional method in the art, for example, a free compound may be obtained by contacting the salt with the base or acid and then separating by a conventional way, and its salt form may further be obtained by adding the compound into the acid or base and then separating by a conventional way. Some physical properties of the free compound, such as the solubility in a polar solvent, are different from those of various salt forms; however, for the purpose of the present invention, the salt and the compound in parent form have the same antitumor effect.

In addition to the salt form, the present invention provides a compound in the form of prodrug ester. The "prodrugs" of the compound as described in the present invention refer to those compounds which are prone to chemically change in a physiological environment to obtain the compound of the present invention. In addition, the prodrug may be converted into the compound of the present invention by a chemical or biochemical method in an environment in vitro. For example, when being placed in a reservoir of a transdermal patch containing a suitable enzyme or a chemical reagent, the prodrug may be slowly converted into the compound of the present invention. The prodrug is usually a pharmacologically inert compound before being converted into an active drug; however, this situation is not necessary. Usually, a functional group released by conversion (e.g., pyrolyzing under a specific operating condition) may be formed by masking a functional group required by a possible active moiety in a drug with "precursor group" (as defined below), thereby obtaining a "precursor moiety" of an active drug, and obtaining the prodrug. The precursor moiety may be catalyzed or induced by, for example, hydrolysis reaction, or by another actor (e.g., enzyme, light, acid or base) or the change of physical or environmental parameters (e.g., the change of temperature) or exposing in the physical or environmental parameters, to perform a spontaneous pyrolyzing. The actor may be endogenic with respect to the operating environment, for example, the enzyme existed in the cell where prodrug is given or an acidic environment of gastro or provided from external source. "Precursor" refers to a sort of protective group that may convert a drug into a prodrug when the functional group for masking the active drug forms the "precursor moiety". The precursor group is usually linked with the functional group of the drug by a bond which may be pyrolyzed in the specific condition. Therefore, the precursor group is a part of the precursor moiety which is pyrolyzed in the specific operating condition to release a functional group. As a specific example, the amide precursor part of formula —NH—C(O)CH$_3$ contains precursor group —C(O)CH$_3$.

It is well known in the art that a wide variety of precursor groups and the resulting precursors moiety which are suitable to mask the functional group in the active compound to obtain the prodrugs. For example, a hydroxyl functional group may be masked into a sulphonate, ester (e.g., acetate or maleate) or carbonate precursor moiety which may be hydrolyzed in vivo, to obtain a hydroxyl. An amino functional group may be masked into an amide, carbamate, imine, urea, phenylphosphino, phosphoryl or sulfenyl precursor moiety which may be hydrolyzed in vivo, to obtain an amino. A Carboxyl may be masked into an ester (including methyl, ethyl, neopentylacyloxymethyl, silicyl ester and thioester), amide or hydrazide precursor moiety which may be hydrolyzed in vivo to obtain a carboxyl. The present invention includes those esters and acyls known to change the solubility or hydrolysis properties in the art, to use as a sustained-release or prodrug formulation. For those skilled in the art, the specific examples of suitable precursor groups and their corresponding precursor moieties are apparent.

Some compounds of the present invention may exist in the forms of non-solvation and solvation including hydration form. "Solvate" refers to a complex generated from the combination of a solvent molecule with a molecule or ion of the solute. The solvent may be an organic compound, inorganic compound or the mixture of both. Some examples of the solvent include, but not limited to, methanol, N, N-dimethylformamide, tetrahydrofuran, dimethylsulfoxide, and water. Generally, the solvation form is equivalent to the non-solvation form and is included in the scope of the present invention. Some compounds of the present invention may exist in the form of polymorph or amorphism. In general, for the use envisaged by the present invention, all physical forms are the same and are included in the scope of the present invention.

Some compounds of the present invention have asymmetric carbon atoms (rotophore) or other chiral centers; and their racemes, non-enantiomers, geometric isomers, regional isomers and individual isomer (e.g., separated enantiomer) are included in the scope of the present invention. These isomers may be resolved or asymmetrically synthesized by a conventional method, to make isomer "optical pure", i.e., essentially containing no other isomers. For example, if a particular enantiomer of the compound of the present invention is required, it may be prepared by an asymmetric synthesis or derivatized with a chiral auxiliary, wherein the resulting mixture of diastereoisomer is separated and the auxiliary group is pyrolyzed to obtain a pure, desired enantiomer. Alternatively, when the molecule contains a basic functional group such as, an amino or an acidic functional group such as a carboxyl, an asymmetric isomerous salt is formed using an appropriate optical active acid or base, and then the diastereoisomers formed thereby are resolved by a well-known fractional crystallization or chromatographic process in the art, finally, a pure enantiomer is recovered.

The compound of the present invention may contain atomic isotopes in an abnormal proportion in one or more atoms constituting the compound. For example, the compound may be labelled with a radioisotope such as, tritium ($^3$H), iodine-125 ($^{125}$I) or carbon-14 ($^{14}$C). All isotope forms of the compound of the present invention are included in the scope of the present invention, whether they have radioactivity or not.

Another purpose of the present invention is to provide a method for preparing the foregoing compound.

I. The method for preparing formulae (A) and (B) (when R$_4$=R$_5$=NH$_3$, it is B, and in other situations, it is A) is as follows:

(1) adding potassium chloroplatinite into water and dissolving by stirring at room temperature, dissolving potassium iodide with water and then being added into the above potassium chloroplatinite solution to react under the condition of a water bath away from light with nitrogen charged;

(2) dissolving R$_4$NH$_2$ with water and then being dropped into the reaction solution obtained in step (1) to react under the water bath condition;

(3) cooling the reaction solution below room temperature, dissolving R$_5$NH$_2$ with water and then being dropped into the reaction solution obtained in step (2) to react in the water bath, with a quantity of yellow precipitate generated, cooling a temperature within the reaction solution below room temperature, and obtaining diiododiamine platinum (II) by suction filtration and washing;

(4) adding Ag$_2$SO$_4$ into water and stirring, adding the above diiododiamine platinum (II) into the reaction solution and then adding water, to react under the water bath condition away from light with nitrogen charged, and obtaining dihydrated diamine platinum (II)•sulfate by suction filtration;

(5) placing diethyl malonate and Br—R$_3$—Br into a flask, adding K$_2$CO$_3$ and tetrabutylammonium bromide and stirring, heating to react, removing the solid by suction filtration and washing, combining the filtrate, washing the organic layer and drying, and undergoing reduced pressure distillation of the solvent, to collect the distillate;

(6) placing diethyl 2-Br—R$_3$-malonate into a flask, adding anhydrous K$_2$CO$_3$ and acetonitrile, and stirring; adding R$_1$—NH—R$_2$ or R$_1$—N(R$_0$)—R$_2$ into the reaction solution, heating to react; and removing the insoluble substance by filtration, pumping out the filtrate, and then dissolving the filtrate by adding an organic solvent; washing with an aqueous solution, drying the organic layer, and pumping out the solvent under reduced pressure, to obtain a product; and purifying;

(7) placing the product obtained in step (6) into a flask, adding NaOH solution and stirring at room temperature; and (8) adjusting the product obtained in step (7) with an acid solution, then adding the product obtained in step (4), and heating to reac, to obtain the platinum compound of the present invention.

The preferred preparation method is as follows:

(1) adding potassium chloroplatinite into water and dissolving by stirring at room temperature, dissolving potassium iodide with water and then being added into the above potassium chloroplatinite solution to react in a water bath at 40~60° C. for 30~60 min with the protection of N$_2$ and away from light;

(2) dissolving R$_4$NH$_2$ with water and then being dropped into the reaction solution obtained in step (1) to react in the water bath at 40~60° C. for 30~60 min;

(3) cooling the reaction solution below 20° C., dissolving R$_5$NH$_2$ with water and then being dropped into the reaction solution obtained in step (2) to react in a water bath at 40~60° C. for 30~60 min, with a quantity of yellow precipitate generated, cooling a temperature within the reaction solution below 20° C., and obtaining diiododiamine platinum (II) by suction filtration and washing with water, absolute ethanol, ether in sequence;

(4) adding $Ag_2SO_4$ into water and stirring, adding the above diiododiamine platinum (II) into the reaction solution and then adding water, to react at 40~60° C. for 4~8 hours with the protection of $N_2$ and away from light, and obtaining dihydrated diamine platinum (II)•sulfate by suction filtration;

(5) placing diethyl malonate and Br—$R_3$—Br into a flask, adding $K_2CO_3$ and tetrabutylammonium bromide and stirring, heating to react in an oil bath, removing the solid by suction filtration and washing with ether, combining the filtrate, washing the organic layer with water and drying, and undergoing reduced pressure distillation of the solvent, to collect the distillate under a certain vacuum degree;

(6) placing diethyl Br—$R_3$-malonate into a three-necked flask, adding anhydrous $K_2CO_3$ and acetonitrile and stirring; adding $R_1$—NH—$R_2$ or $R_1$—N($R_0$)—$R_2$ into the reaction solution, heating to react in the oil bath, and removing the insoluble substance by filtration; pumping out the filtrate, and then dissolving the filtrate by adding ethyl acetate; washing with saturated NaCl aqueous solution, drying the organic layer, and pumping out the solvent by a water pump under reduced pressure; and purifying;

(7) placing the product obtained in step (6) into a flask, adding NaOH solution and stirring at room temperature; and (8) adjusting the product obtained in step (7) with an acid solution, then adding the product obtained in step (4), and heating to react, to obtain the compound of the present invention.

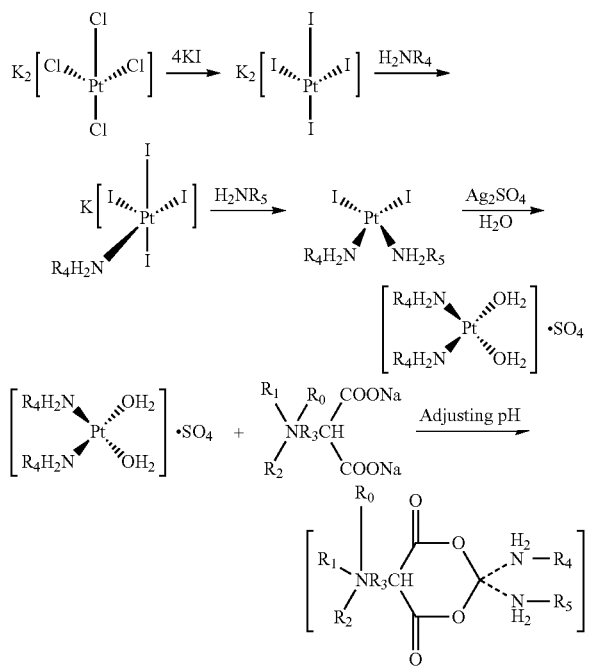

II. The method for preparing formula (C) is as follows:

(1) adding potassium chloroplatinite into water and dissolving by stirring at room temperature, dissolving potassium iodide with water and then being added into the above potassium chloroplatinite solution to react in a water bath condition away from light with nitrogen charged;

(2) dissolving bidentate ammonia $NH_2$—X—$NH_2$ with water and then being added into the reaction solution obtained in step (1) to react in the water bath, with a quantity of yellow precipitate generated; cooling a temperature within the reaction solution below room temperature, and obtaining bidentate diiododiamine platinum (II) by suction filtration and washing;

(3) adding $Ag_2SO_4$ into water and stirring, adding the above diiododiamine platinum (II) into the reaction solution and then adding water, to react under the condition of a water bath away from light with nitrogen charged, and obtaining dihydrated diamine platinum (II)•sulfate by suction filtration;

(4) placing diethyl malonate and Br—$R_3$—Br into a flask, adding $K_2CO_3$ and tetrabutylammonium bromide and stirring, heating to react, removing the solid by suction filtration and washing, combining the filtrate, washing the organic layer and drying, and undergoing reduced pressure distillation of the solvent, to collect the distillate;

(5) placing diethyl Br—$R_3$-malonate into a flask, adding anhydrous $K_2CO_3$ and acetonitrile, and stirring; adding $R_1$—NH—$R_2$ or $R_1$—N($R_0$)—$R_2$ into the reaction solution, heating to react, and removing the insoluble substance by filtration; pumping out the filtrate, and then dissolving the filtrate by adding an organic solvent; washing with an aqueous solution, drying the organic layer, and pumping out the solvent under reduced pressure, to obtain a product; and purifying;

(6) placing the product obtained in step (5) into a flask, adding NaOH solution and stirring at room temperature; and (7) adjusting the product obtained in step (6) with an acid solution, then adding the product obtained in step (3), and heating to react, to obtain the platinum compound of the present invention.

The Preferred preparation method is as follows:

(1) adding potassium chloroplatinite into water and dissolving by stirring at room temperature, dissolving potassium iodide with water and then being added into the above potassium chloroplatinite solution to react in a water bath at 40~60° C. for 30~60 min with the protection of $N_2$ and away from light;

(2) dissolving bidentate ammonia $NH_2$—X—$NH_2$ with water and then being added into the reaction solution obtained in step (1) to react in the water bath at 40~60° C. for 30~60 min, with a quantity of yellow precipitate generated; cooling a temperature within the reaction solution below 20° C., and obtaining bidentate diiododiamine platinum (II) by suction filtration and washing with water, absolute ethanol, ether in sequence;

(3) adding $Ag_2SO_4$ into water and stirring, adding the above diiododiamine platinum (II) into the reaction solution and then adding water, to react at 40~60° C. for 4~8 hours with the protection of $N_2$ and away from light, and obtaining dihydrated diamine platinum (II)•sulfate by suction filtration;

(4) placing diethyl malonate and Br—$R_3$—Br into a flask, adding $K_2CO_3$ and tetrabutylammonium bromide and stirring, heating to react in an oil bath, removing the solid by suction filtration and washing with ether, combining the filtrate, washing the organic layer with water and drying, and undergoing reduced pressure distillation of the solvent, to collect the distillate under a certain vacuum degree;

(5) placing diethyl Br—$R_3$-malonate into a three-necked flask, adding anhydrous $K_2CO_3$ and acetonitrile, and stirring; adding $R_1$—NH—$R_2$ or $R_1$—N($R_0$)—$R_2$ into the reaction solution, heating to react in the oil bath, and removing the insoluble substance by filtration; pumping out the filtrate, and then dissolving the filtrate by adding ethyl acetate; washing with saturated NaCl aqueous solution, drying the organic layer, and pumping out the solvent by a water pump under reduced pressure; and purifying;

(6) placing the product obtained in step (5) into a flask, adding NaOH solution and stirring at room temperature; and (7) adjusting the product obtained in step (6) with an acid solution, then adding the product obtained in step (3), and heating to react, to obtain the compound of the present invention.

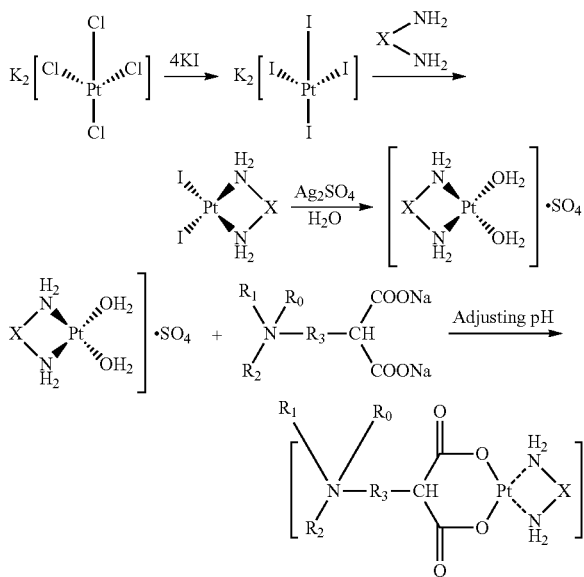

The present invention also provides a pharmaceutical composition containing the above compound, and a pharmaceutically acceptable salt, stereoisomer, prodrug or solvate thereof and a pharmaceutically acceptable carrier and/or excipient. The composition contains 0.01%-100%, preferably 0.1%-100%, more preferably 1%-100%, even more preferably 20%-100% (by weight) of one or more compounds of the present invention, with the balance being composed of a suitable drug carrier and/or excipient. The composition may be formed from the suitable carrier and/or excipient and the compound of the present invention by a well-known method in the art to match with an administration route.

The quantity of the active compound in a unit dose formulation may be varied between 0.001 mg and 1000 mg, preferably between 0.01 mg and 500 mg, and more preferably between 1 mg and 100 mg, and most preferably between 10 mg and 50 mg.

The administration may, for example, be oral, topical, intravenous, subcutaneous, percutaneous, transdermal, intramuscular, intra-articular, parenteral, intra-arterial, intradermal, intraventricular, encephalic, intraperitoneal, intra-damage, intranasal, rectally, vaginal, inhalational or be implanted into a reservoir. The term "parenteral" used in present invention includes subcutaneous, intravenous, intramuscular, intra-articular, intra-synovia, intra-sternum, intrathecal, intrahepatic, intra-damaged site and intracranial injection or infusion technology. Preferably, the composition is intravenously administered. The formulation of the prevent invention may be designed as quick-acting, immediate-release or long-acting. In addition, the compound may be administered topically rather than in systemic way, for example, sustained-release formulation is administered (e.g., injected). In accordance with a representative embodiment, the composition of the present invention may be prepared to administer a drug to mammal, preferably human.

One or more compositions of the prevent invention may be administered repeatedly, for example, at least 2, 3, 4, 5, 6, 7, 8 or more times, or the composition may be administered by continuous infusion. The appropriate positions of administration include, but not limited to, blood vessel, muscle, skin, bronchus, intestine and stomach, anus, vagina, eye and ear. The formulation may adopt a liquid dosage form, freeze-dry powder form, solid or semisolid, such as solution, suspension, emulsion, tablet, pill, capsule, pulvis, suppository, retention-type enema, cream, ointment, lotion, gel, aerosol, etc., a unit dosage form suitable for simply administrating accurate dose is preferred.

For parenteral administration, the composition may be in the form of sterile injection and aseptic packaging powder, and preferably, the injection is prepared in pH of 4.5-8.0.

The composition of the present invention in the form of sterile injection is water or oil suspension. Such suspension may be prepared with a suitable dispersant or wetting agent and suspending agent according to a known technology in the art. Sterile injection formulation may be a sterile injection solution or suspension dissolved or suspended in a nontoxic parenteral acceptable diluent or solvent, such as a solution dissolved in 1,3-butylene glycol. An available acceptable menstruum and solvent includes water, Ringer's solution and isotonic sodium chloride solution. Additionally, a sterile non-volatile oil is usually used as a solvent or suspended substrate. Therefore, any brand of nonvolatile oil, including synthetic monoglyceride or diglyceride may be used. As same as the naturally, pharmaceutically acceptable oil such as olive oil or castor oil, especially their polyoxyethylated form, fatty acid such as oleic acid and its glyceride derivatives may be used to prepare an injection formulation. Such oil solution or suspension may also contain long-chain alcohol diluent or dispersant, such as carboxymethylcellulose or a similar dispersant which is generally for use in the formulation of the pharmaceutically acceptable dosage form including emulsion and suspension. Other commonly used surfactants, such as Tween, Span, and other emulsifiers or bioavailable promoters which are generally used to prepare the pharmaceutically acceptable solid, liquid or other dosage forms may also be used for the purpose of the formulation. The compound for parenteral administration may be formulated by injection such as large dose injection or continuous infusion. A unit dosage form for injection may be stored in an ampoule or a multiple-dose container.

The compositions of the present invention may be provided in the form of freeze-drying. Such compositions may comprise a buffer agent such as bicarbonate for redissolution before administration, or the freeze-drying composition may comprise a buffer agent for, for example, water redissolution. The freeze-drying compositions may further comprise an appropriate vasoconstrictor, such as epinephrine. The freeze-drying composition may be provided through a syringe, optionally packaged with the buffer agent used for redissolution, in order to immediately administer this redissolution composition to a patient.

The pharmaceutical composition of the present invention may also be any orally acceptable dosage forms which include tablet, capsule, cachet, emulsion, suspension, solution, syrup, elixir, spray, pill, lozenge, pulvis, granula and a sustained-release formulation. An suitable excipient for oral administration includes medical-grade Mannitol, lactose, starch, magnesium stearate, saccharin sodium, talcum powder, cellulose, glucose, gelatin, saccharose, magnesium carbonate, etc. In case of the tablet for oral administration, the commonly used carriers include lactose and corn starch. Generally, lubricant such as magnesium stearate may also be added. In case of the capsule, an available diluent includes lactose and dry corn starch. When water suspension is required for oral medication, active ingredients are mixed with an emulsifier and suspending agents. Some of sweetening agents, corrigents or colorants may also be added according to the circumstances.

One or more compounds of the present invention and optionally one or more pharmaceutical acceptable auxiliary materials may be dissolved or dispersed in a carrier such as salt aqueous solution, glucose aqueous solution, glycerol, ethanol, etc., to form, for example, a solution or suspension for oral, topical or intravenous administration, thereby preparing the liquid composition. Sterile liquid, such as oil, water, ethanol and their combination may be used to prepare a pharmaceutical formulation in the form of liquid suspension or solution. For oral or parenteral administration, a pharmaceutically suitable surfactant, suspending agent or emulsifier may be added. Suspension may contain oil, such as peanut oil, sesame oil, cottonseed oil, corn oil, and olive oil. Suspension formulation may also contain an ester of fatty acid, such as ethyl oleate, isopropyl myristate; fatty glyceride and acetylated fatty glyceride. Suspension formulation may include alcohol, such as ethanol, isopropanol, hexadecanol, glycerol and propylene glycol. Ether such as poly (ethylene glycol); petroleum hydrocarbon, such as mineral oil and vaseline, and water may also be used for the suspension formulation.

The composition may adopt the form of pill, tablet or capsule. Therefore, the composition may contain one or more of diluents, such as lactose, saccharose, dicalcium phosphate, etc.; disintegrants, such as starch or their derivatives; lubricants, such as magnesium stearate, etc; and/or adhesives, such as starch, Arabic gum, polyvinylpyrrolidone, gelatin, cellulose, and their derivatives. The tablet may be prepared by any pressing or molding method known to the those skilled in the art. The pressed tablet may be prepared by pressing the compounds of the present invention in the form of free flow, optionally mixed with auxiliary ingredients (e.g., adhesive, lubricant, diluent, disintegrant or dispersant) in a suitable machine. The molded tablet may be prepared by molding a powder mixture of the compound of the present invention with any suitable carriers in a suitable machine.

Alternatively, the pharmaceutical composition of the present invention may be in the form of suppository for rectal administration. These suppositories may be prepared by mixing a drug with a suitable non-irritating excipient which is solid at room temperature but liquid at the rectal temperature and thus releases the drug in the rectum. Such materials include cocoa butter, beewax, polyethylene glycol, hard fat and/or hydrogenated coco-glyceride. The composition suitable for rectal administration may also contain a rectal enema unit. Such unit contains one or more compounds of the present invention and a pharmaceutically acceptable menstruum (e.g., 50% ethanol aqueous solution or salt aqueous solution). Such menstruums are physiologically compatible with the rectum and/or colon. The rectal enema unit contains an applicator tip protected by inert cover. This tip, preferably, is composed of polyethylene, lubricated with lubricant such as white vaseline, and preferably protected by a one-way valve, to prevent the released drug from refluxing. Further, the rectal enema unit has a sufficient length, preferably 2 inches, and inserted into the colon via the anus.

The pharmaceutical composition of the present invention may also be in the form of topical administration, especially when a therapeutical target includes a region or organ which is accessible by topical administration. The diseases of these organs include the diseases of eye, skin or lower intestinal tract. It is easy to prepare a suitable topical formulation for each region or organ in these regions or organs. For the topical administration, the composition containing one or more compounds of the present invention may be in the form of emulsion, lotion, gel, foam, cream, jelly, solution, suspension, ointment and transdermal patch.

The topical administration at the lower intestinal tract may be realized by a rectal suppository formulation or a suitable enema formulation. A topical transdermal patch may be used as well. For the topical administration, a suitable pharmaceutical composition in the form of ointment may be formulated, and the ointment contains active ingredients suspended or dissolved in one or more carriers. The carriers for topically administrating the compound in the present invention include, but not limited to, mineral oil, liquid vaseline, white vaseline, propylene glycol, polyoxyethylene, polyoxypropylene compound, emulsified wax and water. Alternatively, medicinal suitable pharmaceutical composition in the form of lotion or cream may be formulated, and the lotion or creation contains active ingredients suspended or dissolved in one or more pharmaceutical acceptable carriers. Suitable carriers include mineral oil, Span-60, Tween-60, cetyl ester, wax, cetanol, 2-octyldodecanol, benzyl alcohol, and water.

The pharmaceutical composition of the present invention may be administered by nasal aerosol or inhalation. For inhalation administration, the composition in the form of dry powered or liquid may be delivered by a sprayer. Such compositions are prepared according to a known technology in the pharmaceutical formulation field, and the composition in the form of solution may be prepared using benzyl alcohol or other suitable preservatives, absorption enhancer for reinforcing bioavailability, fluorocarbon and/or other conventional solubilizers or dispersants in saline.

The pharmaceutically acceptable carriers that may be used for these compositions include ion exchanger, aluminum oxide, aluminum stearate, lecithin; serum protein such as human serum albumin; buffer substance such as phosphate; glycine, sorbic acid, potassium sorbate, partial glyceride mixture of saturated vegetable fatty acid, water, salt or electrolyte such as protamine sulfate, sodium hydrogen phosphate, potassium hydrogen phosphate, sodium chloride, zinc salt; colloidal silicon dioxide, magnesium trisilicate, polyvinylpyrrolidone, cellulose substance, polyethylene glycol, sodium carboxymethylcellulose, polyacrylate, wax, polyethylene-polyoxypropylene-block polymer, polyethylene glycol and lanoline.

Examples of suitable excipients include, but not limited to, water, saline, lactose, glucose, saccharose, sorbitol, mannitol, starch, arabic gum, calcium phosphate, alginate, tragacanth, gelatin, calcium silicate, microcrystalline cellulose, polyvinylpyrrolidone, cellulose, syrup, methylcellulose, ethylcellulose, hydroxypropylmethylcellulose and polyacrylic acid, such as carbopol. The composition may also include a lubricant such as talcum powder, magnesium stearate and mineral oil; a wetting agent; an emulsifier; a suspending agent; a preservative such as methyl-, ethyl- and propyl-hydroxyl-benzoate; pH modifier such as an inorganic and organic acid and alkali; a sweetening agent; and a corrigent.

In addition to the above those representative dosage forms, other pharmaceutically acceptable excipients, carriers and dosage forms also known by those skilled in the art are included in the present invention. It is understood that the specific dosage and therapeutical schedule for any specific patients depends on many factors which include the activity of specific compounds used, patient's age, weight, general health condition, gender, diet condition, administration time, excretion rate, combined drugs, judgment of therapist and severity of specific diseases treated. The amount of the active ingredients also depends on the specific compound and (if any) other therapeutic drugs in the composition.

The above pharmaceutical compositions may further include other active ingredients for treating or auxiliary treating proliferative diseases, or may be used in combination with other drugs for treating or auxiliary treating proliferative diseases. For example, anti-proliferative agent, immunomodulator, anticancer drug, cytotoxic agent, and anticancer aided drug in addition to those of the present invention are used in combination.

Other examples of these therapeutic agents include anti-proliferative agent, such as methotrexate; FK506 (fujimycin, Prograf), mycophenolate mofetil; cytotoxic drugs, such as azathioprine and cyclophosphamide; TNF-α inhibitor, such as Tenidap; anti-TNF antibody or soluble TNF receptor, such as etanercept (Enbrel); Rapamycin, Ieflunimide, and cyclo-oxygenase-2 (COX-2) inhibitor, such as celecoxib and rofecoxib, or their derivatives; and PTK inhibitors disclosed in the existing technology.

Typical various anticancer drugs and cytotoxic agents include, but not limited to, alkylated agents, such as chlormethine, alkylsulphonate, nitrourea, aziridine and triazene; antimetabolites, such as folate antagonist, purine analogues and pyrimidine analogues; antibiotics, such as anthracycline, bleomycin, mitomycin, dactinomycin and streptomyces plicatus; enzymes, such as L-asparaginase; farnesyl protein transferase inhibitor; hormone medicaments, such as glucocorticoid, estrogen/antiestrogen, androgen/antiandrogen, progesterone, luteinizing hormone releasing hormone antagonist, acetic acid sandostatin; microtubules breaker, such as ecteinascidin or its analogues and derivatives; microtubules stabilizer, such as paclitaxel, docetaxel and epothilone or their analogues or derivatives; products derived from vegetables, such as Vinca Alkaloids, epipodophyllotoxin, taxane; topoisomerase inhibitor; prenyl-protein transferase inhibitor; miscellaneous reagents, such as hydroxycarbamide, procarbazine, mitotane, hexamethyl melamine, platinum coordinated complex such as cisplatin and carboplatin; and other anticancer drugs and cytotoxic agents, such as biological response regulator, growth factor; and immunomodulator and monoclonal antibody. The compound of the present invention may also be used in combination with radiotherapy.

The examples of these categories of anticancer drugs and cytotoxic agents include, but not limited to, chlormethine hydrochloride, cyclophosphamide, chlorambucil, betamerphalan, ifosfamide, busulfan, carmustine, lomustine, semustine, streptozotocin, thiotepa, dacarbazine, methotrexate, thioguanopterin, mercaptopurine, fludarabine, Pentastatin, Cladiribine, cytarabine, fluorouracil, doxorubicin hydrochloride, daunorubicin, idarubicin, bleomycin sulfate, mitomycin C, dactinomycin D, safracins, Micronomicin, quinocarcins, discodermolides, vincristine, vinblastine, vinorelbine tartrate, etoposide, teniposide, paclitaxel, tamoxifen, estramustine, sodium estramustine phosphate, Flutamide, Buserelin, Lupron, pteridine, diynes, levomisole, aflacon, interferon, interleukin, Aldesleukin, Felsdine, myeloid growth factor, rituximab, BCG, vitamin A acid, irinotecan hydrochloride, betamethasone, gemcitabine hydrochloride, hexamethy pyrimidine and Topotecan, and any analogues or derivatives thereof.

The preferred members in those categories include, but not limited to, paclitaxel, cisplatin, carboplatin, adriamycin, idarubicin, daunorubicin, aminopterin, methotrexate, methylpetrin, mitomycin C, ecteinascidin, pholipomycin, 5-fluorouracil, 6-mercaptopurine, gemcitabine, cytarabine, podophyllotoxin or podophyllotoxin derivatives, such as etoposide, etoposide phosphate or teniposide, betamerphalan, vinblastine, vincristine, leurosidine, vindesine and leurosine.

Examples of antitumor drugs and other cytotoxic agents include, epothilone derivatives in U.S. patent application Ser. No. 09/506,481 filed on Feb. 17, 2000, German patents 41380428, WO97/19086, WO98/22461, WO98/25929, WO98/38192, WO99/01124, WO99/02224, WO99/02514, WO99/03848, WO99/07692, WO99/27890, WO99/28324, WO99/43653, WO99/54330, WO99/54318, WO99/54319, WO99/65913, WO99/67252, WO99/67253, and WO00/00485; a kinase inhibitor depending on a cell cycle protein in WO99/24416; and an prenyl protein transferase inhibitor in WO97/30992 and WO98/54966.

When used with the compound of the present invention, the above other therapeutic agents may adopt, for example, the dosage pointed out in the clinical medicine manual or the dosage determined by those ordinary skilled in the art.

Finally, the present invention further provides a method for treating cell proliferative diseases, comprising administering to a patient in need a therapeutically effective amount of the compound of formula A.

"Cell proliferative diseases" refer to the diseases characterized in abnormal proliferation of cells. The proliferative diseases do not represent any limit to the cell growth rate but only represent the loss of the normal control affecting growth and cell division. Therefore, the cells with proliferation diseases may have the same cell division rate as normal cells without responding the signal restricting such growth. "Cell proliferative diseases" is within the scope of neoplasms or tumors which are the abnormal growth of tissues. "Cancer" refers to any one of various malignant tumors characterized in cell proliferation, such tumors have the capability to intrude into surrounding tissues and/or transfer to a new settlement position.

In general, the cell proliferative diseases that may be treated with the compound disclosed in this document relate to any symptoms characterized in the abnormal cell proliferation. These diseases include various benign or malignant, transferred or non-transferred tumors and cancers. The method described in this document may be used for confronting the particular characteristics of tumors, such as tissue invasiveness or transitivity. Cell proliferation diseases include various cancers, which include, but not limited to, cancer, including bladder cancer, breast cancer, colon cancer, renal cancer, liver cancer, lung cancer, cellule lung cancer, ovarian cancer, prostate cancer, pancreatic cancer, esophageal cancer, gastric cancer, gallbladder cancer, cervical cancer, thyroid cancer and skin cancer, squamous cell carcinoma;

hematopoietic tumors of lymphatic system, including leukemia, acute lymphatic system leukemia, acute lymphoblastic leukemia, β-cell lymphoma, T-cell lymphoma, Hodgkins lymphoma, non-Hodgkins lymphoma, villus cell lymphoma and Burketts lymphoma;

hematopoietic tumors of medullary system, including acute and chronic myelocytic leukemia, myelodysplastic syndromes and promyelocytic leukemia;

tumors of central and peripheral nervous system, including astrocytoma, neuroturbo chargeoma, glioma and schwannoma;

neoplasms of mesenchymal origin, including fibrosarcoma, rhabdomyosarcoma and osteosarcoma; and other tumors, including melanoma, xenoderma pigmentosum, amination acanthoma, seminoma, follicular thyroid carcinoma and teratocarcinoma.

Cell proliferative diseases which may be treated with said compound include hematologic neoplasms which are the cell hyperplasia of the hemopoietic system.

The hematologic neoplasms include lymphocytoma, wherein the abnormal cell originates from cells of a lymphoid cell lineage and/or shows characteristic phenotypes of cells of a lymphoid cell lineage. Lymphoid cytomas may be subdivided into B cytoma, T and NK cytoma, and Hodgkin lymphoma. B cytoma may be further subdivided into ancestor B cytoma and mature/peripheral B cytoma. B cytoma includes precursor B lymphocyte leukemia/lymphoma (precursor B cell acute lymphocyte leukemia), while the mature/peripheral B cytoma includes B cell chronic lymphocyte leukemia/small lymphocytic lymphoma, B cell prolymphocytic leukemia, lymphoplasmacytic lymphoma, splenic marginal zone B cell lymphoma, hairy cell leukemia, plasma cell myeloma/plasmacytoma, MALT type universal zone B cell lymphoma, lymphaden marginal zone B cell lymphoma, follicle lymphoma, jacket cell lymphoma, diffuse large B cell lymphoma, mediastinal large B cell lymphoma, primary effusion lymphoma and Burkitt lymphoma/Burkitt cell leukemia. T cytoma and Nk cytoma may be subdivided into precursor T cell cancer and mature (peripheral) T cytoma. Precursor T cytoma includes precursor T-lymphocyte lymphoma/leukemia (precursor T cell acute lymphocyte leukemia), while mature (peripheral) T cytoma includes T cell prolymphocyte leukemia T cell particle lymphocyte leukemia, aggressive NK cell leukemia, adult T cell lymphoma/leukemia (HTLV-1), extranodal nasal type NK/T cell lymphoma; nasal type, pathotype T cell lymphoma, hepatolienal γ-δ T cell lymphoma, subcutaneous panniculitis-like T cell lymphoma, granuloma fungoides/Sezary syndrome, retrogressive maxicell lymphoma; T/invalid cell, primary skin type peripheral T cell lymphoma, non-additionally characterized angioimmunoblastic T cell lymphoma, retrogressive maxicell lymphoma, T/invalid cell, and primary body type. The third type of lymphoid cell tumor is Hodgkin lymphoma, also referred to as Hodgkin's disease. Such diseases which may be treated with said compound include, but not limited to, nodular lymphocyte predominant Hodgkin lymphoma and various Hodgkin's diseases in classic form, nodular hardening Hodgkin lymphoma (level 1 and level 2), lymphocyte-enriched classic Hodgkin lymphoma, Hodgkin lymphoma composed of mixed cells and lymphocytic depletion Hodgkin lymphoma.

The hematologic neoplasm also includes myelocytome. Such tumor includes a major category of cell proliferative diseases involving or showing the characteristic phenotypes of myelocyte lineage cells. The myelocytome may be subdivided into myeloproliferative diseases, myeloproliferative disorders/myelodysplastic diseases, myelodysplastic syndrome and acute myeloid leukemia. The myeloproliferative diseases include chronic myeloid granulocytic leukemia, chronic neutrophils granulocytic leukemia, chronic eosinophilic granulocytic leukemia/hypereosinophilic syndrome, chronic idiopathic myelofibrosis, polycythemia and primary thrombocythemia. The myeloproliferative disorders/myeloproliferative diseases include chronic myelomonocytic leukemia, atypical chronic myeloid granulocytic leukemia and teenager myelomonocytic leukemia. The myelodysplastic syndrome includes the refractory anemia with and without annular sideroblast, refractory cytopenia with multilinkage dysplasia (myelodysplastic syndrome), refractory anemia with excessive germ cell (myelodysplastic syndrome), 5q-syndrome and myelodysplastic syndrome. The compound of the present invention may be used to treat any relevant myelocytomes.

Said compounds may be used to treat acute myeloid leukemia (AML) which represents a major category of myelocytome which may be subdivided into symptoms. Such embranchments include, but not limited to, AML with recurrent chromosomal translocation, AML with multilinkage dysplasia and other unclassified AMLs. The AMLs with recurrent chromosomal translocation include, but not limited to, AML with t (8; 21) (q22; q22), AML1 (CBF-α)/ETO, acute promyelocytic leukemia (AML with t(15; 17) (q22; q11-12) and variants, PML/RAR-α), AML with abnormal myeloid eosinophil cell (inv(16) (p13q22) or t(16; 16) (p13; q11), CBFb/MYH11X), and 11q23 (MLL) abnormal AML. Other acute myeloid leukemias which are not classified into the category of any definition include minimally differentiated AML, immature AML, mature AML, acute myelomonocytic leukemia, acute mononuclear leukemia, acute erythroid leukemia, acute megakaryocyte leukemia, acute basophil leukemia and acute panmyelosis leukemia with myelofibrosis.

Preferably, the treated tumors are breast cancer, lung cancer, colon cancer, gastric cancer, esophagus cancer, ovarian cancer, osteosarcoma, cervical cancer, liver cancer, cerebroma, prostate cancer, and melanoma.

The term "treatment" in the present invention indicates the relief of the symptoms relating to symptoms or diseases or termination of the further development or deterioration of those symptoms, or stopping or preventing the diseases or symptoms.

The term "pharmaceutically effective amount", "therapeutically effective amount" or "therapeutically effective dosage" refers to the amount of the topic compound, which research personnel, veterinarians, physicians or other clinical technicians seek for, causing the biological or medical reaction from tissue, system, animal or human.

The term "therapeutically effective amount" includes the amount of compound which is sufficient to stop one or more symptoms of diseases or symptoms during the treatment developing or to relieve it to a certain degree after being administered. The therapeutically effective amount should be varied with the compound, symptom or status and severity thereof, as well as the age, weight, etc. of the mammal treated.

The term "patient" defined in this document includes animals, such as mammals Mammals include, but not limited to, primate (e.g., human), cow, sheep, goat, horse, dog, cat, rabbit, rat, mouse, etc. In a preferred embodiment, the patient is human. The effective amount of the compound of the present invention may be determined by the ordinary skilled in the art. For adult, the dosage is about 0.001 mg to 1000 mg of the active compound per kg of weight per day. The drug may be administered in a single dose or in respective divided dose, such as 1-4 times per day. It should be clear that, for any specific objects, the specific dosage level and administration frequency may be varied depending on many factors, including the activity of the specific compound used, metabolic stability and acting duration of the compound, species, age, weight, health status, gender, and dietary habit of the administration object, administration way and time, excretion rate, combination of drugs, and the severity of specific symptoms.

As compared with that of the existing antitumor platinum compound, the solubility of the free compound of the present invention is significantly improved, and its solubility is above 80 mg/ml in water, especially for those preferred compounds in the examples of the present invention, the solubility is generally 100 mg/ml or more. Moreover, the existing platinum compound cannot be salinized. The compound of the present invention may produce a salt form and is more favorable for producing into a stable formulation form.

The above dosage forms of any compounds containing an effective amount are within the scope of the conventional experiments and the present invention. Therapeutically effective amount may be adjusted according to the administration route and dosage form. The representative compound of the present invention is a formulation showing high therapeutic index. Therapeutic index is a dosage ratio between the toxicity and the curative effect and may be expressed by a ratio between $LD_{50}$ and antitumor activity in vivo ($ED_{50}$) or cytotoxicity in vitro ($IC_{50}$). $LD_{50}$ is a lethal dosage for 50% population; $ED_{50}$ is the therapeutically effective dosage achieved in 50% population. $LD_{50}$ and $ED_{50}$ are determined in an animal cell culture medium or an experimental animal by standard pharmaceutical method. Since $LD_{50}$ (a dosage causing 50% animal lethal, mg/kg) representing toxicity of the compound in the present invention is much higher than that of the existing platinum compound such as cisplatin and carboplatin, etc., and the effective dosage of the antitumor activity in vivo and concentration of inhibiting cell toxicity in vitro $IC_{50}$ value of the compound in the present invention are equivalent with or lower than those of carboplatin, it may be used for treating the patient who cannot tolerate the existing platinum compounds such as carboplatin, cisplatin, etc. and thereby achieving a favourable technical effect. The compound of the present invention may be used individually or in combination with each other, and/or in combination with other suitable therapeutic agents used for treating proliferative diseases.

PREFERRED EMBODIMENTS OF THE PRESENT INVENTION

The implementation of the present invention was described by the following examples and test examples in details, but will not limit the present invention in any way. It should be understood by those skilled in the art that any modifications or substitutions of the corresponding technical features according to the instructions of the prior art still belong to the scope claimed by the present invention. The purity of the raw materials used in the present invention is just above chemical purity, which can be purchased commercially. The compounds obtained in the following examples are all in the form of salt, which may be obtained by adding an alkali to adjust pH to obtain a free compound and can be easily converted into other types of organic or inorganic salts by using the method of adding a corresponding acid, which possibly include, but not limited to, nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactose acid salt, etc. This will no longer be illustrated in the following examples one by one. In addition, for the compound having a chiral center, its racemes are generally synthesized by a conventional method, and its optical isomers are obtained by using a conventional resolution method in the art and using a asymmetric synthesis method when synthesizing, these methods are conventional technologies well-known by those skilled in the art.

[Example 1]:
2-(4-diethylaminobutyl)-malonate•cis-diamine platinum (II) acetate

Step 1: 2-(4-bromobutyl)-diethyl malonate

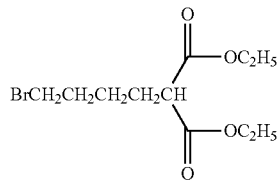

16.06 g (0.1 mol) diethyl malonate and 21.6 g (0.1 mol) 1,4-dibromobutane were placed into a 150 ml three-necked flask, 15.12 g (0.11 mol) $K_2CO_3$ and 156 mg tetrabutylammonium bromide were added and stirred, the mixture was heated to 65° C.~85° C. in an oil bath for 16 h 24 h; suction filtration was conducted to remove the solid which was washed with ethyl ether (30 ml×3 times), the filtrate was combined, and the organic layer was washed with water (40 ml×3 times) and then dried over $MgSO_4$ for 4 h~8, the solvent was distilled under reduced pressure, and then distilled under reduced pressure using an oil pump, 9.35 g of fraction at 140° C.~151° C. under the vacuum degree of 7 mmHg was collected, with the yield of 31.69%.

Step 2: diethyl 2-(4-diethylaminobutyl)-malonate

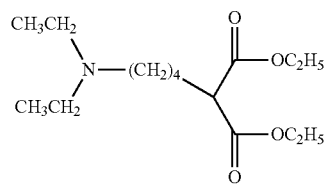

117.9 g (0.4 mol) diethyl 4-bromobutyl-malonate was placed into a three-necked flask, 55.5 g (0.4 mol) anhydrous $K_2CO_3$ and 500 ml acetonitrile were added and stirred. 73.2 g (1.0 mol) diethylamine was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous $MgSO_4$ overnight, the solvent was pumped out under reduced pressure using a water pump, to obtain 103.5 g of light yellow, light red, transparent substance which was purified by column chromatography to obtain 48.55 g pure product, with the yield of 42.29%.

Step 3: disodium 2-(4-diethylaminobutyl)-malonate

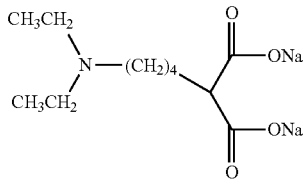

2M NaOH solution was obtained by dissolving 212.1 mg (5 mmol) NaOH with 2.5 mL water. 575 mg (2 mmol) diethyl 2-(4-diethylaminobutyl)-malonate was placed into a 20 mL three-necked flask, and the above NaOH solution was added thereto, stirring at room temperature for 45 h~60 h, to obtain a solution of disodium 2-(4-diethylaminobutyl)-malonate.

Step 4: diamine•diiodoplatinum (II)

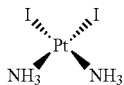

2.075 g (5 mmol) potassium tetrachloroplatinate ($K_2PtCl_4$) was added in 50 ml water and dissolved by stirring at room temperature, and 6.640 g (40 mmol) KI was added in the reaction solution after being dissolved with 50 ml water, with the protection of $N_2$ and away from light, the mixture was heated to 40° C.~60° C. in a water bath for 0.5 h~2 h. Then 50 ml ammonia water (containing 5 mmol ammonia) was added in the reaction solution, which was kept under this condition to react for 0.5 h~2 h. A light yellow solid product was obtained by suction filtration and washed with water (10 ml×3 times) and ethyl ether (10 ml×3 times), to obtain 2.29 g product, with the yield of 95.1%. Elemental analysis: H, 1.24% (theoretical 1.21%), N, 5.56% (theoretical 5.797%).

Step 5: diamine•dihydrated platinum (II) sulphate

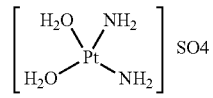

625 mg (2 mmol) $Ag_2SO_4$ was placed in a 100 ml three-necked flask, 30 ml water was added thereto and stirred, and 0.96 g (2 mmol) diamine•diiodoplatinum (II) was added into the reaction solution and then 40 ml water was added to react, with the protection of $N_2$ and away from light, the mixture was reacted in a water bath at 40° C.~60° C. for 4 h~8 h. After removing AgI precipitate by suction filtration, the filtrate was obtained, i.e., the aqueous solution of the product.

Step 6: 2-(4-diethylaminobutyl)-malonate•cis-diamine platinum (II) acetate

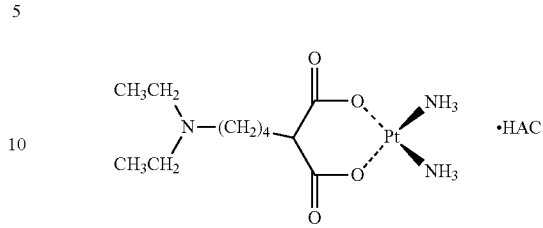

The pH of disodium [2-(4-diethylaminobutyl)-malonate solution was adjusted to 5~7 with 1M HAC and then cis-diamine•dihydrated platinum (II) sulphate aqueous solution was poured into the reaction solution, with the protection of $N_2$, the mixture is heated to 40° C.~75° C. in a water bath for 4 h-6 h, and the reaction solution was concentrated to a certain volume after suction filtration and stayed, to obtain 130 mg crystalline-type product.

The compound in Example 1 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 28.72% (theoretical 28.82%), H, 5.61% (theoretical 5.46%), N, 8.98% (theoretical 9.17%).

$^1$HNMR ($D_2O$) (ppm): $\delta 3.52$ (m, 1H), $\delta 2.79$-2.67 (b, 4H), $\delta 2.57$-2.67 (b, 2H), $\delta 1.80$ (m, 2H), $\delta 1.45$ (m, 2H), $\delta 1.24$ (m, 2H), $\delta 1.05$ (t, 6H).

[Example 2]: 2-(4-diethylaminobutyl)-malonate•cis-(1, 2-ethylenediamine) platinum (II) tosilate Steps 1, 2 and 3 are the same as steps 1, 2, and 3 in [Example 1], respectively.

Step 4: 1, 2-ethanediamine•diiodoplatinum (II)

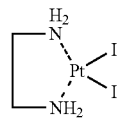

2.076 g (5 mmol) potassium tetrachloroplatinate ($K_2PtCl_4$) is added in 50 ml water and dissolved by stirring at room temperature, and 6.64 g (40 mmol) KI is added in the reaction solution after being dissolved with 50 ml water, with the protection of $N_2$ and away from light, the mixture was heated to 40° C.~60° C. in a water bath for 0.5 h~2 h, and then 301 mg (5 mmol) refrigerated 1,2-ethylenediamine (commercially available) was added in the reaction solution after being dissolved with 50 ml water, which was kept under this condition to react for 0.5~2 h. A yellow solid product is obtained by suction filtration, and washed with water (10 ml×3 times) and ethyl ether (10 ml×3 times), to obtain 2.254 g product, with the yield of 89.8%. Elemental analysis: C, 4.77% (theoretical 4.72%), H, 1.41% (theoretical 1.57%), N, 5.41% (theoretical 5.50%).

Step 5: 1, 2-ethylenediamine•dihydrated platinum (II) sulphate

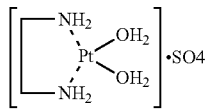

625 mg (2 mmol) Ag$_2$SO$_4$ is placed in a 100 ml three-necked flask, 30 ml water is added thereto and stirred, and 1.020 g (2 mmol) 1, 2-ethylenediamine•diiodoplatinum (II) is added into the reaction solution and then 40 ml water is added to react, with the protection of N$_2$ and away from light, the mixture is reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1, 2-ethylenediamine) platinum (II) tosilate

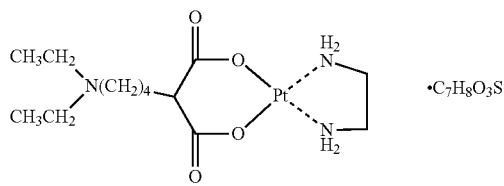

The pH of disodium 2-(4-diethylaminobutyl)-malonate solution was adjusted to 5~7 with 1M p-toluenesulfonic acid C$_7$H$_8$O$_3$S, and then 1,2-ethylenediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes), and stirred for 15 min and then pumped to be dryness, the mixture is treated by column chromatography to obtain 138 mg product.

The compound in Example 2 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, phosphate, fumarate, etc. Elemental analysis of the free alkali: C, 32.31% (theoretical 32.23%), H, 5.65% (theoretical 5.58%), N, 8.82% (theoretical 8.68%).

$^1$HNMR (D$_2$O) (ppm): δ3.51 (m, 1H), δ2.77-2.67 (br, 4H), δ2.65-2.57 (br, 2H), δ2.25 (br, 4H), δ1.79 (m, 2H), δ1.44 (m, 2H), δ1.23 (m, 2H), δ1.05 (t, 6H).

[Example 3]: 2-(4-diethylaminobutyl)-malonate•cis-(1, 2-trans-cyclohexanediamine) platinum (II) tosilate Steps 1, 2 and 3 are the same as steps 1, 2 and 3 in [Example 1], respectively.

Step 4: Trans-cyclohexanediamine•diiodoplatinum(II)

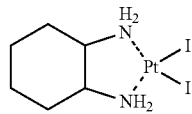

2.075 g (5 mmol) potassium tetrachloroplatinate (K$_2$PtCl$_4$) was added in 50 ml water and dissolved by stirring at room temperature, and 6.640 g (40 mmol) KI was added in the reaction solution after being dissolved with 50 ml water, with the protection of N$_2$ and away from light, the mixture was heated to 40° C.~60° C. in a water bath for 0.5 h~2 h, and then 571 mg (5 mmol) trans-cyclohexanediamine was added into the reaction solution after being dissolved in 50 ml water, which was kept under this condition to react for 0.5 h~2. A yellow solid product is obtained by suction filtration and washed with water (10 ml×3 times) and ethyl ether (10 ml×3 times), to obtain 2.709 g product, with the yield of 96.2%. Elemental analysis: C, 12.68% (theoretical 12.80%); H, 2.61% (theoretical 2.51%); N, 4.99% (theoretical 4.98%).

Step 5: trans-1, 2 cyclohexanediamine•dihydrated platinum (II) sulfate

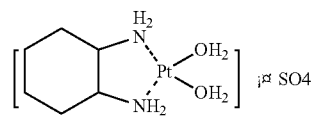

625 mg (2 mmol) Ag$_2$SO$_4$ was placed in a 100 ml three-necked flask, 30 ml water was added thereto and stirred, and 1.126 g (2 mmol) trans-cyclohexanediamine•diiodoplatinum (II) was added into the reaction solution and then 40 ml water is added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1, 2-trans-cyclohexanediamine) platinum (II) tosilate

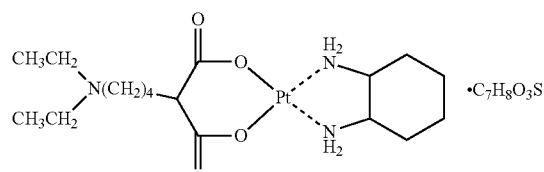

The pH of disodium [2-(4-diethylaminobutyl)-malonate solution was adjusted to 5~7 with 1M p-toluenesulfonic acid and then trans-cyclohexanediamine•dihydrated platinum (II) sulphate is poured into the reaction solution, with the protection of N$_2$, the mixture is heated to 40° C.~60° C. in a water bath for 4 h-8 h, and the reaction solution was added into 2.5 g silica gel for column chromatography (200-300 meshes) and stirred for 15 min and then pumped to be dryness, the mixture was treated by column chromatography to obtain 157 mg product.

The compound in Example 3 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 37.76% (theoretical 37.92%), H, 6.25% (theoretical 6.13%), N, 7.70% (theoretical 7.81%).

$^1$HNMR (D$_2$O) (ppm): δ3.52 (m, 1H), δ2.78-2.65 (br, 4H), δ2.67-2.56 (br, 2H), δ2.05 (br, 2H), δ1.80 (m, 4H), δ1.46 (m, 4H), δ1.25 (m, 4H), δ1.05 (t, 6H), δ1.01 (m, 2H).

[Example 4]: 2-(4-(1-piperidyl)-butyl)-malonate•cis-diamine platinum (II) phosphate Step 1 is the same as step 1 in [Example 1].

Step 2: diethyl 2-(4-(1-piperidyl)-butyl)-malonate

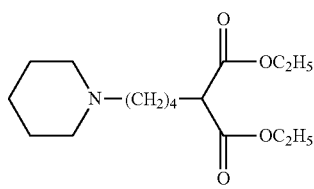

117.9 g, (0.4 mol) diethyl 4-bromobutyl-malonate was placed into a three-necked flask, 55.5 g (0.4 mol) anhydrous K$_2$CO$_3$ and 500 ml acetonitrile were added and stirred. 85.0 g (1.0 mol) piperidine solution was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 101.2 g of light yellow, light red, transparent substance which was purified by column chromatography to obtain 36.71 g pure product, with the yield of 30.69%.

Step 3: disodium 2-(4-(1-piperidyl)-butyl)-malonate

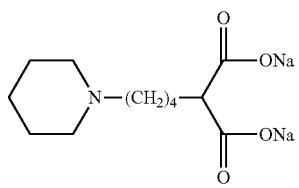

2M NaOH solution was obtained by dissolving 212.3 mg (5 mmol) NaOH with 2.5 mL water. 599 mg (2 mmol) diethyl 2-(4-(1-piperidyl)-butyl)-malonate was placed into a 20 mL three-necked flask and the above NaOH solution was added thereto, stirring at room temperature for 45 h~60 h, to obtain a solution of disodium 2-(4-(1-piperidyl)-butyl)-malonate.

Steps 4, 5 are the same as steps 4, 5 in [Example 1], respectively.

Step 6: 2-(4-(1-piperidyl)-butyl)-malonate-cis-diamine platinum (II) phosphate

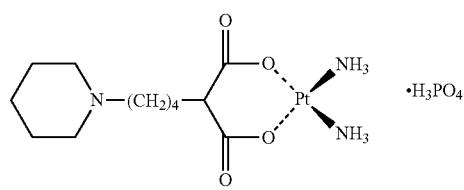

The pH of disodium 2-(4-(1-piperidyl)-butyl)-malonate solution was adjusted to 5~7 with 1M H$_3$PO$_4$ and then cis-diamine•dihydrated platinum (II) sulphate aqueous solution was poured into the reaction solution, with the protection of N$_2$, the mixture was heated to 40° C.~75° C. in a water bath for 4 h-6 h, and the reaction solution was concentrated to a certain volume after suction filtration and stayed, to obtain 138 mg crystalline-type product.

The compound in Example 4 was soluble in water, the solubility was more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 30.47% (theoretical 30.64%), H, 5.13% (theoretical 5.32%), N, 9.00% (theoretical 8.94%).

$^1$H NMR (D$_2$O) (ppm): δ3.61 (t, 1H), δ2.83 (t, 4H), δ2.71 (t, 2H), δ1.84 (m, 2H), δ1.76 (m, 4H), δ1.54 (m, 2H), δ1.42 (m, 2H), δ1.33 (m, 2H).

[Example 5]: 2-(4-(1-tetrahydropyrrolidinyl)-butyl)-malonate•cis-diamine platinum (II) phosphate Step 1 is the same as step 1 in [Example 1].

Step 2: diethyl 2-(4-(1-tetrahydropyrrolidinyl)-butyl)-malonate

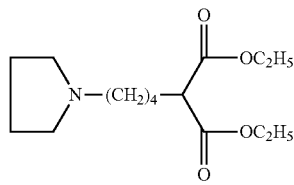

118.1 g, (0.4 mol) diethyl 4-bromobutyl-malonate was placed into a three-necked flask, 55.53 g (0.4 mol) anhydrous K$_2$CO$_3$ and 500 ml acetonitrile were added and stirred. 71.2 g (1.0 mol) tetrahydropyrrolidine was added in the reaction solution, and the mixture was heated to 40° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO₄ overnight, the solvent was pumped out under reduced pressure using a water pump, to obtain 96.4 g of light yellow, light red, transparent substance which was purified by column chromatography to obtain 31.23 g pure product, with the yield of 27.39%.

Step 3: disodium 2-(4-(1-piperidyl)-butyl)-malonate

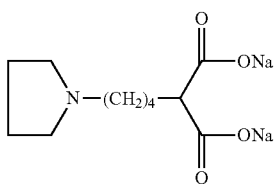

2M NaOH solution was obtained by dissolving 212.4 mg (5 mmol) NaOH with 2.5 mL water. 545 mg (2 mmol) diethyl 2-(4-(1-tetrahydropyrrolidinyl)-butyl)-malonate was placed into a 20 mL three-necked flask and the above NaOH solution was added thereto, stirring at room temperature for 45 h~60 h, to obtain a solution of disodium 2-(4-(1-tetrahydropyrrolidinyl)-butyl)-malonate.

Steps 4, 5 are the same as steps 4, 5 in [Example 1], respectively.

Step 6: 2-(4-(1-tetrahydropyrrolidinyl)-butyl)-malonate•cis-diamine platinum (II) phosphate

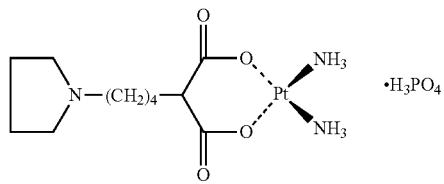

The pH of disodium 2-(4-(1-tetrahydropyrrolidinyl)-butyl)-malonate solution was adjusted to 5~7 with 1M H₃PO₄ and then cis-diamine•dihydrated platinum (II) sulphate aqueous solution was poured into the reaction solution, with the protection of N₂, the mixture was heated to 40° C.~75° C. in a water bath for 4 h-6 h, and the reaction solution was concentrated to a certain volume after suction filtration and stayed, to obtain 128 mg crystalline-type product.

The compound in Example 5 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 28.71% (theoretical 28.95%), H, 4.97% (theoretical 5.04%), N, 9.37% (theoretical 9.21%).

¹HNMR (D₂O) (ppm): δ3.62 (t, 1H), δ2.83 (t, 4H), δ2.72 (t, 2H), δ1.85 (m, 2H), δ1.78 (m, 4H), δ1.51 (m, 2H), δ1.33 (m, 2H).

[Example 6]:2-(3-dimethylaminocyclobutyl)-malonate•cis-diamine platinum (II) mesylate Step 1: diethyl 2-(3-bromocyclobutyl)-malonate

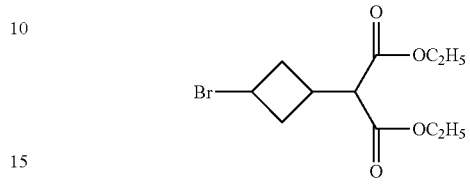

16.02 g (0.1 mol) diethyl malonate and 21.5 g (0.1 mol) 1, 3-dibromocyclobutyl were placed into a 150 ml three-necked flask, 15.13 g (0.11 mol) K₂CO₃ and 154 mg tetrabutylammonium bromide were added and stirred, the mixture was heated to 65° C.~85° C. in an oil bath for 16 h~24 h; suction filtration was conducted to remove the solid which was washed with ethyl ether (30 ml×3 times), the filtrate was combined, and the organic layer was washed with water (40 ml×3 times) and then dried over MgSO₄ for 4~8 h, the solvent was distilled under reduced pressure, and then distilled under reduced pressure using an oil pump, 9.21 g of fraction at 141° C.~150° C. under the vacuum degree of 7 mm Hg was collected, with the yield of 31.43%.

Step 2: diethyl 2-(3-dimethylaminocyclobutyl)-malonate

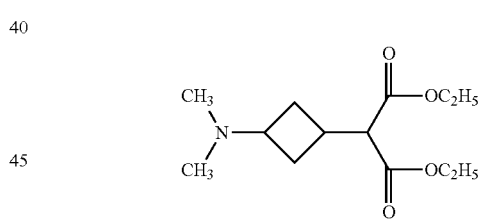

117.21 g, (0.4 mol) diethyl 3-bromocyclobutyl-malonate was placed into a three-necked flask, 55.820 g (0.4 mol) anhydrous K₂CO₃ and 500 ml acetonitrile were added and stirred. 45.2 g (1.0 mol) refrigerated dimethylamine solution was added in the reaction solution, and the mixture was heated to 40° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO₄ overnight, the solvent was pumped out under reduced pressure using a water pump, to obtain 90.5 g of light yellow, light red, transparent substance which was purified by column chromatography, to obtain 41.3 g pure product, with the yield of 40.18%.

Step 3: disodium 2-(3-dimethylaminocyclobutyl) malonate

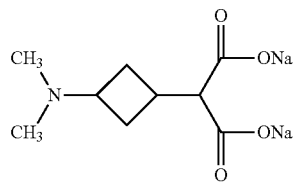

2M NaOH solution was obtained by dissolving 213 mg (5 mmol) NaOH with 2.5 mL water, and 514 mg (2 mmol) diethyl 2-(3-dimethylaminocyclobutyl)-malonate was placed into a 20 mL three-necked flask and the above NaOH solution was added thereto, stirring at room temperature for 45 h~60 h, to obtain a solution of disodium 2-(3-dimethylaminocyclobutyl)-malonate.

Steps 4, 5 are the same as steps 4, 5 in [Example 1], respectively.

Step 6: 2-(3-dimethylaminocyclobutyl)-malonate•cis-diamine platinum (II) mesylate

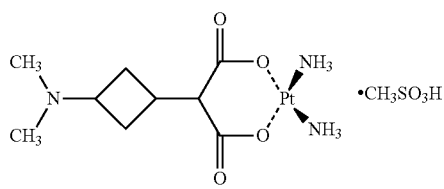

The pH of 2 mmol disodium 2-(3-dimethylaminocyclobutyl) malonate solution was adjusted to 5~7 with 1M methylsulfonic acid and then cis-diamine•dihydrated platinum (II) sulphate aqueous solution was poured into the reaction solution, with the protection of $N_2$, the mixture was heated to 40° C.~75° C. in a water bath for 4 h-6 h, and the reaction solution was concentrated to a certain volume after suction filtration and stayed, to obtain 143 mg crystalline-type 2-(3-dimethylaminocyclobutyl)-malonate•cis-diamine platinum (II) phosphate.

The compound in Example 6 is soluble in water, the solubility is more than 300 mg/ml. A free compound 2-(3-dimethylaminocyclobutyl)-malonate•cis-diamine platinum (II) could be obtained by adjusting pH with an alkali. Elemental analysis of the free alkali: C, 25.09% (theoretical 25.23%), H, 4.56% (theoretical 4.44%), N, 9.77% (theoretical 9.81%).

$^1$HNMR ($D_2O$) (ppm): δ3.61 (d, 1H), δ2.87 (s, 6H), δ2.63 (m, 1H), δ1.73 (dd, 4H), δ1.45 (m, 1H).

[Example 7]: 2-(4-di-n-propylaminobutyl)-malonate•cis-diamine platinum (II) phosphate Step 1 is the same as step 1 in [Example 1].

Step 2: diethyl 2-(4-di-n-propylaminobutyl)-malonate

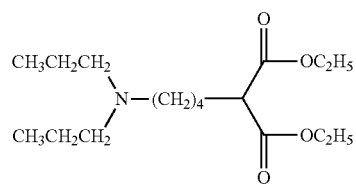

118 g (0.4 mol) diethyl 4-bromobutyl-malonate was placed into a three-necked flask, 55.2 g (0.4 mol) anhydrous $K_2CO_3$ and 500 ml acetonitrile were added and stirred. 101.2 g (1.0 mol) di-n-propylamine was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous $MgSO_4$ overnight, the solvent was pumped out under reduced pressure using a water pump, to obtain 117.5 g of light yellow, light red, transparent substance which was purified by column chromatography to obtain 49.51 g pure product, with the yield of 39.29%.

Step 3: disodium 2-(4-di-n-propylaminobutyl)-malonate

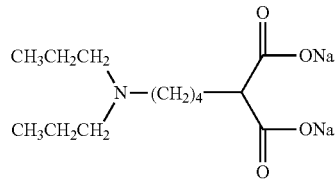

2M NaOH solution was obtained by dissolving 213 mg (5 mmol) NaOH with 2.5 mL water. 630 mg (2 mmol) diethyl 2-(4-di-n-propylaminobutyl)-malonate was placed into a 20 mL three-necked flask and the above NaOH solution was added thereto, stirring at room temperature for 45 h~60 h, to obtain a solution of disodium 2-(4-di-n-propylaminobutyl)-malonate.

Steps 4, 5 are the same as steps 4, 5 in [Example 1], respectively.

Step 6: 2-(4-di-n-propylaminebutyl)-malonate•cis-diamine platinum (II) phosphate The pH of disodium 2-(4-di-n-propylaminobutyl)-malonate solution was adjusted to 5~7 with 1M $H_3PO_4$ and then cis-diamine•dihydrated platinum (II) sulphate aqueous solution was poured into the reaction solution, with the protection of $N_2$, the mixture was heated to 45° C.~75° C. in a water bath for 4 h-6 h, and the reaction solution was concentrated to a certain volume after suction filtration and stayed, to obtain 133 mg crystalline-type product.

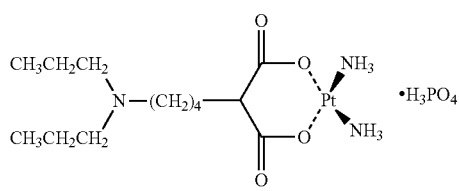

The compound in Example 7 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 32.29% (theoretical 32.10%)); H, 5.72% (theoretical 5.97%); N, 8.59% (theoretical 8.64%).

$^1$HNMR (D$_2$O) (ppm): δ3.60 (t, 1H), δ2.77 (t, 4H), δ2.70 (t, 2H), δ1.78 (m, 2H), δ1.44 (m, 2H), δ1.31 (m, 2H), δ1.25 (m, 4H), δ1.05 (t, 6H).

[Example 8]: 2-(3-methyl-4-diethylaminobutyl)-malonate•cis-diamine platinum (II) acetate Step 1: diethyl 2-(3-methyl-4-bromobutyl)-malonate

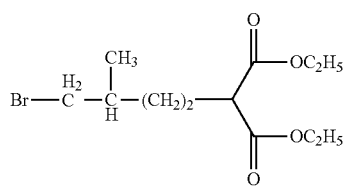

16.1 g (0.1 mol) diethyl malonate and 23.0 g (0.1 mol) 2-methyl-1,4-dibromobutane were placed into a 150 ml three-necked flask, 15.3 g (0.11 mol) K$_2$CO$_3$ and 155 mg tetrabutylammonium bromide were added and stirred, the mixture was heated to 65° C.~85° C. in an oil bath for 16 h~24 h; suction filtration was conducted to remove the solid which was washed with ethyl ether (30 ml×3 times), the filtrate was combined, and the organic layer was washed with water (40 ml×3 times) and then dried over MgSO$_4$ for 4 h~8 h, the solvent was distilled under reduced pressure, and then distilled under reduced pressure using an oil pump, 9.65 g of fraction at 145° C.~156° C. under the vacuum degree of 7 mmHg was collected, with the yield of 31.23%.

Step 2: diethyl 2-(3-methyl-4-diethylaminobutyl)-malonate

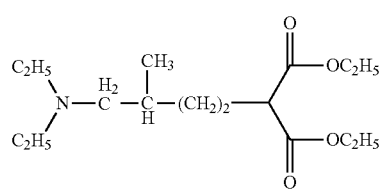

123.6 g (0.4 mol) diethyl 3-methyl-4-bromobutyl-malonate was placed into a three-necked flask, 55.6 g (0.4 mol) anhydrous K$_2$CO$_3$ and 500 ml acetonitrile were added and stirred. 73.3 g (1.0 mol) diethylamine was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 105.7 g of light yellow, light red, transparent substance which was purified by column chromatography, to obtain 49.75 g pure product, with the yield of 41.32%.

Step 3: disodium 2-(3-methyl-4-diethylaminobutyl) malonate

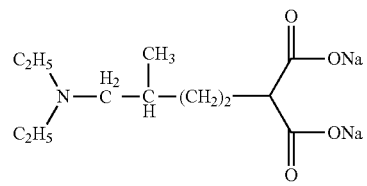

2M NaOH solution was obtained by dissolving 212.1 mg (5 mmol) NaOH with 2.5 mL water. 602 mg (2 mmol) diethyl 2-(4-diethylaminobutyl)-malonate was placed into a 20 mL three-necked flask and the above NaOH solution was added thereto, stirring at room temperature for 45 h~60 h, to obtain a solution of disodium 2-(4-diethylaminobutyl)-malonate.

Steps 4, 5 are the same as steps 4, 5 in [Example 1], respectively.

Step 6: 2-(3-methyl-4-diethylaminobutyl)-malonate•cis-diamine platinum (II) acetate

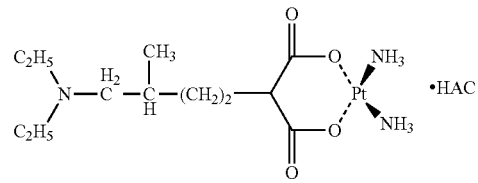

The pH of disodium [2-(3-methyl-4-diethylaminobutyl)-malonate solution was adjusted to 5~7 with 1M HAC and then cis-diamine•dihydrated platinum (II) sulphate aqueous solution was poured into the reaction solution, with the protection of N$_2$, the mixture was heated to 40° C.~75° C. in a water bath for 4 h-6 h, and the reaction solution was concentrated to a certain volume after suction filtration and stayed, to obtain 137 mg crystalline-type product.

The compound in Example 8 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 30.71% (theoretical 30.51%), H, 5.63% (theoretical 5.72%), N, 8.99% (theoretical 8.90%).

$^1$HNMR (D$_2$O) (ppm): δ3.52 (m, 1H), δ2.79-2.67 (b, 4H), δ2.57-2.67 (b, 2H), δ1.80 (m, 1H), δ1.45 (m, 2H), δ1.25 (m, 2H), δ1.15 (d, 3H), δ1.05 (t, 6H).

[Example 9]: 2-(4-(1-piperidyl)-butyl)-malonate•cis-(1,2-trans-cyclohexanediamine) platinum (II) tosilate Step 1 is the same as step 1 in [Example 1].
Steps 2, 3 are the same as steps 2, 3 in [Example 4], respectively.
Steps 4, 5 are the same as steps 4, 5 in [Example 3], respectively.

Step 6: 2-(4-(1-piperidyl)-butyl)-malonate•cis-(1,2-trans-cyclohexanediamine) platinum (II) tosilate

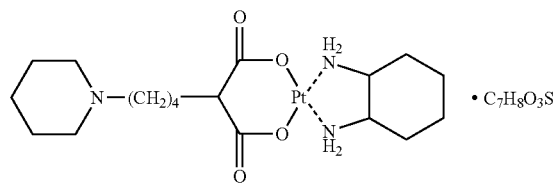

The pH of disodium 2-(4-(1-piperidyl)-butyl)malonate solution was adjusted to 5~7 with 1 M p-toluenesulfonic acid and then trans-cyclohexanediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture was treated by column chromatography to obtain 168 mg product.

The compound in Example 9 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 39.46% (theoretical 39.27%), H, 6.22% (theoretical 6.0%), N, 7.73% (theoretical 7.64%).

$^1$HNMR (D$_2$O) (ppm): δ3.52 (m, 1H), δ2.78-2.65 (br, 4H), δ2.67-2.56 (br, 2H), δ2.51 (m, 2H), δ2.02 (m, 4H), δ1.86 (m, 2H), δ1.75 (m, 4H), δ1.45 (m, 2H), δ1.32 (m, 2H), δ1.21 (m, 4H), δ1.11 (t, 2H).

[Example 10]: 2-(4-(2-methyl-1-tetrahydropyrrolidinyl)-butyl)-malonate•cis-diamine platinum (II) phosphate
Step 1 is the same as step 1 in [Example 3].

Step 2: diethyl 2-(4-(2-methyl-1-tetrahydropyrrolidinyl)-butyl)-malonate

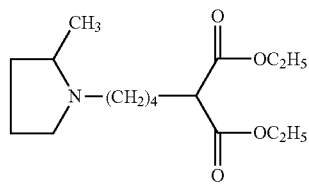

118 g (0.4 mol) diethyl 4-bromobutyl-malonate was placed into a three-necked flask, 55.6 g (0.4 mol) anhydrous K$_2$CO$_3$ and 500 ml acetonitrile were added and stirred. 85.1 g (1.0 mol) 2-methyl tetrahydropyrrolidine solution was added in the reaction solution (wherein 2-methyl tetrahydropyrrolidine can be racemic, or can be in R-configuration or S-configuration), and the mixture was heated to 40° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 110.5 g of light yellow, light red, transparent substance which was purified by column chromatography, to obtain 39.1 g pure product, with the yield of 32.69%.

Step 3: disodium 2-(4-(2 methyl-1-tetrahydropyrrolidinyl)-butyl)-malonate

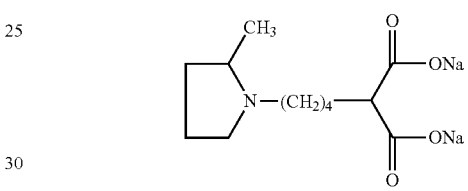

2M NaOH solution was obtained by dissolving 212.3 mg (5 mmol) NaOH with 2.5 mL water. 598 mg (2 mmol) diethyl 2-(4-(2-methyl-1-tetrahydropyrrolidinyl)-butyl)-malonate was placed into a 20 mL three-necked flask and the above NaOH solution was added thereto, stirring at room temperature for 45 h~60 h, to obtain a solution of disodium 2-(4-(2-methyl-1-tetrahydropyrrolidinyl)-butyl)-malonate.
Steps 4, 5 are the same as steps 4, 5 in [Example 1], respectively.

Step 6: 2-(4-(2-methyl-1-tetrahydropyrrolidinyl)-butyl)-malonate•cis-diamine platinum (II) phosphate

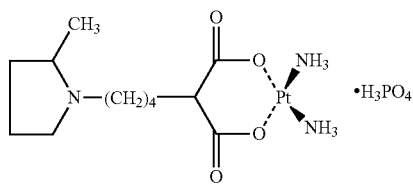

The pH of disodium 2-(4-(2-methyl-1-tetrahydropyrrolidinyl)-butyl)-malonate solution was adjusted to 5~7 with 1M H$_3$PO$_4$ and then cis-diamine•dihydrated platinum (II) sulphate aqueous solution was poured into the reaction solution, with the protection of N$_2$, the mixture was heated to 40° C.~75° C. in a water bath for 4 h-6 h, and the reaction solution was concentrated to a certain volume after suction filtration and stayed, to obtain 128 mg crystalline-type product (which is in racemic configuration, or can be in R-configuration or S-configuration of which the solubility is equivalent to that of the racemic configuration).

The compound in Example 10 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 35.62% (theoretical 35.47%), H, 6.26% (theoretical 6.16%), N, 10.39% (theoretical 10.34%).

$^1$HNMR (D$_2$O) (ppm): δ3.61 (t, 1H), δ2.85 (t, 2H), δ2.72 (m, 1H), δ2.61 (t, 2H), δ1.84 (m, 2H), δ1.78 (m, 2H), δ1.67 (m, 2H), δ1.45 (m, 2H), δ1.27 (d, 3H), δ1.12 (m, 2H).

[Example 11]: 2-(4-aminobutyl)-malonate•cis-(1,2-trans-cyclohexanediamine) platinum (II) phosphate Step 1 is same as step 1 in [Example 1].

Step 2: diethyl 2-(4-aminobutyl)-malonate

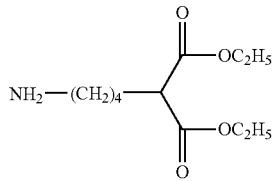

118 g (0.4 mol) diethyl 2-bromobutyl-malonate was placed into a three-necked flask, 55 g (0.4 mol) anhydrous K$_2$CO$_3$ and 500 ml acetonitrile were added and stirred. Excessive ammonia gas is inlet into the reaction solution, and the mixture was heated to 40° C.~50° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 80.5 g of light yellow, light red, transparent substance which was purified by column chromatography to obtain 36.5 g pure product, with the yield of 39.5%.

Step 3: disodium 2-(4-aminobutyl)-malonate

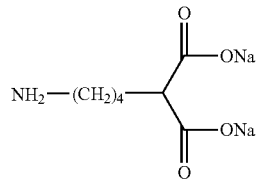

2M NaOH solution was obtained by dissolving 215 mg (5 mmol) NaOH with 2.5 mL water. 462 mg (2 mmol) diethyl 2-(4-aminobutyl)-malonate was placed into a 20 mL three-necked flask and the above NaOH solution was added thereto, stirring at room temperature for 45 h~60 h, to obtain a solution of disodium 2-(4-aminobutyl) malonate.

Steps 4, 5 are the same as steps 4, 5 in [Example 3], respectively.

Step 6: 2-(4-aminobutyl)-malonate•cis-(1,2-trans-cyclohexanediamine) platinum (II) phosphate

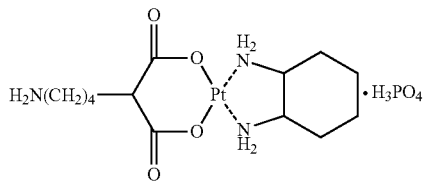

The pH of disodium 2-(4-aminobutyl)-malonate solution was adjusted to 5~7 with 1M H$_3$PO$_4$ and then trans-cyclohexanediamine•dihydrated platinum (II) sulphate aqueous solution was poured into the reaction solution, with the protection of N$_2$, the mixture was heated to 40° C.~60° C. in a water bath for 4 h-8 h, and the reaction solution is added into 2.5 g silica gel for column chromatography (200-300 meshes) and stirred for 15 min and then pumped to be dryness, the mixture is treated by column chromatography to obtain 151 mg product.

The compound in Example 11 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 32.32% (theoretical 32.37%), H, 4.95% (theoretical 5.19%), N, 8.97% (theoretical 8.71%).

$^1$HNMR (D$_2$O) (ppm): δ3.61 (t, 1H), δ2.78 (t, 2H), δ2.06 (br, 2H), δ1.81 (m, 2H), δ1.74 (m, 2H), δ1.46 (m, 2H), δ1.33 (m, 2H), δ1.21 (br, 2H), δ1.11 (m, 2H), δ1.01 (m, 2H).

[Example 12]: 2-(4-ethyl aminobutyl)-malonate•cis-(1, 2-trans-cyclohexanediamine) platinum (II) phosphate Step 1 is the same as step 1 in [Example 1].

Step 2: diethyl 2-(4-ethylaminobutyl)-malonate

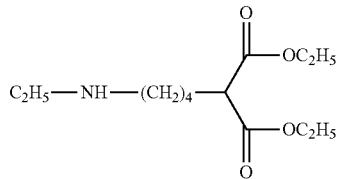

118 g (0.4 mol) diethyl 4-bromobutyl-malonate was placed into a three-necked flask, 55.2 g (0.4 mol) anhydrous K$_2$CO$_3$ are 500 ml acetonitrile were added and stirred. 45 g (1.0 mol) refrigerated ethylamine was added in the reaction solution, and the mixture was heated to 40° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 87.7 g of light yellow, light red, transparent substance which was purified by column chromatography to obtain 38.6 g pure product, with the yield of 37.26%.

Step 3: disodium 2-(4-ethylaminobutyl)-malonate

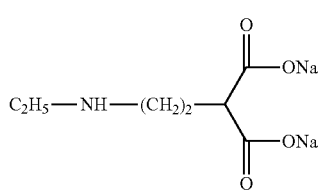

2M NaOH solution was obtained by dissolving 214 mg (5 mmol) NaOH with 2.5 mL water. 518 mg (2 mmol) diethyl 2-(4-aminobutyl)-malonate was placed into a 20 mL three-necked flask and the above NaOH solution was added thereto, stirring at room temperature for 45 h~60 h, to obtain a solution of disodium 2-(4-ethylaminobuty)-malonate.

Steps 4, 5 are the same as steps 4, 5 in [Example 3], respectively.

Step 6: 2-(4-ethylaminobutyl)-malonate•cis-(1,2-trans-cyclohexanediamine) platinum (II) phosphate

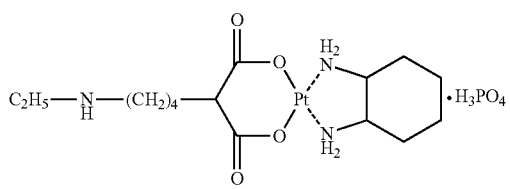

The pH of disodium 2-(4-ethylaminobutyl)-malonate solution was adjusted to 5~7 with 1M $H_3PO_4$ and then trans-cyclohexanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 151 mg product.

The compound in Example 12 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 35.55% (theoretical 35.29%), H, 5.71% (theoretical 5.69%), N, 8.46% (theoretical 8.24%).

$^1$H NMR ($D_2O$) (ppm): δ3.61 (t, 1H), δ2.77 (q, 2H), δ2.71 (m, 2H), 2.07 (br, 2H), 1.81 (m, 2H), δ1.71 (m, 2H), 1.46 (m, 2H), 1.35 (m, 2H), 1.26 (m, 2H), 1.17 (br, 2H), δ1.07 (t, 3H) 1.01 (m, 2H).

[Example 13]: 2-[4-(N-methyl-N-isopropylamino) butyl]-malonate•cis diamine platinum (II) acetate Step 1 is the same as step 1 in [Example 1].

Step 2: diethyl 2-[4-(N-methyl-N-isopropylamino)butyl]-malonate

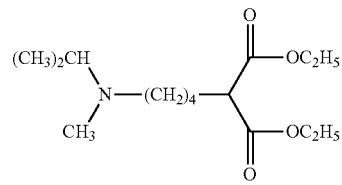

118.1 g (0.4 mol) diethyl 4-bromobutyl-malonate was placed into a three-necked flask, 55.5 g (0.4 mol) anhydrous $K_2CO_3$ and 500 ml acetonitrile were added and stirred. 73.1 g (1.0 mol) N-methylisopropylamine was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous $MgSO_4$ overnight, the solvent was pumped out under reduced pressure using a water pump, to obtain 105.3 g of light yellow, light red, transparent substance which was purified by column chromatography, to obtain 48.54 g pure product, with the yield of 42.28%.

Step 3: disodium 2-[4-(N-methyl-N-isopropylamino)butyl]-malonate

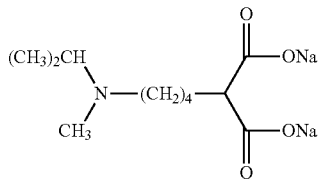

2M NaOH solution was obtained by dissolving 212 mg (5 mmol) NaOH with 2.5 mL water. 576 mg (2 mmol) diethyl 2-[4-(N-methyl-N-isopropylamino)butyl]-malonate was placed into a 20 mL three-necked flask and the above NaOH solution was added thereto, stirring at room temperature for 45 h~60 h, to obtain a solution of disodium 2-[4-(N-methyl-N-isopropylamino)butyl]-malonate.

Steps 4, 5 are the same as steps 4, 5 in [Example 1], respectively.

Step 6: 2-[4-(N-methyl-N-isopropylamino)butyl]-malonate•cis-diamine platinum (II) acetate

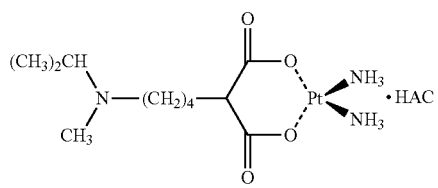

The pH of disodium 2-[4-(N-methyl-N-isopropylamino) butyl]-malonate solution was adjusted to 5~7 with 1M HAC and then cis-diamine•dihydrated platinum (II) sulphate aqueous solution was poured into the reaction solution, with the protection of $N_2$, the mixture is heated to 40° C.~75° C. in a water bath for 4 h-6 h, and the reaction solution was concentrated to a certain volume after suction filtration and stayed, to obtain 145 mg crystalline-type product.

The compound in Example 13 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 28.63% (theoretical 28.82%), H, 5.64% (theoretical 5.46%), N, 9.06% (theoretical 9.17%).

$^1$HNMR ($D_2O$) (ppm): δ3.51 (m, 1H), δ2.76-2.65 (b, 4H), δ2.65-2.57 (b, 2H), δ1.80 (m, 2H), δ1.45 (m, 2H), δ1.24 (m, 2H), δ1.05 (d, 6H).

[Example 14]: 2-(4-diethylaminobutyl)-malonate•cis-(1,2-trans-cyclopentanediamine) platinum (II) phosphate Steps 1, 2 and 3 are the same as steps 1, 2, and 3 in [Example 1], respectively.

Synthesis step 4: 1, 2-trans-cyclopentyldiamine

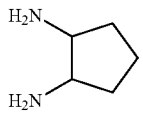

6.81 g (100 mmol) cyclopentene was placed in a 100 ml three-necked flask and dissolved with 30 ml dichloromethane by stirring, and 16.5 g (103 mmol) $Br_2$ was added dropwise slowly at −5° C.~10° C., the mixture is stirred for 1 h~3 h and washed with saturated sodium bicarbonate solution (10 ml×3 times), the organic layer was dried over anhydrous $MgSO_4$ for 2 h~3 h, the solvent was pumped out under reduced pressure using a water pump, to obtain 20.56 g 1,2-trans-dibromocyclopentane as a light yellow, transparent substance, with the yield of 90.18%. Elemental analysis: C, 26.51% (theoretical 26.32%), H, 3.62% (theoretical 3.51%).

11.5 g (50 mmol) 1, 2-trans-dibromocyclopentane was placed into a 100 ml autoclave and 30 ml ethanol solution containing 30% ammonia was added thereto, and the mixture was heated to 40° C.~60° C. to react for 6 h~8 h, the solvent was distilled off, to obtain 4.015 g 1,2-trans-cyclopentylamine as a light yellow, transparent substance, with the yield of 79.6%. Elemental analysis: C, 60.21% (theoretical 60%), H, 12.12% (theoretical 12%), N, 28.21% (theoretical 28%).

Step 5: 1,2-trans-cyclopentanediamine•diiodoplatinum (II)

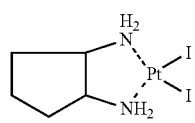

2.073 g (5 mmol) potassium tetrachloroplatinate ($K_2PtCl_4$) was added in 50 ml water and dissolved by stirring at room temperature, and 6.63 g (40 mmol) KI was added in the reaction solution after being dissolved with 50 ml water, with the protection of $N_2$ and away from light, the mixture was heated in a water bath to 40° C.~60° C. for 0.5 h~2 h. Then 501 mg (5 mmol) 1, 2-trans-cyclopentanediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.561 g product, with the yield of 93.3%. Elemental analysis: C, 10.78% (theoretical 10.93%), H, 2.31% (theoretical 2.19%), N, 4.98% (theoretical 5.10%).

Step 6: 1,2-trans-cyclopentanediamine•dihydrated platinum (II) sulphate

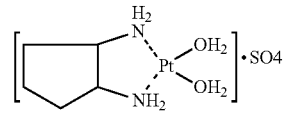

625 mg (2 mmol) $Ag_2SO_4$ was placed in a 100 ml three-necked flask, 30 ml water was added thereto and stirred, and 1.10 g (2 mmol) 1,2-trans-cyclopentanediamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 7: 2-(4-diethylaminobutyl)-malonate•cis-(1,2-trans-cyclopentanediamine) platinum (II) phosphate

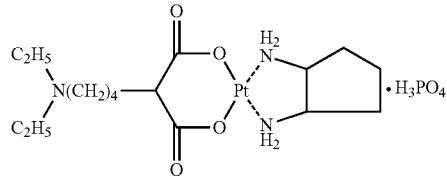

The pH of disodium 2-(4-diethylaminobutyl)-malonate solution was adjusted to 5~7 with 1M $H_3PO_4$ and then 1,2-trans-cyclohexanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 153 mg product.

The compound in Example 14 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 36.57% (theoretical 36.64%), H, 5.73% (theoretical 5.92%), N, 8.17% (theoretical 8.02%).

$^1$HNMR (D$_2$O) (ppm): δ3.61 (t, 1H), δ2.77 (q, 4H), δ2.68 (t, 2H), δ2.07 (br, 2H), δ1.83 (m, 2H), δ1.72 (m, 2H), δ1.48 (m, 2H), δ1.40 (m, 2H), δ1.17 (m, 2H), δ1.08 (t, 6H), δ1.02 (m, 2H).

[Example 15]: 2-(4-diethylaminobutyl)-malonate•cis-(1,2-trans-cyclobutanediamine) platinum (II) succinate Steps 1, 2 and 3 are the same as steps 1, 2 and 3 in [Example 1], respectively.

Step 4: 1,2-trans-cyclobutanediamine

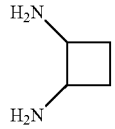

5.39 g (100 mmol) cyclobutene was placed in a 100 ml three-necked flask and dissolved with 30 ml dichloromethane by stirring, and 16.5 g (103 mmol) Br$_2$ was added dropwise slowly at −5° C.~10° C., the mixture is stirred for 1 h~3 h, and washed with saturated sodium bicarbonate solution (10 ml×3 times), the organic layer was dried over anhydrous MgSO$_4$ for 2 h~3 h, the solvent was pumped out under reduced pressure using a water pump, to obtain 20.37 g 1,2-trans-dibromocyclobutane as a light yellow, transparent substance, with the yield of 95.19%. Elemental analysis: C, 22.53% (theoretical 22.43%), H, 2.61% (theoretical 2.80%).

10.65 g (50 mmol) 1, 2-trans-dibromocyclobutane was placed into a 100 ml pressure autoclave and 30 ml ethanol solution containing 30% ammonia was added thereto, and the mixture was heated to 40° C.~60° C. to react for 6 h~8 h, the solvent was distilled off, to obtain 3.723 g 1,2-trans-cyclobutylamine as a light yellow, transparent substance, with the yield of 86.58%. Elemental analysis: C, 55.57% (theoretical 55.81%); H, 11.90% (theoretical 11.63%); N, 32.17% (theoretical 32.56%).

Step 5: 1,2-trans-cyclobutanediamine•diiodoplatinum (II)

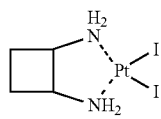

2.075 g (5 mmol) potassium tetrachloroplatinate (K$_2$PtCl$_4$) was added in 50 ml water and dissolved by stirring at room temperature, and 6.63 g (40 mmol) KI was added in the reaction solution after being dissolved with 50 ml water, with the protection of N$_2$ and away from light, the mixture was heated to 40° C.~60° C. in a water bath for 0.5 h~2 h. Then 431 mg (5 mmol) 1, 2-trans-cyclobutanediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.429 g product, with the yield of 90.8%.

Elemental analysis: C, 8.75% (theoretical 8.97%), H, 1.91% (theoretical 1.87%), N, 5.98% (theoretical 5.23%).

Step 6: 1,2 trans-cyclobutanediamine•dihydrated platinum (II) sulphate

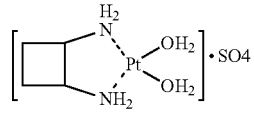

627 mg (2 mmol) Ag$_2$SO$_4$ was placed in a 100 ml three-necked flask, 30 ml water was added thereto and stirred, and 1.07 g (2 mmol) 1,2-trans-cyclobutanediamine•diiodoplatinum (II) was added into the reaction solution and then 40 ml water was added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 7: 2-(4-diethylaminobutyl)-malonate•cis-(1,2-trans-cyclobutanediamine) platinum (II) succinate

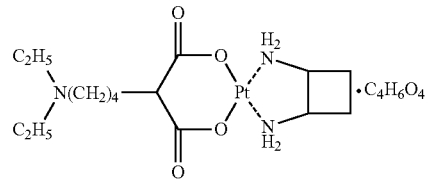

The pH of disodium 2-(4-diethylaminobutyl)-malonate solution was adjusted to 5~7 with 1M succinic acid C$_4$H$_6$O$_4$ and then 1,2-trans-cyclobutanediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 148 mg product.

The compound in Example 15 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 35.57% (theoretical 35.29%), H, 5.65% (theoretical 5.69%), N, 8.38% (theoretical 8.24%).

$^1$HNMR (D$_2$O) (ppm): δ3.61 (t, 1H), δ2.78 (q, 4H), δ2.67 (t, 2H), δ2.09 (br, 2H), δ1.82 (m, 2H), δ1.72 (m, 2H), δ1.45 (m, 2H), δ1.38 (m, 2H), δ1.15 (m, 2H), δ1.06 (t, 6H).

[Example 16]: 2-(4-diethylaminobutyl)-malonate•cis-(1, 2-trans-cyclopropanediamine) platinum (II) phosphate Steps 1, 2 and 3 are the same as steps 1, 2 and 3 in [Example 1], respectively.

Step 4:
1,2-trans-cyclopropanediamine•diiodoplatinum (II)

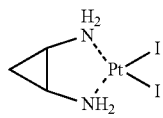

2.075 g (5 mmol) potassium tetrachloroplatinate (K$_2$PtCl$_4$) was added in 50 ml water and dissolved by stirring at room temperature, and 6.63 g (40 mmol) KI was added in the reaction solution after being dissolved with 50 ml water, with the protection of N$_2$ and away from light, the mixture was heated to 40° C.~60° C. in a water bath for 0.5 h~2 h. 361 mg (5 mmol) 1,2-trans-cyclopropanediamine (commercially available) was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.391 g product, with the yield of 91.8%. Elemental analysis: C, 6.97% (theoretical 6.91%), H, 1.41% (theoretical 1.54%), N, 5.47% (theoretical 5.37%).

Step 5: 1,2-trans-cyclopropanediamine•dihydrated platinum (II) sulphate

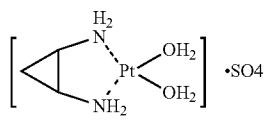

624 mg (2 mmol) Ag$_2$SO$_4$ was placed in a 100 ml three-necked flask, 30 ml water was added thereto and stirred, and 1.04 g (2 mmol) 1,2-trans-cyclopentanediamine•diiodoplatinum (II) was added into the reaction solution and then 40 ml water was added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1,2-trans-cyclopropanediamine) platinum (II) phosphate

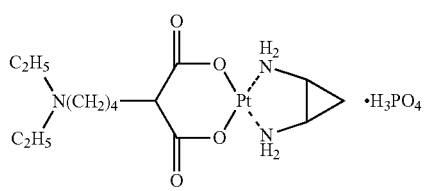

The pH of disodium 2-(4-diethylaminobutyl)-malonate solution was adjusted to 5~7 with 1M H$_3$PO$_4$ and then 1,2-trans-cyclopropanediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 135 mg product.

The compound in Example 16 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 33.63% (theoretical 33.87%), H, 5.32% (theoretical 5.44%), N, 8.59% (theoretical 8.47%).

$^1$HNMR (D$_2$O) (ppm): δ3.62 (t, 1H), δ2.79 (q, 4H), δ2.66 (t, 2H), δ2.08 (br, 2H), δ1.82 (m, 2H), δ1.45 (m, 2H), δ1.38 (m, 2H), δ1.15 (m, 2H), δ1.07 (t, 6H).

[Example 17]: 2-(4-diethylaminobutyl)-malonate•cis-(1,2-ethylenediamine) platinum (II) tosilate Steps 1, 2 and 3 are the same as steps 1, 2 and 3 in [Example 1], respectively.

Step 4: 1, 2-ethylenediamine•diiodoplatinum (II)

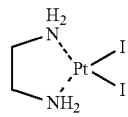

2.076 g (5 mmol) potassium tetrachloroplatinate (K$_2$PtCl$_4$) was added in 50 ml water and dissolved by stirring at room temperature, and 6.64 g (40 mmol) KI was added in the reaction solution after being dissolved with 50 ml water, with the protection of N$_2$ and away from light, the mixture was heated to 40° C.~60° C. in a water bath for 0.5 h~2 h. Then 301 mg (5 mmol) refrigerated 1, 2-ethylenediamine (commercially available) was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.254 g product, with the yield of 89.8%. Elemental analysis: C, 4.77% (theoretical 4.72%), H, 1.41% (theoretical 1.57%), N, 5.41% (theoretical 5.50%).

Step 5: 1,2-ethylenediamine•dihydrated platinum (II) sulphate

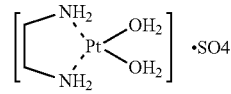

625 mg (2 mmol) Ag$_2$SO$_4$ was placed in a 100 ml three-necked flask, 30 ml water was added thereto and stirred, and 1.020 g (2 mmol) 1,2-ethylenediamine•diiodoplatinum (II) was added into the reaction solution and then 40 ml water was added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1,2-ethylenediamine) platinum (II) tosilate

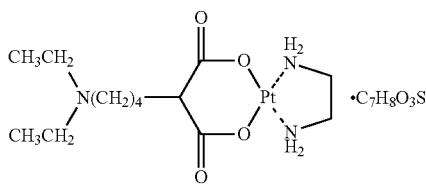

The pH of disodium 2-(4-diethylaminobutyl)-malonate solution was adjusted to 5~7 with 1M p-toluenesulfonic acid $C_7H_8O_3S$ and then 1,2-ethylenediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 148 mg product.

The compound in Example 17 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 32.35% (theoretical 32.23%), H, 5.33% (theoretical 5.58%), N, 8.90% (theoretical 8.68%).

$^1$HNMR ($D_2O$) (ppm): δ3.63 (t, 1H), δ2.68 (q, 4H), δ2.55 (t, 2H), δ2.31 (t, 4H), δ2.25 (m, 2H), δ1.86 (m, 2H), δ1.12 (m, 2H), δ1.06 (t, 6H).

[Example 18]: 2-(4-diethylaminobutyl)-malonate•cis-(1,3-propanediamine) platinum (II) phosphate Steps 1, 2 and 3 are the same as steps 1, 2, and 3 in [Example 1], respectively.

Step 4: 1,3-propanediamine•diiodoplatinum (II)

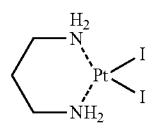

2.073 g (5 mmol) potassium tetrachloroplatinate ($K_2PtCl_4$) was added in 50 ml water and dissolved by stirring at room temperature, and 6.63 g (40 mmol) KI was added in the reaction solution after being dissolved with 50 ml water, with the protection of $N_2$ and away from light, the mixture was heated to 40° C.~60° C. in a water bath for 0.5 h~2 h. 372 mg (5 mmol) refrigerated 1,3-propanediamine (commercially available) was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.281 g product, with the yield of 87.6%. Elemental analysis: C, 6.77% (theoretical 6.88%), H, 1.79% (theoretical 1.91%), N, 5.43% (theoretical 5.35%).

Step 5: 1,3-propanediamine•dihydrated platinum (II) sulphate

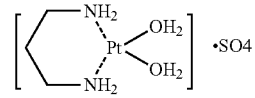

625 mg (2 mmol) $Ag_2SO_4$ was placed in a 100 ml three-necked flask, 30 ml water was added thereto and stirred, and 1.043 g (2 mmol) 1,2-ethylenediamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1,3-propanediamine) platinum (II) phosphate

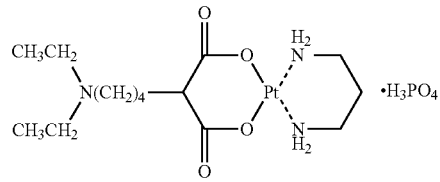

The pH of disodium 2-(4-diethylaminobutyl)-malonate solution was adjusted to 5~7 with 1M $H_3PO_4$ and then 1,2-ethylenediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 158 mg product.

The compound in Example 18 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 33.94% (theoretical 33.73%, H, 5.66% (theoretical 5.82%), N, 8.58% (theoretical 8.43%).

$^1$HNMR ($D_2O$) (ppm): δ3.61 (t, 1H), δ2.67 (q, 4H), δ2.56 (t, 2H), δ2.29 (t, 4H), δ2.21 (m, 2H), δ1.82 (m, 2H), δ1.42 (m, 2H), δ1.21 (m, 2H), δ1.04 (t, 6H).

[Example 19]: 2-(4-diethylaminobutyl)-malonate•cis-(1,4-butanediamine) platinum (II) phosphate Steps 1, 2 and 3 are the same as steps 1, 2 and 3 in [Example 1], respectively.

Step 4: 1,4-butanediamine•diiodoplatinum (II)

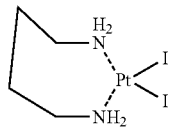

2.071 g (5 mmol) potassium tetrachloroplatinate (K$_2$PtCl$_4$) was added in 50 ml water and dissolved by stirring at room temperature, and 6.635 g (40 mmol) KI was added in the reaction solution after being dissolved with 50 ml water, with the protection of N$_2$ and away from light, the mixture was heated to 40° C.~60° C. in a water bath for 0.5 h~2 h. 431 mg (5 mmol) refrigerated 1,3-propanediamine (commercially available) was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.365 g product, with the yield of 88.1%. Elemental analysis: C, 8.69% (theoretical 8.94%), H, 2.39% (theoretical 2.23%), N, 5.44% (theoretical 5.21%).

Step 5: 1,4-butanediamine•dihydrated platinum (II) sulphate

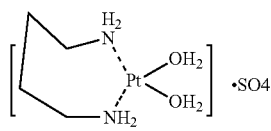

624 mg (2 mmol) Ag$_2$SO$_4$ was placed in a 100 ml three-necked flask, 30 ml water was added thereto and stirred, and 1.072 g (2 mmol) 1,2-ethylenediamine•diiodoplatinum (II) was added into the reaction solution and then 40 ml water was added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(1,4-butanediamine) platinum (II) phosphate

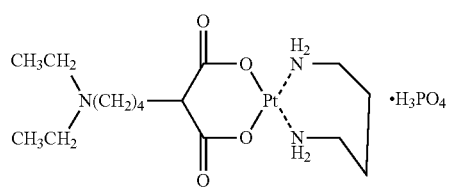

The pH of disodium 2-(4-diethylaminobutyl)-malonate solution was adjusted to 5~7 with 1M H$_3$PO$_4$ and then 1,2-ethylenediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 157 mg product.

The compound in Example 19 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 34.95% (theoretical 35.16%), H, 6.02% (theoretical 6.05%), N, 8.13% (theoretical 8.20%).

$^1$HNMR (D$_2$O) (ppm): δ3.62 (t, 1H), δ2.66 (q, 4H), δ2.54 (t, 2H), δ2.30 (t, 4H), δ2.20 (m, 2H), δ1.82 (m, 2H), δ1.41 (m, 2H), δ1.23 (m, 4H), δ1.05 (t, 6H).

[Example 20]: 2-(2-diethylaminobutyl)-malonate•cis-1,2-(1,2-dihydroxymethyl)-ethylenediamine platinum (II) phosphate Steps 1, 2 and 3 are the same as steps 1, 2 and 3 in [Example 1], respectively.

Step 4: 1, 2-(1, 2-dihydroxymethyl)-ethylenediamine•diiodoplatinum (II)

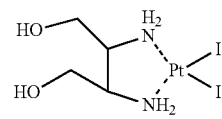

2.073 g (5 mmol) potassium tetrachloroplatinate (K$_2$PtCl$_4$) was added in 50 ml water and dissolved by stirring at room temperature, and 6.637 g (40 mmol) KI was added in the reaction solution after being dissolved with 50 ml water, with the protection of N$_2$ and away from light, the mixture was heated to 40° C.~60° C. in a water bath for 0.5 h~2 h. 601 mg (5 mmol) 1, 2-(1, 2-dihydroxymethyl)-ethylenediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.163 g product, with the yield of 79.96%. Elemental analysis: C, 8.65% (theoretical 8.44%), H, 2.39% (theoretical 2.11%), N, 5.03% (theoretical 4.92%).

Step 5: 1, 2-(1,2-dihydroxymethyl)-ethylenediamine•dihydrated platinum (II) sulphate

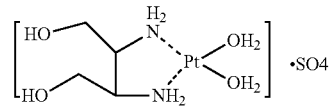

624 mg (2 mmol) Ag$_2$SO$_4$ was placed in a 100 ml three-necked flask, 30 ml water was added thereto and stirred, and 1.138 g (2 mmol) 1,2-(1,2-dihydroxymethyl)-ethylenediamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-1,2-(1,2-dihydroxymethyl)-ethylenediamine platinum (II) phosphate

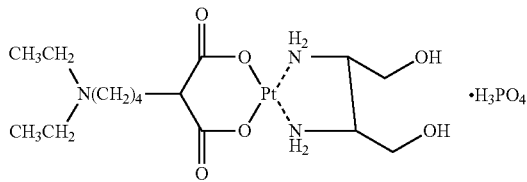

The pH of disodium 2-(4-diethylaminobutyl)-malonate solution was adjusted to 5~7 with 1M $H_3PO_4$ and then 1,2-(1,2-dihydroxymethyl)-ethylenediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 138 mg product.

The compound in Example 20 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 30.15% (theoretical 30.09%), H, 5.42% (theoretical 5.70%), N, 7.56% (theoretical 7.72%).

$^1$HNMR ($D_2O$) (ppm): δ3.88 (d, 4H), δ3.61 (t, 1H), δ3.03 (m, 2H), δ2.77 (q, 4H), δ2.57 (t, 2H), δ2.01 (m, 2H), δ1.45 (m, 2H), δ1.21 (m, 2H), δ1.06 (t, 6H).

[Example 21]: 2-(4-diethylaminobutyl)-malonate•cis-1,3-(2,2-hydroxymethyl)-propanediamine platinum (II) phosphate Steps 1, 2 and 3 are the same as steps 1, 2 and 3 in [Example 1], respectively.

Step 4: 1,3-(2,2-hydroxymethyl)-propanediamine•diiodoplatinum (II)

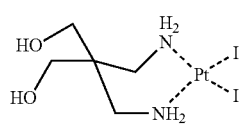

2.074 g (5 mmol) potassium tetrachloroplatinate ($K_2PtCl_4$) was added in 50 ml water and dissolved by stirring at room temperature, and 6.636 g (40 mmol) KI was added in the reaction solution after being dissolved with 50 ml water, with the protection of $N_2$ and away from light, the mixture was heated to 40° C.~60° C. in a water bath for 0.5 h~2 h. 671 mg (5 mmol) 1,3-(2,2-hydroxymethyl)-propanediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.163 g product, with the yield of 79.96%. Elemental analysis: C, 10.37% (theoretical 10.29%); H, 2.49% (theoretical 2.40%), N, 5.01% (theoretical 4.80%).

Step 5: 1,3-(2,2-hydroxymethyl)-propanediamine•dihydrated platinum (II) sulphate

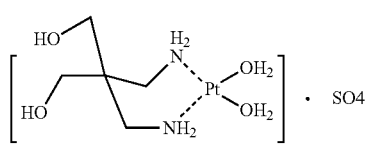

624 mg (2 mmol) $Ag_2SO_4$ was placed in a 100 ml three-necked flask, 30 ml water was added thereto and stirred, and 1.162 g (2 mmol) 1,3-(2,2-hydroxymethyl)-propanediamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-1,3-(2,2-hydroxymethyl)-propanediamine platinum (II) phosphate

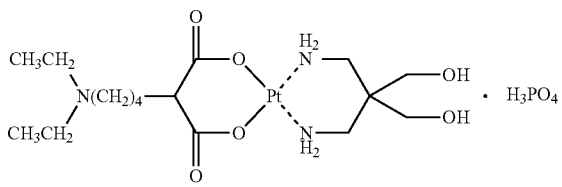

The pH of disodium 2-(4-diethylaminobutyl)-malonate solution was adjusted to 5~7 with 1M $H_3PO_4$ and then 1,3-(2,2-hydroxymethyl)-propanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 148 mg product.

The compound in Example 21 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 34.48% (theoretical 34.41%), H, 5.80% (theoretical 5.91%), N, 7.49% (theoretical 7.53%).

$^1$H NMR ($D_2O$) (ppm): δ3.78 (s, 4H), δ3.61 (t, 1H), δ2.76 (s, 4H), δ2.69 (t, 2H), δ2.56 (q, 4H), δ1.71 (m, 2H), δ1.44 (m, 2H), δ1.22 (m, 2H), δ1.03 (t, 6H).

[Example 22]: 2-(4-diethylaminobutyl)-malonate•cis-1,4-(trans-2,3-cyclobutyl)-butanediamine platinum (II) phosphate Steps 1, 2 and 3 are the same as steps 1, 2 and 3 in [Example 1], respectively.

Step 4:
2,3-diaminomethylcyclobutane•diiodoplatinum (II)

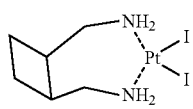

2.075 g (5 mmol) potassium tetrachloroplatinate (K$_2$PtCl$_4$) was added in 50 ml water and dissolved by stirring at room temperature, and 6.64 g (40 mmol) KI was added in the reaction solution after being dissolved with 50 ml water, with the protection of N$_2$ and away from light, the mixture was heated in to 40° C.~60° C. a water bath for 0.5 h~2 h. 571 mg (5 mmol) 1,4-(trans-2,3-cyclobutyl)-butanediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.251 g product, with the yield of 79.96%. Elemental analysis: C, 12.61% (theoretical 12.79%), H, 2.45% (theoretical 2.49%), N, 5.11% (theoretical 4.97%).

Step 5: 2,3-diaminomethylcyclobutane•dihydrated platinum (II) sulphate

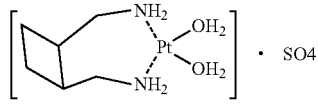

625 mg (2 mmol) Ag$_2$SO$_4$ was placed in a 100 ml three-necked flask, 30 ml water was added thereto and stirred, and 1.122 g (2 mmol) 2,3-diaminomethylcyclobutane•diiodoplatinum (II) was added into the reaction solution and then 40 ml water was added to react, with the protection of N$_2$ and away from light, the mixture was reacted in a water bath at 40° C.~60° C. for 4 h~8 h. After removing AgI precipitate by suction filtration, the filtrate was obtained, i.e., the aqueous solution of the product.

Step 6: 2-(4-diethylaminobutyl)-malonate•cis 1,4-(trans-2,3-cyclobutyl)-butanediamine platinum (II) phosphate

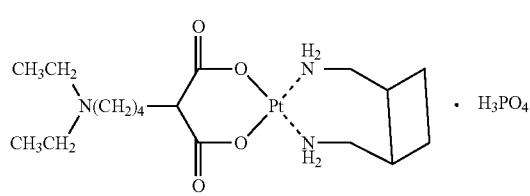

The pH of disodium 2-(2-dimethylaminoethyl)-malonate solution was adjusted to 5~7 with 1M H$_3$PO$_4$ and then 1,4-(trans-2,3-cyclobutyl)-butanediamine•dihydrated platinum (II) sulphate aqueous solution was poured into the reaction solution, with the protection of N$_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 147 mg product.

The compound in Example 22 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 37.79% (theoretical 37.92%), H, 6.36% (theoretical 6.13%), N, 7.76% (theoretical 7.81%).

$^1$HNMR (D$_2$O) (ppm): δ3.61 (t, 1H), δ2.76 (q, 4H), δ2.71 (t, 2H), δ2.23 (d, 4H), δ1.96 (m, 2H), δ1.71 (m, 2H), δ1.45 (m, 4H), δ1.25 (m, 2H), δ1.13 (m, 2H), δ1.04 (t, 6H)

[Example 23]: 2-(4-diethylaminobutyl)-malonate•cis-1,4-cyclohexanediamine platinum (II) phosphate Steps 1, 2 and 3 are the same as steps 1, 2 and 3 in [Example 1], respectively.

Step 4: 1,4-cyclohexanediamine•diiodoplatinum (II)

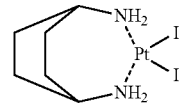

2.071 g (5 mmol) potassium tetrachloroplatinate (K$_2$PtCl$_4$) was added in 50 ml water and dissolved by stirring at room temperature, and 6.64 g (40 mmol) KI was added in the reaction solution after being dissolved with 50 ml water, with the protection of N$_2$ and away from light, the mixture was heated to 40° C.~60° C. in a water bath for 0.5 h~2 h. 572 mg (5 mmol) 1,4-cyclohexanediamine was added in the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.163 g product, with the yield of 76.84%. Elemental analysis: C, 12.74% (theoretical 12.79%), H, 2.45% (theoretical 2.49%), N, 5.17% (theoretical 4.97%).

Step 5: 1,4-cyclohexanediamine•dihydrated platinum (II) sulphate

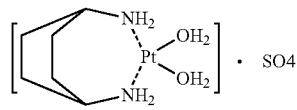

623 mg (2 mmol) Ag$_2$SO$_4$ was placed in a 100 ml three-necked flask, 30 ml water was added thereto and stirred, and 1.125 g (2 mmol) 1,4-cyclohexanediamine•diiodoplatinum (II) was added into the reaction solution and then 40 ml water was added to react, with the protection of N$_2$ and away from light, the mixture was reacted at 40° C.~60° C. in a water bath for 4 h~8 h.

After removing AgI precipitate by suction filtration, the filtrate was obtained, i.e., the aqueous solution of the product.

Step 6: 2-(4-diethylaminobutyl)-malonate•cis-1,4-cyclohexanediamine platinum (II) phosphate

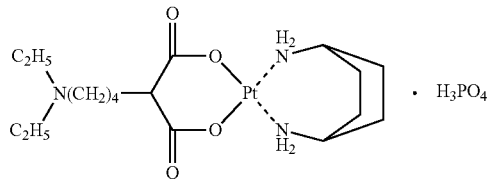

The pH of disodium 2-(4-diethylaminobutyl)-malonate solution was adjusted to 5~7 with 1M $H_3PO_4$ and then 1,4-cyclohexanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 151 mg product.

The compound in Example 23 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 37.81% (theoretical 37.92%), H, 5.97% (theoretical 6.13%), N, 8.02% (theoretical 7.81%).

$^1$HNMR ($D_2O$) (ppm): δ3.61 (t, 1H), δ2.79 (q, 4H), δ2.69 (t, 2H), 2.05 (m, 2H), δ1.81 (m, 2H), δ1.78-1.51 (m, 8H), δ1.41 (m, 2H), δ1.23 (m, 2H), δ1.08 (t, 6H).

[Example 24]: 2-(4-diethylaminobutyl)-malonate•cis-1,3-(2,2-(4-oxacyclohexyl))-propanediamine•platinum (II) phosphate Step 1, 2 and 3 are same as steps 1, 2 and 3 in [Example 1], respectively.

Step 4: 1,3-(2,2-(4-oxacyclohexyl))-propanediamine•diiodoplatinum (II)

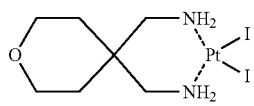

2.071 g (5 mmol) potassium tetrachloroplatinate ($K_2PtCl_4$) was added in 50 ml water and dissolved by stirring at room temperature, and 6.64 g (40 mmol) KI was added in the reaction solution after being dissolved with 50 ml water, with the protection of $N_2$ and away from light, the mixture was heated in to 40° C.~60° C. a water bath for 0.5 h~2 h. 722 mg (5 mmol) 1,3-(2,2-(4-oxacyclohexyl))-propanediamine was added into the reaction solution after being dissolved with 50 ml water, which was kept under this condition to react for 0.5 h~2 h. A yellow solid product was obtained by suction filtration and washed with water (10 ml×3 times) and ethyl ether (10 ml×3 times), to obtain 2.547 g product, with the yield of 85.91%. Elemental analysis: C, 14.35% (theoretical 14.17%), H, 2.75% (theoretical 2.70%), N, 4.72% (theoretical 4.72%).

Step 5: 1,3-(2,2-(4-oxacyclohexyl))-propanediamine•dihydrated platinum (II) sulphate

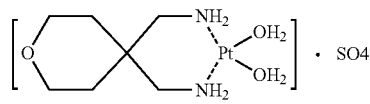

623 mg (2 mmol) $Ag_2SO_4$ was placed in a 100 ml three-necked flask, 30 ml water was added thereto and stirred, and 1.185 g (2 mmol) 1,3-(2,2-(4-oxacyclohexyl))-propanediamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-1,3-(2,2-(4-oxacyclohexyl)-propanediamine•platinum (II) phosphate

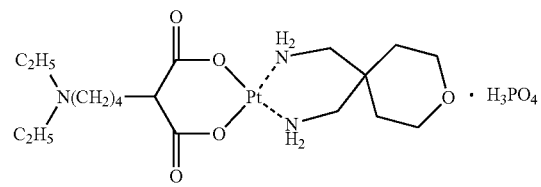

The pH of disodium 2-(2-diethylaminoethyl)-malonate solution was adjusted to 5~7 with 1M $H_3PO_4$ and then 1,3-(2,2-(4-oxacyclohexyl))-propanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture is treated by column chromatography to obtain 167 mg product.

The compound in Example 24 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 38.22% (theoretical 38.03%), H, 6.35% (theoretical 6.16%), N, 7.42% (theoretical 7.39%).

$^1$HNMR ($D_2O$) (ppm): δ3.71 (t, 4H), δ3.61 (t, 1H), δ2.77 (q, 4H), δ2.69 (t, 2H), δ2.11 (s, 4H), δ1.88 (m, 2H), δ1.51 (t, 4H), δ1.40 (m, 2H), δ1.21 (m, 2H), δ1.03 (t, 6H).

[Example 25]: 2-(4-diethylaminobutyl)-malonate•cis-dicyclopentylamine platinum (II) acetate Steps 1, 2 and 3 are the same as steps 1, 2 and 3 in [Example 1], respectively.

Step 4: dicyclopentylamine•diiododiamine (II)

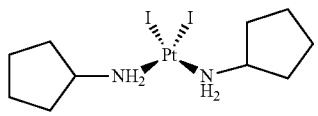

2.075 g (5 mmol) potassium tetrachloroplatinate (K$_2$PtCl$_4$) was added in 50 ml water and dissolved by stirring at room temperature, and 6.640 g (40 mmol) KI was added in the reaction solution after being dissolved with 50 ml water, with the protection of N$_2$ and away from light, the mixture was heated in to 40° C.~60° C. a water bath for 0.5 h~2 h. 50 ml cyclopropantylamine (containing 5 mmol ammonia) solution was added in the reaction solution, which was kept under this condition to react for 0.5 h~2 h. A light yellow solid product was obtained by suction filtration and washed with water (10 ml×3 times) and ethyl ether (10 ml×3 times), to obtain 2.903 g product, with the yield of 93.8%. Elemental analysis: C, 19.24% (theoretical 19.39%), H, 3.37% (theoretical 3.55%), N, 6.58% (theoretical 6.79%).

Step 5: dicyclopentylamine•dihydrated platinum (II) sulphate

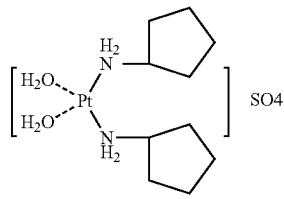

625 mg (2 mmol) Ag$_2$SO$_4$ was placed in a 100 ml three-necked flask, 30 ml water was added thereto and stirred, and 1.238 g (2 mmol) dicyclopentylamine•diiododiamine (II) was added into the reaction solution and then 40 ml water was added to react, with the protection of N$_2$ and away from light, the mixture was reacted in a water bath at 40° C.~60° C. for 4 h~8 h. After removing AgI precipitate by suction filtration, the filtrate was obtained, i.e., the aqueous solution of the product.

Step 6: 2-(4-diethylaminobutyl)-malonate•cis-dicyclopentylamine platinum (II) acetate

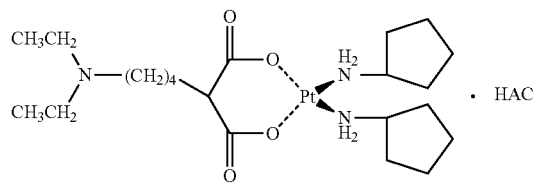

The pH of disodium 2-(4-diethylaminobutyl)-malonate solution was adjusted to 5~7 with 1M H$_3$PO$_4$ and then cis-diamine•dihydrated platinum (II) sulphate aqueous solution was poured into the reaction solution, with the protection of N$_2$, the mixture was heated to 40° C.~75° C. in a water bath for 4 h-6 h, and the reaction solution was concentrated to a certain volume after suction filtration and stayed, to obtain 165 mg crystalline-type product.

The compound in Example 25 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 42.42% (theoretical 42.42%), H, 6.67% (theoretical 6.90%), N, 7.08% (theoretical 7.07%).

$^1$HNMR (D$_2$O) (ppm): δ3.52 (m, 1H), δ2.79 (q, 4H), δ2.67 (m, 2H), δ2.57 (t, 2H), δ2.22 (m, 8H), δ1.80 (m, 2H), δ1.45 (m, 2H), δ1.36 (m, 8H), δ1.24 (m, 2H), δ1.05 (t, 6H).

[Example 26]: 2-(4-diethylaminobutyl)-malonate•cis-ammonia•cyclopentylamine platinum (II) acetate Steps 1, 2 and 3 are the same as steps 1, 2 and 3 in [Example 1], respectively.

Step 4: ammonia•cyclopentylamine•diiodoplatinum

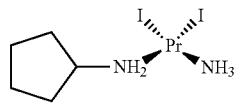

2.076 g (5 mmol) potassium tetrachloroplatinate (K$_2$PtCl$_4$) was added in 50 ml water and dissolved by stirring at room temperature, and 6.65 g (40 mmol) KI was added in the reaction solution after being dissolved with 50 ml water, with the protection of N$_2$ and away from light, the mixture was heated to 40° C.~60° C. in a water bath for 0.5 h~2 h. 25 ml cyclopropantylamine (containing 2.5 mmol ammonia) solution was added in the reaction solution, which was kept under this condition to react for 0.5 h~2 h, and then 25 ml ammonia water (containing 2.5 mmol ammonia) was added in the reaction solution, which was kept under this condition to react for 0.5 h~2 h. A light yellow solid product was obtained by suction filtration and washed with water (10 ml×3 times) and ethyl ether (10 ml×3 times), to obtain 2.43 g product, i.e., ammonia•cyclopentylamine•diiodoplatinum (II), with the yield of 88.2%. Elemental analysis: C, 10.76% (theoretical 10.89%), H, 2.31% (theoretical 2.54%), N, 5.18% (theoretical 5.08%).

Step 5: ammonia•cyclopentylamine•dihydrated platinum (II) sulphate

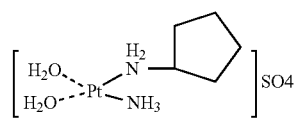

625 mg (2 mmol) Ag$_2$SO$_4$ was placed in a 100 ml three-necked flask, 30 ml water was added thereto and stirred, and 1.1 g (2 mmol) ammonia•cyclopentylamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-ammonia•cyclopentylamine platinum (II) acetate

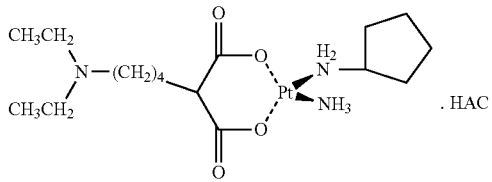

The pH of disodium 2-(4-diethylaminobutyl)-malonate solution was adjusted to 5~7 with 1M HAC and then cis-ammonia•cyclopentylamine•diiodoplatinum (II) sulphate aqueous solution was poured into the reaction solution, with the protection of $N_2$, the mixture was heated to 40° C.~75° C. in a water bath for 4 h~6 h, and the reaction solution was concentrated to a certain volume after suction filtration and stayed, to obtain 156 mg crystalline-type product.

The compound in Example 26 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 36.43% (theoretical 36.50%), H, 6.28% (theoretical 6.27%), N, 7.87% (theoretical 7.99%).

$^1$HNMR ($D_2O$) (ppm): δ3.62 (m, 1H), δ2.80 (q, 4H), δ2.67 (m, 1H), δ2.58 (t, 2H), δ2.21 (m, 4H), δ1.80 (m, 2H), 51.45 (m, 2H), δ1.36 (m, 4H), δ1.24 (m, 2H), δ1.05 (t, 6H).

[Example 27]: 2-(4-diethylaminobutyl)-malonate•cis-(2-aminomethyl-cyclopentylamine) platinum (II) acetate Steps 1, 2 and 3 are the same as steps 1, 2 and 3 in [Example 1], respectively.

Step 4: 2-aminomethyl-cyclopentylamine•diiodoplatinum (II)

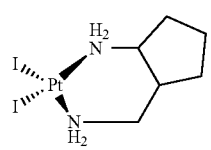

2.075 g (5 mmol) potassium tetrachloroplatinate ($K_2PtCl_4$) was added in 50 ml water and dissolved by stirring at room temperature, and 6.65 g (40 mmol) KI was added in the reaction solution after being dissolved with 50 ml water, with the protection of $N_2$ and away from light, the mixture was heated in a water bath to 40° C.~60° C. in a water bath for 0.5 h~2 h. 50 ml 2-aminomethyl-cyclopentylamine (containing 5 mmol ammonia) solution was added in the reaction solution, which was kept under this condition to react for 0.5 h~2 h. A light yellow solid product was obtained by suction filtration and washed with water (10 ml×3 times) and ethyl ether (10 ml×3 times), to obtain 2.58 g product, with the yield of 92.31%. Elemental analysis: C, 12.71% (theoretical 12.88%), H, 1.72% (theoretical 1.79%), N, 5.11% (theoretical 5.01%).

Step 5: 2-aminomethyl-cyclopentylamine•dihydrated platinum (II) sulphate

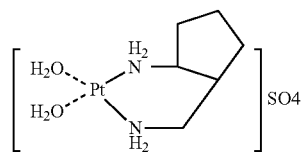

625 mg (2 mmol) $Ag_2SO_4$ was placed in a 100 ml three-necked flask, 30 ml water was added thereto and stirred, and 1.12 g (2 mmol) 2-aminomethyl-cyclopentylamine•diiodoplatinum (II) was added into the reaction solution and then 40 ml water was added to react, with the protection of $N_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-(2-aminomethyl-cyclopentylamine) platinum (II) acetate

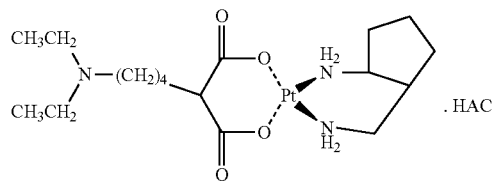

The pH of disodium 2-(4-diethylaminobutyl)-malonate solution was adjusted to 5~7 with 1M HAC and then cis-2-aminomethyl-cyclopentylamine•dihydrated platinum (II) sulphate aqueous solution was poured into the reaction solution, with the protection of $N_2$, the mixture was heated to 40° C.~75° C. in a water bath for 4 h~6 h, and the reaction solution was concentrated to a certain volume after suction filtration and stayed, to obtain 147 mg crystalline-type product.

The compound in Example 27 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 37.81% (theoretical 37.92%), H, 6.25% (theoretical 6.13%), N, 7.85% (theoretical 7.81%).

$^1$HNMR ($D_2O$) (ppm): δ3.61 (m, 1H), δ2.81 (q, 4H), δ2.69 (m, 1H), δ2.60 (d, 2H), δ2.53 (t, 2H), δ2.31 (m, 1H), δ2.18 (m, 2H), δ1.79 (m, 2H), δ1.45 (m, 2H), δ1.35 (m, 4H), δ1.22 (m, 2H), δ1.03 (t, 6H).

[Example 28]: 2-(4-diethylaminobutyl)-malonate•cis-ammonia•piperidine platinum (II) acetate Steps 1, 2 and 3 are the same as steps 1, 2 and 3 in [Example 1], respectively.

Step 4: ammonia•piperidine•diiodoplatinum (II)

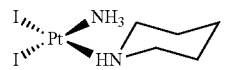

2.075 g (5 mmol) potassium tetrachloroplatinate (K$_2$PtCl$_4$) was added in 50 ml water and dissolved by stirring at room temperature, and 6.65 g (40 mmol) KI was added in the reaction solution after being dissolved with 50 ml water, with the protection of N$_2$ and away from light, the mixture was heated in a water bath to 40° C.~60° C. in a water bath for 0.5 h~2 h. 25 ml piperidine (containing 2.5 mmol ammonia) solution was added in the reaction solution, which was kept under this condition to react for 0.5 h~2 h. Then 25 ml ammonia water (containing 2.5 mmol ammonia) was added in the reaction solution, which was kept under this condition to react for 0.5 h~2 h. A light yellow solid product was obtained by suction filtration and washed with water (10 ml×3 times) and ethyl ether (10 ml×3 times), to obtain 2.40 g product, i.e., ammonia•piperidine•diiodoplatinum (II), with the yield of 87.1%. Elemental analysis: C, 10.71% (theoretical 10.89%), H, 2.42% (theoretical 2.54%); N, 5.23% (theoretical 5.08%).

Step 5: ammonia•piperidine•dihydrated platinum (II) sulphate

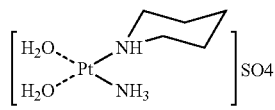

625 mg (2 mmol) Ag$_2$SO$_4$ was placed in a 100 ml three-necked flask, 30 ml water was added thereto and stirred, and 1.09 g (2 mmol) ammonia•piperidine•diiodoplatinum (II) was added into the reaction solution and then 40 ml water was added to react, with the protection of N$_2$ and away from light, the mixture was reacted at 40° C.~60° C. in a water bath for 4 h~8 h. After removing AgI precipitate by suction filtration, the filtrate was obtained, i.e., the aqueous solution of the product.

Step 6: 2-(4-diethylaminobutyl)-malonate•cis-ammonia•piperidine platinum (II) acetate

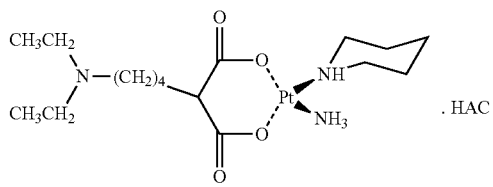

The pH of disodium 2-(4-diethylaminobutyl)-malonate solution was adjusted to 5~7 with 1M HAC and then cis-ammonia•cyclopentylamine•dihydrated platinum (II) sulphate aqueous solution was poured into the reaction solution, with the protection of N$_2$, the mixture was heated to 40° C.~75° C. in a water bath for 4 h~6 h, and the reaction solution was concentrated to a certain volume after suction filtration and stayed, to obtain 160 mg crystalline-type product.

The compound in Example 28 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 36.37% (theoretical 36.50%), H, 6.36% (theoretical 6.27%), N, 7.95% (theoretical 7.99%).

$^1$HNMR (D$_2$O) (ppm): δ3.61 (m, 1H), δ2.79 (q, 4H), δ2.67 (t, 4H), δ2.58 (t, 2H), δ2.19 (m, 4H), δ1.81 (m, 2H), δ1.40 (m, 2H), δ1.29 (m, 2H), δ1.21 (m, 2H), δ1.03 (t, 6H).

[Example 29]: 2-(4-trimethylaminobutyl)-malonate•cis-(1,2-trans-cyclohexanediamine) platinum(II) tosilate Step 1 is the same as step 1 in [Example 1], respectively.

Step 2: diethyl 2-(4-trimethylaminobutyl)-malonate

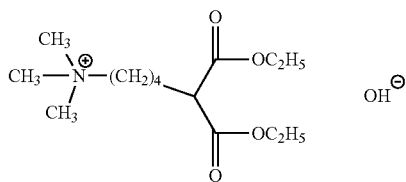

117.9 g, (0.4 mol) diethyl 4-bromobutyl-malonate was placed into a three-necked flask, 55.5 g (0.4 mol) anhydrous K$_2$CO$_3$ and 500 ml acetonitrile were added and stirred. 59 g (1.0 mol) trimethylamine was added in the reaction solution, and the mixture was heated to 45° C.~60° C. in an oil bath to react for 2 h-6 h, the insoluble substance was filtered out, the filtrate was pumped out and then the filtrate was dissolved by adding 1000 ml ethyl acetate and washed with saturated NaCl aqueous solution (250 ml×3 times), and the organic layer was dried over anhydrous MgSO$_4$ overnight, the solvent was pumped out under reduced pressure using a water pump, to obtain 99.0 g light yellow, light red, transparent substance, and the substance was dissolved with 50 ml water and then 50 g Ag$_2$O was added thereto, and centrifuged, the supernate fluid was respectively extracted with 300 ml ethyl acetate three times, the extracted solution was combined, and then ethyl acetate was removed by rotary evaporation to obtain 45.6 g product, with the yield of 39.18%.

Step 3: disodium 2-(4-trimethylaminobutyl)-malonate

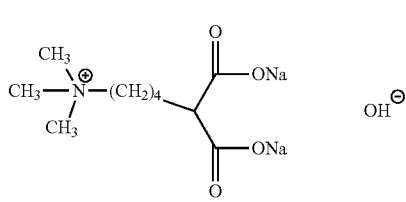

2M NaOH solution was obtained by dissolving 212 mg (5 mmol) NaOH with 2.5 mL water. 582 mg (2 mmol) diethyl 2-(4-trimethylaminobutyl)-malonate was placed into a 20 mL three-necked flask and the above NaOH solution was added thereto, stirring the mixture at room temperature for 45 h~60 h, to obtain a solution of disodium 2-(4-trimethyl-aminobutyl)-malonate.

Steps 4, 5 are the same as steps 4, 5 in [Example 3], respectively.

Step 6: 2-(4-trimethylaminobutyl)-malonate•cis-(1, 2-trans-cyclohexanediamine) platinum (II) tosilate

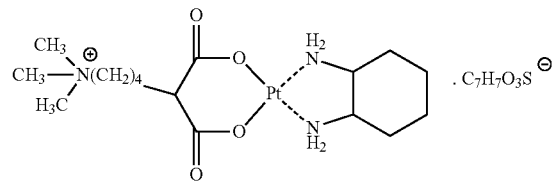

The pH of disodium 2-(4-trimethylaminobutyl)-malonate solution was adjusted to 5~7 with 1 M p-toluenesulfonic acid and then trans-cyclohexanediamine•dihydrated platinum (II) sulphate aqueous solution was poured into the reaction solution, with the protection of $N_2$, the mixture was heated to 40° C.~60° C. in a water bath for 4 h-8 h, and the reaction solution was added into 2.5 g silica gel for column chromatography (200-300 meshes) and stirred for 15 min and then pumped to be dryness, the mixture was treated by column chromatography to obtain 150 mg product.

The compound in Example 29 is soluble in water, the solubility is more than 300 mg/ml, and it can be easily converted into other types of organic or inorganic salts by ionization, the organic or inorganic salts may be, but not limited to, sulphate, mesylate, tartrate, succinate, acetate, citrate, tosilate, fumarate, etc. Elemental analysis of the free alkali: C, 35.70% (theoretical 35.42%), H, 6.21% (theoretical 6.09%), N, 7.79% (theoretical 7.75%).

$^1$HNMR ($D_2O$) (ppm): δ3.62 (m, 1H), δ2.79 (s, 9H), δ2.65 (m, 2H), δ2.45 (t, 2H), δ1.80 (m, 4H), δ1.46 (m, 4H), δ1.25 (m, 4H), δ1.01 (m, 2H).

Example 30-65

With reference to the above synthesis steps, the compounds in table 1 and table 2 below were produced, and $LD_{50}$ and $IC_{50}$ of anti-lung cancer A549 were also determined according to the methods of test example 1 and test example 2.

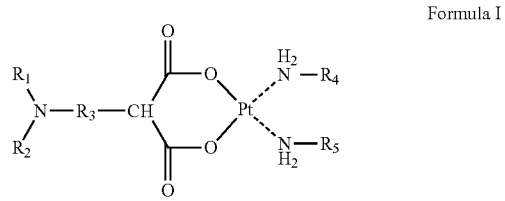

Formula I

—$NH_2$—$R_4$ and $NH_2$—$R_5$ of formula I of the above structure figure are modified to —$R_a$ and —$R_b$ (see table 1).

Table 1. Synthesized compounds with the structure of formula I, $LD_{50}$ value, mass spectra and value of anti-lung cancer A549 thereof.

TABLE 1

Compounds with formula I structure, their $LD_{50}$, mass spectra and $IC_{50}$ of anti-lung cancer A549

| Compound | $R_1$— | $R_2$— | —$R_3$— | —$R_a$ | —$R_b$ | $LD_{50}$ (mmol/kg) | Mass spectrometry (MS) | $IC_{50}$ (mM) |
|---|---|---|---|---|---|---|---|---|
| 30 | $C_2H_5$— | $CH_3$— | -CH2-CH2-) | —$NH_3$ | —$NH_3$ | 0.759 | 474 | 0.012 |
| 31 | $C_2H_5$— | $CH_3$— | -CH2-CH2-) | —N(H2)-cyclohexyl | —N(H2)- | 0.732 | 554 | 0.005 |
| 32 | $C_3H_7$— | $C_3H_7$— | | —N(H2)-cyclohexyl | —N(H2)- | 0.845 | 578 | 0.015 |
| 33 | | | —$C_4H_8$— | —N(H2)-cyclohexenyl | —N(H2)- | 0.826 | 548 | 0.007 |

TABLE 1-continued
Compounds with formula I structure, their LD$_{50}$, mass spectra and IC$_{50}$ of anti-lung cancer A549
| Compound | R$_1$— | R$_2$— | —R$_3$— | —R$_a$ | —R$_b$ | LD$_{50}$ (mmol/kg) | Mass spectrometry (MS) | IC$_{50}$ (mM) |
|---|---|---|---|---|---|---|---|---|
| 34 | 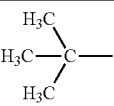 | CH$_3$— | —C$_4$H$_8$— | 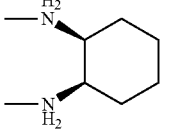 | | 0.905 | 552 | 0.011 |
| 35 | 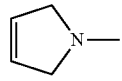 | | —C$_4$H$_8$— | 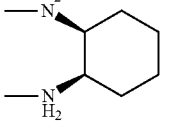 | | 0.762 | 534 | 0.004 |
| 36 | 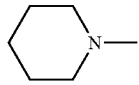 | | 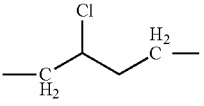 | 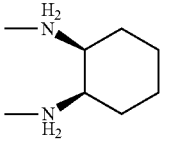 | | 0.713 | 584.5 | 0.007 |
| 37 | 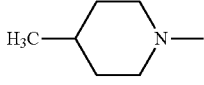 | | —C$_4$H$_8$— | 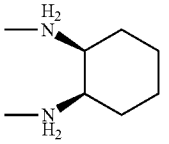 | | 0.825 | 564 | 0.009 |
| 38 | 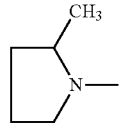 | | —C$_4$H$_8$— | 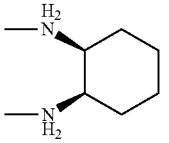 | | 0.818 | 550 | 0.006 |
| 39 | 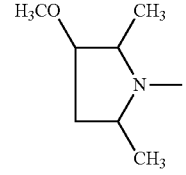 | | —C$_4$H$_8$— | 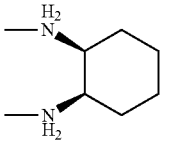 | | 0.711 | 594 | 0.006 |
| 40 | C$_2$H$_5$— | C$_2$H$_5$— | —C$_4$H$_8$— | 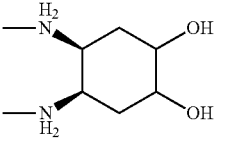 | | 0.683 | 570 | 0.021 |
| 41 | 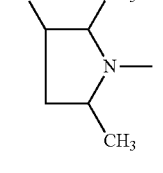 | | —C$_4$H$_8$— | 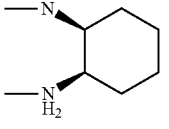 | | 0.675 | 598.5 | 0.013 |
| 42 | 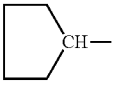 | 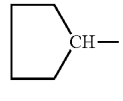 | —C$_4$H$_8$— | 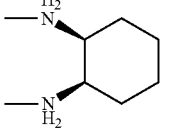 | | 0.826 | 618 | 0.005 |

TABLE 1-continued
Compounds with formula I structure, their $LD_{50}$, mass spectra and $IC_{50}$ of anti-lung cancer A549
| Compound | $R_1-$ | $R_2-$ | $-R_3-$ | $-R_a$ | $-R_b$ | $LD_{50}$ (mmol/kg) | Mass spectrometry (MS) | $IC_{50}$ (mM) |
|---|---|---|---|---|---|---|---|---|
| 43 | 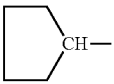 | $CH_3-$ | $-C_4H_8-$ | 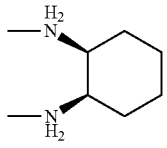 | | 0.841 | 564 | 0.005 |
| 44 | $CH_3-$ | $CH_3-$ | $-C_4H_8-$ | 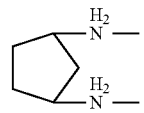 | | 0.857 | 496 | 0.024 |
| 45 | $CH_3-$ | $CH_3-$ | $-C_4H_8-$ | 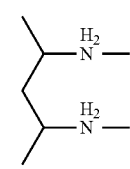 | | 0.834 | 498 | 0.031 |
| 46 | $CH_3-$ | $CH_3-$ | $-C_4H_8-$ | 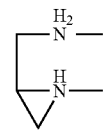 | | 0.823 | 468 | 0.027 |
| 47 | $CH_3-$ | $CH_3-$ | $-C_4H_8-$ | 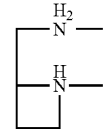 | | 0.815 | 482 | 0.023 |
| 48 | $CH_3-$ | $CH_3-$ | $-C_4H_8-$ | 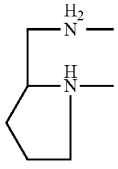 | | 0.831 | 496 | 0.031 |
| 49 | $CH_3-$ | $CH_3-$ | $-C_4H_8-$ | 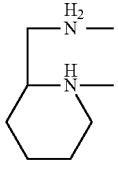 | | 0.817 | 510 | 0.045 |
| 50 | $C_3H_7-$ | $C_3H_7-$ | 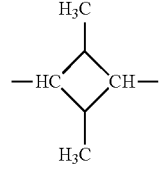 | 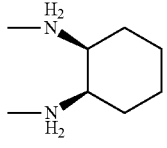 | | 0.773 | 592 | 0.012 |
| 51 | 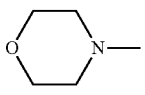 | | $-C_4H_8-$ | 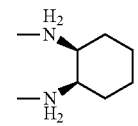 | | 0.654 | 552 | 0.026 |

TABLE 1-continued

Compounds with formula I structure, their LD$_{50}$, mass spectra and IC$_{50}$ of anti-lung cancer A549

| Compound | R$_1$— | R$_2$— | —R$_3$— | —R$_a$ | —R$_b$ | LD$_{50}$ (mmol/kg) | Mass spectrometry (MS) | IC$_{50}$ (mM) |
|---|---|---|---|---|---|---|---|---|
| 52 | HO—CH2— | CH$_3$— | —C$_4$H$_8$— | —NH$_3$ | cyclobutyl-NH— | 0.687 | 500 | 0.041 |
| 53 | cyclopropyl-CH— | CH$_3$— | —C$_4$H$_8$— | —NH$_3$ | —NH$_3$ | 0.874 | 456 | 0.054 |
| 54 | C$_2$H$_5$— | CH$_3$— | —CH$_2$—CH(OH)—CH$_2$— | trans-1,2-diaminocyclohexyl (—NH—, —NH$_2$) | | 0.792 | 540 | 0.015 |
| 55 | C$_2$H$_5$— | C$_2$H$_5$— | —C$_4$H$_8$— | cyclopentyl-CH$_2$— | cyclopentyl-NH— | 0.852 | 594 | 0.061 |
| 56 | cyclopropyl-CH— | cyclopropyl-CH— | —C$_4$H$_8$— | cyclopentyl-NH— | cyclopentyl-NH— | 0.816 | 618 | 0.057 |
| 57 | CH$_3$— | benzyl (PhCH$_2$—) | —C$_4$H$_8$— | trans-1,2-diaminocyclohexyl | | 0.613 | 586 | 0.032 |
| 58 | CH$_3$— | 4-Cl-C$_6$H$_4$-CH$_2$— | —C$_4$H$_8$— | trans-1,2-diaminocyclohexyl | | 0.607 | 620.5 | 0.037 |
| 59 | CH$_3$— | 4-Cl-2-F-C$_6$H$_3$-CH$_2$— | —C$_4$H$_8$— | —NH$_3$ | —NH$_3$ | 0.598 | 558.5 | 0.068 |
| 60 | C$_4$H$_9$— | CH$_3$— | —C$_4$H$_8$— | trans-1,2-diaminocyclohexyl | | 0.875 | 552 | 0.009 |
| 61 | H$_3$C—CH$_2$— | CH$_3$— | —C$_4$H$_8$— | trans-1,2-diaminocyclohexyl | | 0.837 | 552 | 0.014 |
| 62 | C$_2$H$_5$— | C$_2$H$_5$— | —C$_4$H$_8$— | —NH$_2$—CH$_2$—CH=CH—CH$_3$ | —NH$_2$—CH$_2$—C≡C—CH$_2$—CH$_3$ | 0.796 | 564 | 0.023 |
| 63 | C$_2$H$_5$— | C$_2$H$_5$— | —C$_4$H$_8$— | —NH$_2$—(CH$_2$)$_2$—CH$_3$ | pyrrolinyl-NH— | 0.804 | 567 | 0.025 |

TABLE 1-continued

Compounds with formula I structure, their LD$_{50}$, mass spectra and IC$_{50}$ of anti-lung cancer A549

| Compound | R$_1$— | R$_2$— | —R$_3$— | —R$_a$ | —R$_b$ | LD$_{50}$ (mmol/kg) | Mass spectrometry (MS) | IC$_{50}$ (mM) |
|---|---|---|---|---|---|---|---|---|
| 64 | C$_2$H$_5$— | C$_2$H$_5$— | —C$_4$H$_8$— | —NH$_2$—CH$_2$— | —NH$_2$—CH$_2$—N—(C$_2$H$_5$)$_2$ | 0.675 | 587 | 0.017 |

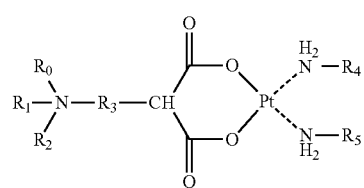

Formula II

—NH$_2$—R$_4$ and NH$_2$—R$_5$ of formula II of the above structure figure are modified to —R$_a$ and —R$_b$ (see table 2).

Table 2. Synthesized compounds with the structure of formula II, LD$_{50}$ value, mass spectra and IC$_{50}$ value of anti-lung cancer A549 thereof.

TABLE 2

Compounds with formula II structure, their LD$_{50}$, mass spectra and IC$_{50}$ of anti-lung cancer A549

| compound | R$_0$— | R$_1$— | R$_2$— | R$_3$— | —Ra | —R$_b$ | LD$_{50}$ VALUE (mmol/kg) | Mass spectrometry (MS) | IC$_{50}$ (mM) |
|---|---|---|---|---|---|---|---|---|---|
| 65 | CH$_3$— | C$_4$H$_9$— | CH$_3$— | —C$_4$H$_8$— | cyclohexane with —NH—, —NH—, OCH$_3$, OCH$_3$ | | 0.615 | 627 | 0.016 |
| 66 | C$_2$H$_5$— | C$_2$H$_5$— | C$_2$H$_5$— | —C$_4$H$_8$— | —NH$_3$ | —NH$_3$ | 0.677 | 487 | 0.020 |
| 67 | C$_2$H$_5$— | C$_2$H$_5$— | C$_2$H$_5$— | —C$_4$H$_8$— | —NH$_2$—(CH$_2$)$_3$—CH$_2$ | —NH$_2$—(CH$_2$)$_3$—CH$_2$ | 0.802 | 599 | 0.027 |
| 68 | C$_2$H$_5$— | C$_2$H$_5$— | C$_2$H$_5$— | —C$_4$H$_8$— | cyclohexane with —NH—, —NH—, OCH$_3$ | | 0.714 | 590 | 0.019 |

Phosphates with the molecular number of 1:1 composed of bases and phosphates of the compounds 30-68 in the above examples are all easily dissolved in water, their solubility are more than 300 mg/ml, and pH of the aqueous solution thereof are between 5 and 7.

[Test Example 1]: Acute Toxic Effect of Platinum Complex on Normal Mice

Kunming mice with 4~6 weeks old and 18 g~22 g by weight were taken, 50% males and 50% females. The platinum compounds of examples were dissolved with 5% glucose solution, and single intravenous administration (control drugs are carboplatin and cisplatin) was made at the different dosages. The condition of mortality and toxicity were observed after administration. Totally observing for 14 days, LD$_{50}$ value was calculated using Bliss method according to the mortality. See Table 3.

TABLE 3

LD$_{50}$ results of intravenous injection of cisplatin, carboplatin and platinum compounds of example in mice:

| Compound | LD$_{50}$ vALUE (mmol/kg) | Example compound | LD$_{50}$ value (mg/kg) |
|---|---|---|---|
| Cisplatin | 0.044 | Compound 15 | 0.872 |
| Carboplatin | 0.336 | Compound 16 | 0.767 |
| Compound 1 | 0.746 | Compound 17 | 0.729 |
| Compound 2 | 0.797 | Compound 18 | 0.810 |
| Compound 3 | 0.815 | Compound 19 | 0.767 |
| Compound 4 | 0.823 | Compound 20 | 0.834 |
| Compound 5 | 0.845 | Compound 21 | 0.757 |
| Compound 6 | 0.756 | Compound 22 | 0.779 |
| Compound 7 | 0.778 | Compound 23 | 0.831 |
| Compound 8 | 0.801 | Compound 24 | 0.769 |
| Compound 9 | 0.725 | Compound 25 | 0.722 |
| Compound 10 | 0.791 | Compound 26 | 0.722 |
| Compound 11 | 0.803 | Compound 27 | 0.755 |

TABLE 3-continued

LD$_{50}$ results of intravenous injection of cisplatin, carboplatin and platinum compounds of example in mice:

| Compound | LD$_{50}$ vALUE (mmol/kg) | Example compound | LD$_{50}$ value (mg/kg) |
|---|---|---|---|
| Compound 12 | 0.729 | Compound 28 | 0.725 |
| Compound 13 | 0.816 | Compound 29 | 0.638 |
| Compound 14 | 0.866 | | |

Conclusion: The acute toxicity of the molar concentration of the compounds of the examples 1-60 is much smaller than that of cisplatin and carboplatin.

[Test Example 2]: Cytotoxcity Effects of the Platinum Compounds on Tumor Cells

The toxic effects of the platinum compounds of examples on tumor cells were observed by applying a MTT colorimetric method. Several kinds of tumor cells in an exponential growth phase were prepared into single cell suspension, inoculated on a 96-well plate with the density of $4\times10^4$/well, cultivated with a 1640 culture medium containing 10% fetal bovine serum (complete medium) at 37° C. for 24 hours to let cell adherence, and the final culture volume was 100 μl. Cell morphologies were observed after being cultivated for 24 hours. For the dosage of the platinum compounds, since IC$_{50}$ values of various cells are different, the following concentrations are determined through a pretest: administering 200 μg/ml, 60 μg/ml, 20 μg/ml, 6 μg/ml, 2 μg/ml, 0.6 μg/ml of cisplatin, 200 μg/ml, 60 μg/ml, 20 μg/ml, 6 μg/ml, 2 μg/ml, 0.6 μg/ml of carboplatin, and appropriately adjusting the dosages of the platinum compounds of the examples depending on the sensitivity to each kind of cells. The results are shown in Table 4-9 below,

TABLE 4

The cytotoxicity IC$_{50}$ of different subjected platinum pharmaceutical compounds to different cells
IC$_{50}$ (n = 6) of different cell strains to chemotherapeutic drugs

| Cell trains | IC$_{50}$ (mM) | | | | | |
|---|---|---|---|---|---|---|
| | Carboplatin | Cisplatin | Compound 1 | Compound 2 | Compound 3 | Compound 4 |
| Breast cancer MCF-7 | 0.103 | 0.012 | 0.006 | 0.010 | 0.007 | 0.005 |
| Breast cancer MCF-7 cisplatin resistance strain | 0.255 | 0.015 | 0.009 | 0.015 | 0.021 | 0.016 |
| Lung cancer A549 | 0.232 | 0.016 | 0.009 | 0.032 | 0.008 | 0.021 |
| Lung cancer H292 | 0.055 | 0.0053 | 0.003 | 0.011 | 0.006 | 0.008 |

TABLE 5

The cytotoxicity IC$_{50}$ of different subjected platinum pharmaceutical compounds to different cells
IC$_{50}$ (n = 6) of different cell strains to chemotherapeutic drugs

| Cell strains | IC$_{50}$ (mM) | | | | | |
|---|---|---|---|---|---|---|
| | Carboplatin | Cisplatin | Compound 5 | Compound 6 | Compound 7 | Compound 8 | Compound 9 |
| Alveolar Epithelial cells BEAS-2B | 0.037 | 0.0033 | 0.002 | 0.003 | 0.004 | 0.005 | 0.002 |
| Lung cancer Lewis | 0.038 | 0.045 | 0.018 | 0.041 | 0.021 | 0.025 | 0.050 |
| colon cancer SW480 | 0.087 | 0.015 | 0.009 | 0.002 | 0.010 | 0.016 | 0.014 |
| Lung cancer H292 | 0.055 | 0.0053 | 0.006 | 0.007 | 0.004 | 0.004 | 0.008 |

TABLE 6

The cytotoxicity IC$_{50}$ of different subjected platinum pharmaceutical compounds to different cells
IC$_{50}$ (n = 6) of different cell strains to chemotherapeutic drugs

| Cell lines | IC$_{50}$ (mM) | | | | | |
|---|---|---|---|---|---|---|
| | Carboplatin | Cisplatin | Compound 10 | Compound 11 | Compound 12 | Compound 13 | Compound 14 |
| Alveolar epithelial cells BEAS-2B | 0.037 | 0.0033 | 0.003 | 0.002 | 0.008 | 0.003 | 0.005 |
| Lung cancer Lewis | 0.038 | 0.045 | 0.051 | 0.049 | 0.018 | 0.059 | 0.036 |
| colon cancer SW480 | 0.087 | 0.015 | 0.013 | 0.021 | 0.018 | 0.015 | 0.017 |

TABLE 6-continued

The cytotoxicity IC$_{50}$ of different subjected platinum pharmaceutical compounds to different cells
IC$_{50}$ (n = 6) of different cell strains to chemotherapeutic drugs

| | | | IC$_{50}$ (mM) | | | | |
|---|---|---|---|---|---|---|---|
| Cell lines | Carboplatin | Cisplatin | Compound 10 | Compound 11 | Compound 12 | Compound 13 | Compound 14 |
| Lung cancer H292 | 0.055 | 0.0053 | 0.003 | 0.005 | 0.006 | 0.009 | 0.012 |

TABLE 7

The cytotoxicity IC$_{50}$ of different subjected platinum pharmaceutical compounds to different cells
IC$_{50}$ (n = 6) of different cell strains to chemotherapeutic drugs

| | | | IC$_{50}$ (mM) | | | | |
|---|---|---|---|---|---|---|---|
| Cell strains | Carboplatin | Cisplatin | Compound 15 | Compound 16 | Compound 17 | Compound 18 | Compound 19 |
| Testis cell ST | 0.195 | 0.00899 | 0.011 | 0.010 | 0.016 | 0.022 | 0.013 |
| gastric cancer MGC803 | 0.625 | 0.0025 | 0.003 | 0.004 | 0.005 | 0.002 | 0.005 |
| colon cancer SW480 | 0.087 | 0.015 | 0.018 | 0.013 | 0.007 | 0.014 | 0.023 |
| Lung cancer H292 | 0.055 | 0.0053 | 0.010 | 0.005 | 0.004 | 0.008 | 0.006 |

TABLE 8

The cytotoxicity (IC$_{50}$) of different subjected platinum pharmaceutical compounds to different cells
IC$_{50}$ (n = 6) of differnt cell strains to chemotherapeutic drugs

| | | | IC$_{50}$ (mM) | | | | |
|---|---|---|---|---|---|---|---|
| Cell strains | Carboplatin | Cisplatin | Compound 20 | Compound 21 | Compound 22 | Compound 23 | Compound 24 |
| Testis cell ST | 0.195 | 0.00899 | 0.011 | 0.013 | 0.014 | 0.008 | 0.006 |
| gastric cancer MGC803 | 0.625 | 0.0025 | 0.004 | 0.005 | 0.007 | 0.005 | 0.003 |
| Esophagus cancer ECA109 | 0.052 | 0.073 | 0.017 | 0.015 | 0.102 | 0.066 | 0.052 |
| Lung cancer H292 | 0.055 | 0.0053 | 0.005 | 0.012 | 0.005 | 0.014 | 0.003 |

TABLE 9

The cytotoxicity IC$_{50}$ of different subjected platinum pharmaceutical compounds to different cells
IC$_{50}$ (n = 6) of different cells strains to chemotherapeutic drugs

| | | | IC$_{50}$ (mM) | | | | |
|---|---|---|---|---|---|---|---|
| Cell strains | Carboplatin | Cisplatin | Compound 25 | Compound 26 | Compound 27 | Compound 28 | Compound 29 |
| Testis cell ST | 0.195 | 0.00899 | 0.007 | 0.011 | 0.013 | 0.061 | 0.008 |
| gastric cancer MGC803 | 0.625 | 0.0025 | 0.003 | 0.001 | 0.005 | 0.006 | 0.002 |
| Esophagus cancer ECA109 | 0.052 | 0.073 | 0.029 | 0.091 | 0.054 | 0.046 | 0.025 |
| Lung cancer H292 | 0.055 | 0.0053 | 0.006 | 0.004 | 0.004 | 0.011 | 0.007 |

As can be seen from Tables 1-2, and 4-9, the compounds of Examples 1-29 have equivalent or stronger cytotoxic effects in vitro with cisplatin, and much stronger than carboplatin.

[Formulation Example 1]: Preparation of Injection

Prescription 1

| | |
|---|---|
| The phosphate of the compound in Example 2 | 10 g |
| Glucose | 50 g |
| Adding water for injection to | 1000 ml |
| Produced 1000 | |

Process: 10 g tosilate of the compound in Example 2 and 50 g glucose were added into a 2000 ml glassware, and dissolved by adding water for injection to 1000 ml at normal temperature, after filtering with 0.22 μm microporous membrane, the filtrate was charged into 1 ml ampoules to obtain the product with the specification of 10 mg/ml.

Prescription 2

| | |
|---|---|
| The mesylate of the compound in Example 6 | 10 g |
| Glucose | 50 g |
| Adding water for injection to | 1000 ml |
| Produced 1000 | |

Process: 10 g mesylate of the compound in Example 6, i.e. 10 g mesylate and 50 g glucose were added into a 1000 ml glassware, and dissolved by adding water to 1000 ml for injection at normal temperature, after filtering with 0.22 μm microporous membrane, the filtrate was charged into 2 ml vial to obtain the product with the specification of 10 mg/bottle.

[Formulation Example 2]: Preparation of Freeze-Dried Powder Injection

Prescription 1

| | |
|---|---|
| The tosilate of the compound in Example 9 | 10 g |
| Mannitol | 50 g |
| Adding water for injection to | 1000 ml |
| Produced 1000 | |

Process: 10 g compound in Example 9 and 50 g Mannitol were added into a 1000 ml glassware, and dissolved by adding water for injection to 1000 ml at normal temperature, after filtering with 0.22 μm microporous membrane, the filtrate was charged into 2 ml vial, 1 ml solution for each bottle, and then freeze-dried to obtain the product with the specification of 10 mg/bottle.

Prescription 2

| | |
|---|---|
| The phosphate of the compound in Example 11 | 20 g |
| Mannitol | 50 g |
| Adding water for injection to | 1000 ml |
| Produced 1000 | |

Process: 20 g phosphate of the compound in Example 11 and 50 g Mannitol were added into a 1000 ml glassware, and dissolved by adding water for injection to 1000 ml at normal temperature, after filtering with 0.22 μm microporous membrane, the filtrate was charged into 2 ml vial, 1 ml solution for each bottle, and then freeze-dried to obtain the product with the specification of 20 mg/bottle.

Prescription 3

| | |
|---|---|
| The acetate of the compound in Example 13 | 50 g |
| Adding water for injection to | 1000 ml |
| Produced 1000 | |

Process: 50 g acetate of the compound in Example 20 was added into a 1000 ml glassware, and dissolved by adding water for injection to 1000 ml at normal temperature, after filtering with 0.22 μm microporous membrane, the filtrate was charged into 2 ml vial, 1 ml solution for each bottle, and then freeze-dried to obtain the product with the specification of 50 mg/bottle.

The invention claimed is:

1. A platinum compound of formula A,

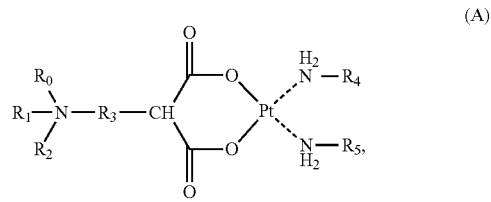

(A)

or a pharmaceutically acceptable salt, solvate, stereoisomer, or prodrug thereof, wherein:

$R_0$ may or may not exist; when $R_0$ exists, it is selected from alkyl, cycloalkyl, alkoxyalkyl, alkylaminoalkyl, heterocyclyl, alkenyl and alkynyl, which are unsubstituted or optionally substituted by halogen, hydroxyl, alkoxy, alkyl, alkoxyalkyl, cycloalkyl, heterocyclyl, and/or aryl, provided that if $R_0$ contains an unsaturated bond, the atom of the unsaturated bond cannot be directly connected with nitrogen atom, and then formula A is quaternary ammonium compound; while when $R_0$ does not exist, formula A is a tertiary amine compound;

$R_1$ and $R_2$ may be the same or different, and are selected from hydrogen, alkyl, cycloalkyl, alkoxyalkyl, alkylaminoalkyl, heterocyclyl, alkenyl, and alkynyl, which are unsubstituted or optionally substituted by halogen, hydroxyl, alkoxy, alkyl, alkoxyalkyl, cycloalkyl, heterocyclyl, and/or aryl, provided that if $R_1$ or $R_2$ contains an unsaturated bond, the atom of the unsaturated bond cannot be directly connected with nitrogen atom; or $R_1$, $R_2$ and the nitrogen atom connected with them may together form a closed saturated or unsaturated heterocyclic ring; said ring can be three-membered, four-membered, five-membered, six-membered, seven-membered or eight-membered ring; said ring may be optionally fused with other rings and may be optionally substituted by halogen, hydroxyl, alkoxy, alkyl, alkoxyalkyl, cycloalkyl, heterocyclyl, and/or aryl, provided that the atom connected with said nitrogen atom is a saturated carbon atom;

$R_3$ is $C_4$ linear alkylene or $C_4$ cycloalkylene, which can be optionally substituted by one or more alkoxy, hydroxyl, alkyl, halogen, haloalkyl, alkoxyalkyl, and/or heterocyclyl;

$R_4$ and $R_5$ may be the same or different, and are selected from: hydrogen, hydroxyl, alkyl, cycloalkyl, alkoxy, alkoxyalkyl, heterocyclyl, alkenyl, and alkynyl; wherein said alkyl, alkenyl, alkynyl, cycloalkyl, alkoxyalkyl, alkylaminoalkyl and heterocyclyl can be unsubstituted or optionally substituted, preferably substituted by halogen, hydroxyl, alkoxy, linear or branched alkyl, alkoxyalkyl, cycloalkyl and/or heterocyclyl; or $R_4$, $R_5$ and the atoms connected with them may together form a closed ring, which may be four-membered, five-membered, six-membered, seven-membered or eight-membered ring; said ring may be optionally condensed with other rings and may be optionally substituted.

2. The platinum compound or the pharmaceutical acceptable salt, solvate, stereoisomer, or prodrug thereof according to claim 1, wherein: $R_3$ is $C_4$ linear alkylene, which can be optionally substituted by one or more alkoxy, hydroxyl, and/or alkyl, and said alkoxy is selected from: methoxyl, ethoxyl, propoxyl, and isopropoxyl; said alkyl is selected from methyl, ethyl and isopropyl.

3. The platinum compound or the pharmaceutical acceptable salt, solvate, stereoisomer, or prodrug thereof according to claim 1, wherein: $R_3$ is the $C_4$ cycloalkylene, which can be optionally substituted by one or more alkoxy, hydroxyl, and/or alkyl, and said alkoxy is selected from methoxyl, ethoxyl, propoxyl, and isopropoxyl; said alkyl is selected from methyl, ethyl, and isopropyl.

4. The platinum compound or the pharmaceutical acceptable salt, solvate, stereoisomer, or prodrug thereof according to claim 1, wherein: $R_1$ and $R_2$ are selected independently from hydrogen, methyl, ethyl or propyl; or $R_1$, $R_2$ and the atoms connected with them can together form a closed ring; said ring is a pyrrole ring or pyridine ring and can be optionally substituted.

5. The platinum compound or the pharmaceutical acceptable salt, solvate, stereoisomer, or prodrug thereof according to claim 1, wherein the structure thereof is shown in formula C:

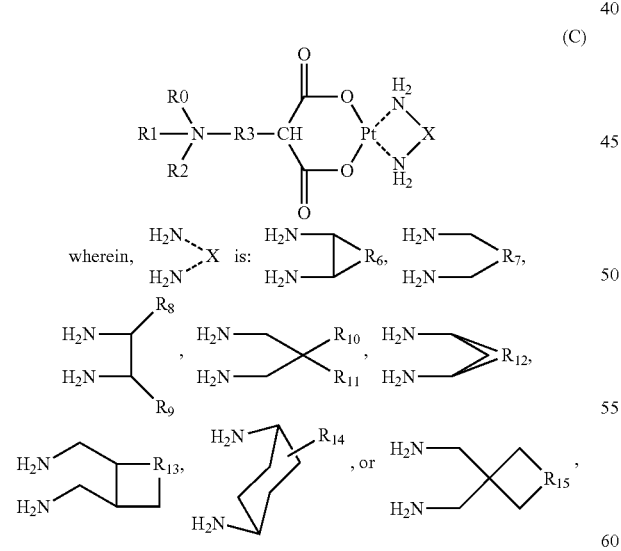

and the above structure can be optionally substituted;

$R_6$ is $(CH_2)_n$, wherein n=1-6, preferably 3-5, the most preferably 4, wherein some —$CH_2$— is optionally substituted by —O—; wherein one or more hydrogens of $(CH_2)$— are optionally substituted by fluorine, alkyl, hydroxyl, alkoxy, and/or heterocyclyl;

$R_7$ is $(CH_2)_n$, wherein n=0-3, preferably n=0-2; wherein some —$CH_2$— is optionally substituted by —O—; wherein one or more hydrogens of $(CH_2)_n$ are optionally substituted by halogen, alkyl, hydroxyl, hydroxyalkyl, alkoxy, and/or heterocyclyl;

$R_8$ and $R_9$ are selected from hydrogen, halogen, hydroxyl, hydroxyalkyl, alkyl, alkoxy and heterocyclyl; $R_8$ and $R_9$ may be the same or different, preferably hydroxymethyl;

$R_{10}$ and $R_{11}$ are selected from hydrogen, halogen, hydroxyalkyl, alkyl, alkoxy, and heterocyclyl; $R_{10}$ and $R_{11}$ may be the same or different, preferably hydroxymethyl;

$R_{12}$ is $(CH_2)_n$, wherein n=2-4; wherein some —$CH_2$— is optionally substituted by —O—, and one or more hydrogens of $(CH_2)_n$ are optionally substituted by halogen, alkyl, hydroxyl, alkoxy and/or heterocyclyl;

$R_{13}$ is —$CH_2$— or —O—, preferably —$CH_2$—;

$R_{14}$ is selected from hydrogen, halogen, alkyl, alkoxy, heterocyclyl, hydroxyalkyl and hydroxyl; $R_{14}$ is preferably hydrogen;

$R_{15}$ is selected from: $(CH_2)_n$, wherein n=1-3, —$CH_2$—O—, —O— and —$CH_2$—O—$CH_2$—; wherein one or more hydrogens of $(CH_2)_n$ are optionally substituted by alkyl, alkoxy, heterocyclyl, hydroxyl, and/or hydroxyalkyl; preferably —$CH_2$—O—$CH_2$—.

6. The platinum compound or the pharmaceutical acceptable salt, solvate, stereoisomer, or prodrug thereof according to claim 5, wherein said compound is as shown in the formulae below:

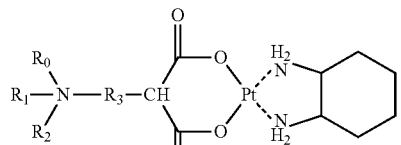

(D1)

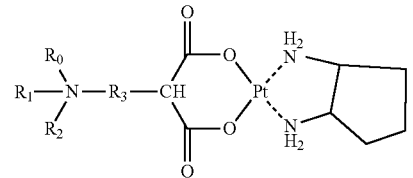

(D2)

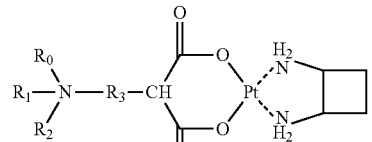

(D3)

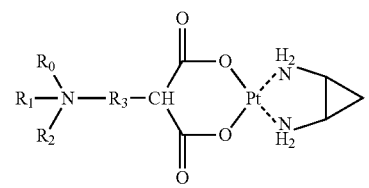

(D4)

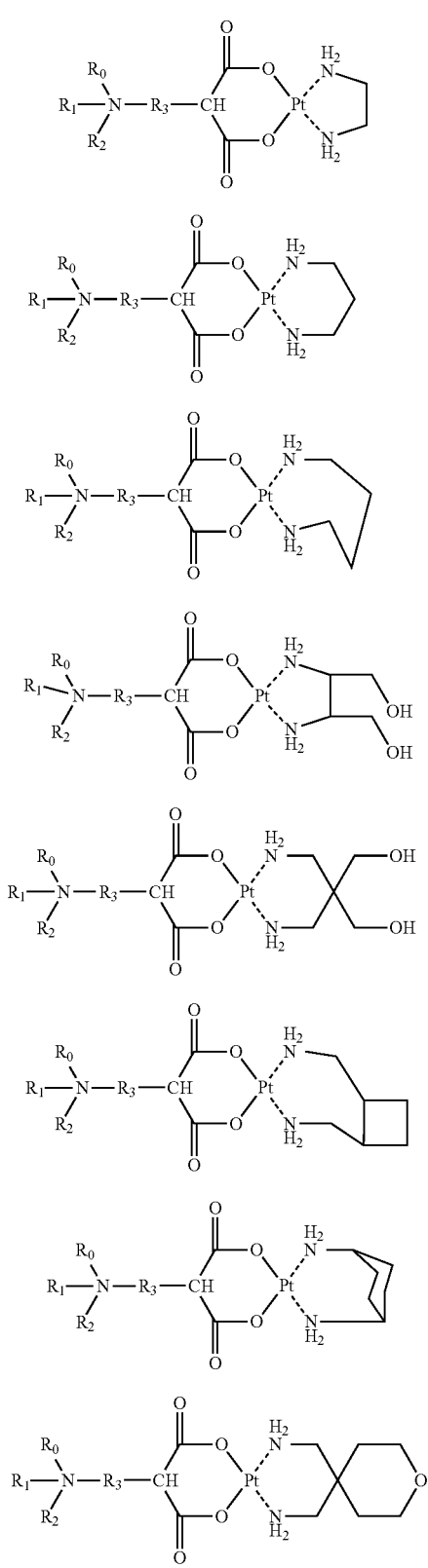

wherein:
R₀ may or may not exist; when R₀ exists, it is selected from alkyl, cycloalkyl, alkoxyalkyl, alkylaminoalkyl, heterocyclyl, alkenyl and alkynyl, which are unsubstituted or optionally substituted by halogen, hydroxyl, alkoxy, alkyl, alkoxyalkyl, cycloalkyl, heterocyclyl, and/or aryl, provided that if R₀ contains an unsaturated bond, the atom of the unsaturated bond cannot be directly connected with nitrogen atom, and then formula A is quaternary ammonium compound; while when R₀ does not exist, formula A is a tertiary amine compound;

R₁ and R₂ may be the same or different, and are selected from hydrogen, alkyl, cycloalkyl, alkoxyalkyl, alkylaminoalkyl, heterocyclyl, alkenyl, and alkynyl, which are unsubstituted or optionally substituted by halogen, hydroxyl, alkoxy, alkyl, alkoxyalkyl, cycloalkyl, heterocyclyl, and/or aryl, provided that if R₁ or R₂ contains an unsaturated bond, the atom of the unsaturated bond cannot be directly connected with nitrogen atom; or R₁, R₂ and the nitrogen atom connected with them may together form a closed saturated or unsaturated heterocyclic ring; said ring can be three-membered, four-membered, five-membered, six-membered, seven-membered or eight-membered ring; said ring may be optionally fused with other rings and may be optionally substituted by halogen, hydroxyl, alkoxy, alkyl, alkoxyalkyl, cycloalkyl, heterocyclyl, and/or aryl, provided that the atom connected with said nitrogen atom is a saturated carbon atom;

R₃ is C₄ linear alkylene or C₄ cycloalkylene, which can be optionally substituted by one or more alkoxy, hydroxyl, alkyl, halogen, haloalkyl, alkoxyalkyl, and/or heterocyclyl.

7. The platinum compound or the pharmaceutical acceptable salt, solvate, stereoisomer or prodrug thereof according to claim 1, wherein said compound is selected from the group consisting of:
Compound 1: 2-(4-diethylamino butyl)-malonate•cis-diamine platinum (II) acetate;
Compound 2: 2-(4-diethylamino butyl)-malonate•cis-(1,2-ethylenediamine) platinum (II) tosilate;
Compound 3: 2-(4-diethylamino butyl)-malonate•cis-(1,2-trans-cyclohexanediamine) platinum (II) tosilate;
Compound 4: 2-(4-(1-piperidyl)-butyl)-malonate•cis-diamine platinum (II) phosphate;
Compound 5: 2-(4-(1-tetrahydropyrrolidinyl)-butyl)-malonate•cis-diamine platinum (II) phosphate;
Compound 6: 2-(3-dimethylamino cyclobutyl)-malonate•cis-diamine platinum (II) mesylate;
Compound 7: 2-(4-di-n-propylamino butyl)-malonate•cis-diamine platinum (II) phosphate;
Compound 8: 2-(3-methyl-4-diethylamino butyl)-malonate•cis-diamine platinum (II) acetate;
Compound 9: 2-(4-(1-piperidyl)-butyl)-malonate•cis-(1,2-trans-cyclohexanediamine) platinum (II) tosilate;
Compound 10: 2-(4-(2-methyl-1-tetrahydropyrrolidinyl)-butyl)-malonate•cis-diamine platinum (II) phosphate;
Compound 11: 2-(4-amino butyl)-malonate•cis-(1,2-trans-cyclohexanediamine) platinum (II) phosphate;
Compound 12: 2-(4-ethylamino butyl)-malonate•cis-(1,2-trans-cyclohexanediamine) platinum (II) phosphate;
Compound 13: 2-(4-N-methyl-isopropylamino butyl)-malonate•cis-diamine platinum (II) acetate;
Compound 14: 2-(4-diethylamino butyl)-malonate•cis-(1,2-trans-cyclopentanediamine) platinum (II) phosphate;
Compound 15: 2-(4-diethylamino butyl)-malonate•cis-(1,2-trans-cyclobutanediamine) platinum (II) succinate;
Compound 16: 2-(4-diethylamino butyl)-malonate•cis-(1,2-trans-cyclopropanediamine) platinum (II) phosphate;

Compound 17: 2-(4-diethylamino butyl)-malonate•cis-(1, 2-ethylenediamine) platinum (II) tosilate;

Compound 18: 2-(4-diethylamino butyl)-malonate•cis-(1, 3-propanediamine) platinum (II) phosphate;

Compound 19: 2-(4-diethylamino butyl)-malonate•cis-(1, 4-butanediamine) platinum (II) phosphate;

Compound 20: 2-(2-diethylamino butyl)-malonate•cis-1, 2-(1,2-bis hydroxymethyl)-ethylene diamine platinum (II) phosphate;

Compound 21: 2-(4-diethylamino butyl)-malonate•cis-1, 3-(2,2-hydroxymethyl)-propane diamine platinum (II) phosphate;

Compound 22: 2-(4-diethylamino butyl)-malonate•cis-1, 4-(trans-2, 3-cyclobutyl)-butanediamine platinum (II) phosphate;

Compound 23: 2-(4-diethylamino butyl)-malonate•cis-(1, 4-cyclohexyldiamine) platinum (II) phosphate;

Compound 24: 2-(4-diethylamino butyl)-malonate•cis-1, 3-(2,2-(4-oxacyclohexyl))-propanediamine platinum (II) phosphate;

Compound 25: 2-(4-diethylamino butyl)-malonate•cis-dicyclopentylamine platinum (II) acetate;

Compound 26: 2-(4-diethylamino butyl)-malonate•cis-•ammonia•cyclopentylamine platinum (II) acetate;

Compound 27: 2-(4-diethylamino butyl)-malonate•cis-•(2-aminomethyl-cyclopentylamine) platinum (II) acetate;

Compound 28: 2-(4-diethylamino butyl)-malonate•cis-•ammonia piperidine platinum (II) acetate; and Compound 29: 2-(4-trimethylamino butyl)-malonate-cis-(1, 2-trans-cyclohexanediamine) platinum (II) tosilate.

8. A pharmaceutical composition comprising the compound according to claim 1 and a pharmaceutically acceptable carrier.

9. The pharmaceutical composition according to claim 8, wherein said pharmaceutical composition further comprises one or more of other drugs for the treatment of cancers.

10. A method for preparing the platinum compound according to claim 1, including the following steps:

(1) adding potassium chloroplatinite into water and stirring at room temperature to dissolve it, dissolving potassium iodide by water before adding into the above potassium chloroplatinite solution to undergo reaction away from light in water bath under nitrogen charging condition;

(2) dissolving $R_4NH_2$ by water and adding into the reaction solution obtained in (1) before reacting under water bath condition;

(3) cooling the above reaction solution below room temperature, dissolving $R_5NH_2$ by water and then adding to the reaction solution obtained in (2) to undergo reaction under water bath, with a quality of yellow deposit generated; after cooling the reaction solution below room temperature, obtaining diiododiamine platinum (II) through suction filtration and washing;

(4) adding $Ag_2SO_4$ into water and stirring, adding the above diiododiamine platinum (II) into the reaction solution and then adding water to undergo reaction away from light in water bath under nitrogen charging condition, obtaining dihydroldiamine platinum (II) sulfate by suction filtration;

(5) placing diethyl malonate and Br—$R_3$—Br into a flask, adding $K_2CO_3$ and tetrabutylammonium bromide into the flask and stirring, and then heating the reaction; after removal of solid by suction filtration and washing, combining filtrate, washing the organic layer, drying it, and undergoing reduced pressure distillation of the solvent to collect the distillate;

(6) placing 2-Br—$R_3$-diethyl malonate into a flask, adding anhydrous $K_2CO_3$ and acetonitrile, and stirring them; adding $R_1$—NH—$R_2$ or $R_1$—N($R_0$)—$R_2$ into the reaction solution, heating the reaction, and removing insoluble substance through filtration; pumping the filtrate to dryness, and then dissolving the residue in organic solvent; obtaining a product through washing with aqueous solution, drying the organic layer, and pumping out the solvent under reduced pressure; and purifying the product;

(7) placing the product obtained in (6) into a flask, adding NaOH solution and stirring at room temperature; and (8) after adjusting the product obtained in (7) with acid solution, adding the product obtained in (4), and heating the mixture to obtain the platinum compound of the present invention.

11. The method for preparing the platinum compound according to claim 5 including the following steps:

(1) adding potassium chloroplatinite into water and stirring at room temperature to dissolve it, dissolving potassium iodide by water before adding into the above potassium chloroplatinite solution to undergo reaction away from light in water bath under nitrogen charging condition;

(2) dissolving bidentate ammonia $NH_2$—X—$NH_2$ by water and adding into the reaction solution obtained in (1) before reacting under water bath condition, with a quantity of yellow deposit generated; after cooling the reaction mixture below room temperature, obtaining bidentate diiododiamine platinum (II) through suction filtration and washing;

(3) adding $Ag_2SO_4$ into water and stirring, adding the above diiododiamine platinum (II) into the reaction solution and then adding water to undergo reaction away from light in water bath under nitrogen charging condition, obtaining dihydroldiamine platinum (II) sulfate by suction;

(4) placing diethyl malonate and Br—$R_3$—Br into a flask, adding $K_2CO_3$ and tetrabutylammonium bromide into the flask and stirring, and then heating the reaction; after removal of solid by suction filtration and washing, combining filtrate, washing the organic layer, drying it, and undergoing reduced pressure distillation of the solvent to collect the distillate;

(5) placing 2-Br—$R_3$-diethyl malonate into a flask, adding anhydrous $K_2CO_3$ and acetonitrile, and stirring them; adding $R_1$—NH—$R_2$ or $R_1$—N($R_0$)—$R_2$ into the reaction solution, heating the reaction, and removing insoluble substance through filtration; pumping the filtrate to dryness, and then dissolving the residue in organic solvent; obtaining a product through washing with aqueous solution, drying the organic layer, and pumping out the solvent under reduced pressure; and purifying the product;

(6) placing the product obtained in (5) into a flask, adding NaOH solution and stirring at room temperature; and;

(7) after adjusting the product in (6) with acid solution, adding the product obtained in (3), and heating the mixture to obtain the platinum compound of the present invention.

12. A kit comprising the pharmaceutical composition according to claim 8 or 9 and instructions, wherein said kit further comprises one or more other drugs for the treatment of cancers.

* * * * *